US007994357B2

(12) United States Patent
Huang et al.

(10) Patent No.: US 7,994,357 B2
(45) Date of Patent: Aug. 9, 2011

(54) CINAMIC COMPOUNDS AND DERIVATIVES THEREFROM FOR THE INHIBITION OF HISTONE DEACETYLASE

(75) Inventors: Chung-Yang Huang, Taipei (TW); Chia-Nan Chen, Taipei (TW); Wei-Jan Huang, Taipei (TW); Chia-Wei Lin, Taipei (TW); Jing-Shi Huang, Taipei (TW); Li-Ling Chi, Taipei (TW); Ai-Ling Chen, Taipei (TW); Chi-Yun Lee, Taipei (TW); Yu-Chen Huang, Taipei (TW)

(73) Assignee: Naturewise Biotech & Medicals Corporation, Taipei (TW)

(*) Notice: Subject to any disclaimer, the term of this patent is extended or adjusted under 35 U.S.C. 154(b) by 0 days.

(21) Appl. No.: 12/418,373

(22) Filed: Apr. 3, 2009

(65) Prior Publication Data

US 2010/0256401 A1 Oct. 7, 2010

(51) Int. Cl.
*C07C 303/00* (2006.01)
*C07C 313/00* (2006.01)
*C07C 259/04* (2006.01)
*C07D 307/00* (2006.01)

(52) U.S. Cl. ............. 558/48; 558/61; 562/621; 549/469
(58) Field of Classification Search .................. 549/469; 558/61, 48; 562/621
See application file for complete search history.

(56) References Cited

U.S. PATENT DOCUMENTS

| 6,087,367 | A  | 7/2000  | Breslow et al. |
| 6,174,905 | B1 | 1/2001  | Suzuki et al. |
| RE38,506  | E  | 4/2004  | Breslow et al. |
| 6,888,027 | B2 | 5/2005  | Watkins et al. |
| 7,169,801 | B2 | 1/2007  | Bressi et al. |
| 7,399,787 | B2 | 7/2008  | Chiao et al. |
| 2004/0235888 | A1 | 11/2004 | Yamamori et al. |
| 2008/0242648 | A1 | 10/2008 | Ordentlich et al. |

FOREIGN PATENT DOCUMENTS

| EP | 0847992 | 6/1998 |
| EP | 1301184 | 4/2003 |
| JP | 10138957 | 8/1996 |
| WO | WO01/38322 | 5/2001 |
| WO | WO02/22577 | 3/2002 |
| WO | WO2007/018314 | 2/2007 |
| WO | WO2008/154801 | 12/2008 |

OTHER PUBLICATIONS

Wolff, Burger's medicinal Chemistry and Drug Discovery, vol. 1, Principles and Practice, John Wiley & sons, New York, 1997.*
West, Solid State Chemistry and its Applications, John Wiley & Sons, 1984.*
Lin et al, TargetingHistone Deacetylase in Cancer Therapy, Medicinal Research Reviews, vol. 26, No. 4, 2006, pp. 397-413.
Marks et al, Histone Deacetylase Inhibitors: Inducers of Differentiation or Apoptosis of Transformed Cells, Journal of the National Cancer Institute, vol. 92, No. 15, 2000, pp. 1210-1216.
Riessland et al, The benzamide M344, a novel histone deacetylase inhibitor, significantly increases SMN2 RNA/protein levels in spinal muscular atrophy cells, Hum Genet, 2006, 120, pp. 101-110.
Minamiyama et al, Sodium butyrate ameliorates phenotypic expression in a transgenic mouse model of spinal and bulbar muscular atrophy, Human Molecular Genetics, 2004, vol. 13, No. 11, pp. 1183-1192.
Alao et al, Histone deacetylase inhibitor, Trichostatin A induces ubiquitin-dependent cyclin D1 degradation in MCF-7 breast cancer cells, Molecular Cancer 2006, 5:8.
Claude Bernard and Judah Folkman: Nothing Makes Sense in Medicine Except in the Light of Biology, FASEB, Editorial, vol. 22, Apr. 2008, pp. 943-946.
McGee et al, AMP-Activated Protein Kinase Regulates GLUT4 Transcription by Phosphorylating Histone Deacetylase 5, Diabetes, vol. 57, Apr. 2008.
Catley et al, NVP-LAQ824 is a potent novel histone deacetylase inhibitor with significant activity against multiple myeloma, Blood, Oct. 1, 2003, vol. 102, No. 7.
George et al, Combination of the histone deacetylase inhibitor LBH589 and the hsp90 inhibitor 17-AAG is highly active against human CML-BC cells and AML cells with activating mutation of FLT-3, Blood, 105(4) pp. 1768-1776.
Office Action dated Nov. 10, 2010 for 2010201322, which is a counterpart Australian application, that cites WO2008/154801, WO2007/018314, and US2004/0235888.
J. Med. Chem. 2009, 52(8), 2465-2481 Published online Mar. 23, 2009.
Synthetic Communications 1980, 10(1), 37-42.

* cited by examiner

*Primary Examiner* — Nizal Chandrakumar
(74) *Attorney, Agent, or Firm* — WPAT, P.C.; Anthony King

(57) ABSTRACT

The invention relates to a compound represented by the following formula (I):

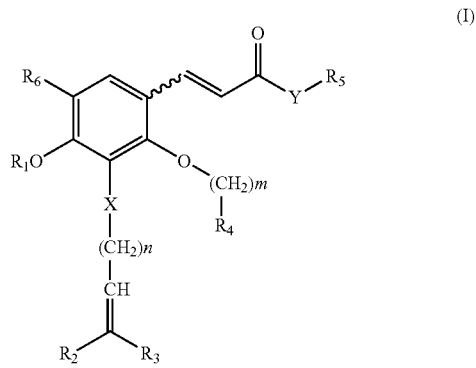

and pharmaceutically acceptable salts, stereoisomers, enantiomers, prodrugs and solvates thereof. The compounds are useful as an agent for enhancing the neurite outgrowth and preventing or treating of diseases associated with HDAC in particular, tumor or cell proliferative diseases. In particular, the compounds of the invention can be used as an agent for anti-cancer, anti-diabetic, and anti-neurodegenerative diseases such as Alzheimer's disease, Huntington's disease, Spinocerebellar Ataxias (SCA), and human spinal muscular atrophy (SMA).

10 Claims, 44 Drawing Sheets

(c)

(a)

(a)

CINAMIC COMPOUNDS AND DERIVATIVES THEREFROM FOR THE INHIBITION OF HISTONE DEACETYLASE

FIELD OF THE INVENTION

The present invention relates to novel cinamic compounds which are useful as agents for the prevention or treatment of diseases associated with histone deacetylase (HDAC). They also can be used as agents for enhancing the neurite outgrowth. In particular, they can be used as agents for anti-cancer, anti-diabetic, or anti-neurodegenerative diseases such as Alzheimer's disease, Huntington's disease, Spinocerebellar Ataxias (SCA) and human spinal muscular atrophy (SMA).

BACKGROUND OF THE INVENTION

Eukaryotic DNA is highly organized and packaged in the nucleus. The organization and packaging are achieved through the addition of proteins, including core histones H2A, H2B, H3 and H4, which form a complex structure, the chromatin, together with DNA. The modification of core histones is of fundamental importance to conformational changes of the chromatin. The level of acetylation is related to transcription activity, and then the acetylation induces an open chromatin conformation that allows the transcription machinery access to promoters. Histone deacetylase (HDAC) and histone acetyltransferase (HAT) are enzymes that influence transcription by selectively deacetylating or acetylating the $\epsilon$-amino groups of lysine located near the amino termini of core histone proteins. HDACs are a family of 18 enzymes (isoforms) that may act as master regulators of many diseases, including cancer, because they are involved in the control of gene expressions. Disruption of HDACs has been linked to a wide variety of human cancers. HDAC enzymes or isoforms appear to be involved in many different types of cancer.

Histone deacetylase (HDAC) inhibitors are emerging as an exciting new class of potential anticancer agents for the treatment of solid and hematological malignancies. In recent years, an increasing number of structurally diverse HDAC inhibitors have been identified; they inhibit proliferation and induce differentiation and/or apoptosis of tumor cells in cultures and in animal models. HDAC inhibition causes acetylated nuclear histones to accumulate in both tumoral and normal tissues, providing a surrogate marker for the biological activity of HDAC inhibitors in vivo. The effects of HDAC inhibitors on gene expression are highly selective, leading to transcriptional activation of certain genes such as the cyclin-dependent kinase inhibitor p21$^{WAF1/CIP1}$ but repression of others. HDAC inhibition results in acetylation of not only histones but also transcription factors such as p53, GATA-1 and estrogen receptor-alpha. The functional significance of acetylation of non-histone proteins and the precise mechanisms whereby HDAC inhibitors induce tumor cell growth arrest, differentiation and/or apoptosis are currently the focus of intensive research. HDAC inhibitors currently in clinical trials have shown activity and represent a class of molecularly targeted anti-tumor agents with potential for efficacy based on a novel mechanism of action.

A review article published in Medicinal Research Reviews, Vol. 26, No. 4, pp. 397-413, 2006 states that four classes of HDAC inhibitors, short-chain fatty acids, hydroxamic acids, benzamides and cyclic peptides, had been reported. Hydroxamic acid-based hybrid polar compounds (HPCs) are HDAC inhibitors, which induce differentiation at micromolar or lower concentrations (Journal of the National Cancer Institute, Vol. 92, No. 15, Aug. 2, 2000, pp. 1210-1216). U.S. Pat. No. 6,174,905, EP 0847992, JP 258863/96, and Japanese Application No. 10138957 disclose that benzamide derivatives induce cell differentiation and inhibit HDAC. SNDX-275 (Entinostat) especially disclosed in Example 48 of U.S. Pat. No. 6,174,905 has become a candidate for cancer treatment drug. WO 01/38322 discloses additional compounds that serve as HDAC inhibitors. It is reported in Hum Genet, 2006, 120, pp. 101-110 that the benzamide M344 up-regulates SMN2 protein expression in fibroblast cells derived from SMA patients up to 7-fold after 64 hours of treatment. It is reported that sodium butyrate ameliorates phenotypic expression in a transgenic mouse model of spinal and bulbar muscular atrophy (Human Molecular Genetics, 2004, Vol. 13, No. 11, pp. 1183-1192). Trichostatin A, a histone deacetylase inhibitor, was found to induce ubiquitin-dependent cyclin D1 degradation in MCF-7 breast cancer cells (Molecular Cancer 2006, 5:8). U.S. Pat. No. 7,169,801 discloses that compounds having the formula of Z-Q-L-M or Z-L-M may be used to inhibit histone deacetylase. U.S. Pat. No. 6,888,027 covers a family of Sulphonamide HDAC inhibitors including PXD101. European Patent Number EP 1 301 184 covers the use of valproic acid and derivatives as HDAC inhibitors in the treatment of solid tumors. WO0222577 indicates that hydroxamate compounds are inhibitors of histone deacetylase and are useful as pharmaceuticals for the treatment of proliferative diseases. Moreover, the anti-diabetic activity of HDAC inhibitors is reported in the FASEB Journal, 2008, Vol. 22, pp. 944-945 and Diabetes, 2008, Vol. 57, pp. 860-867.

N,N'-hexamethylene bisacetamide (HMBA) is an effective inducer of differentiation in a number of transformed cell lines. U.S. Pat. Nos. 6,087,367 and RE38506 reports that a number of compounds related to HMBA with polar groups separated by apolar linkages on a molar basis, are as active or 100 times more active than HMBA. Furthermore, U.S. Pat. No. 7,399,787 reports that histone deacetylase inhibitors related to HMBA such as suberoylanilide hydroxamide acid (SAHA) have the ability to induce growth arrest, differentiation and/or apoptosis of tumor cells. In addition, Laurence Catley et al. reports that NVP-LAQ824 (a hydroxamic acid derivative) and NVP-LAQ824 (a derivative of 4-aminomethylcinnamic hydroxamic acid) are potent histone deacetylase inhibitors (Blood, 1 October 2003, Vol. 102, No. 7, pp. 2615-2622). George P et al. reports that LBH589 induces growth inhibition and regression in tumor cell lines by triggering apoptosis and LBH589 is now being tested in phase I clinical trials as an anticancer agent (Blood 105(4): 1768-76 Feb. 15, 2005). Other histone deacetylase inhibitors known in the art include pyroxamide, M-carboxycinnamic acid bishydroxamide (CBHA), trichostatin A (TSA), trichostatin C, salicylihydroxamic acid (SBHA), azelaic bishydroxamic acid (ABHA), azelaic-1-hydroxamate-9-anilide (AAHA), 6-(3-chlorophenylureido) carpoic hydroxamic acid (3C1-UCHA), oxamflatin, A-161906, scriptaid, PXD-101, cyclic hydroxamic acid-containing peptide (CHAP), ITF-2357, MW2796, MW2996, trapoxin A, FR901228 (FK 228 or Depsipeptide), FR225497, apicidin, CHAP, HC-toxin, WF27082, chlamydocin, sodium butyrate, isovalerate, valerate, 4-phenylbutyrate (4-PBA), 4-phenylbutyrate sodium (PBS), arginine butyrate, propionate, butyramide, isobutyramide, phenylacetate, 3-bromopropionate, tributyrin, valproic acid, valproate, CI-994, 3'-amino derivative of MS-27-275, MGCD0103 and Depudecin (U.S. Publication No. 20080242648).

However, there is still a need to develop a new class of HDAC inhibitors to prevent or treat cancers and other diseases involving HDAC.

SUMMARY OF THE INVENTION

The object of the invention is to provide a group of compounds represented by the following formula (I):

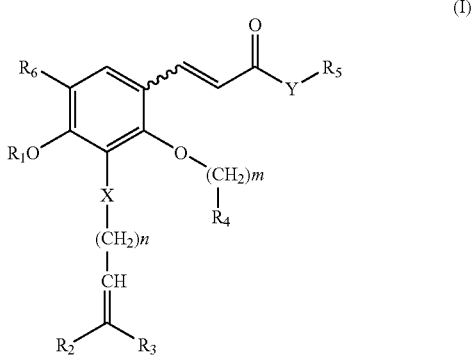

(I)

and pharmaceutically acceptable salts, stereoisomers, enantiomers, prodrugs and solvates thereof. The compounds are useful as an agent for enhancing the neurite outgrowth and preventing or treating diseases associated with HDAC

BRIEF DESCRIPTION OF THE DRAWINGS

FIG. 1(c) shows the results of a flow analysis of A549 treated with various concentrations of NBM-HB-OS01 for 24 hrs. FIG. 1(d) shows that NBM-HB-OS01 increased p21 gene expression. Rat C6 glioma cells were treated with NBM-HB-OS01 for 48 hrs and GAPDH served as an internal control. FIG. 1(e) shows the results of treatment of Rat C6 glioma cells with various concentrations of NBM-HB-OS01 for 72 hrs. Accumulation of hyperacetylated histone H3, hyperacetylated histone H4 and p21 was detected in a dose-dependent manner by western blotting. FIG. 1(f) shows the results of treatment of Rat C6 glioma cells with 10 μg/mL NBM-HB-OS01 for 1, 2, 3 and 4 hrs. The accumulation of acetylated H3, acetylated H4, acetylated-tubulin and p21 was seen in a dose-dependent manner. β-actin was the internal control. FIG. 1(g) shows the results of treatment of Human breast cancer MCF-7 (Estrogen Receptor positive) cells with 10 μg/mL NBM-HB-OS01 for 24 hrs. Overexpression of Gelsolin protein was observed.

FIG. 2(d) shows the results of treatment of MCF-7 cells with 10 μg/mL NBM-C-BX-OS01 for 1, 2, 3 and 4 hrs. The expression of acetylated H3, acetylated H4, acetylated-tubulin, and p21 increased in a dose-dependent manner. β-actin was the internal control. FIG. 2(e) shows the results of treatment of Rat C6 glioma cells with NBM-C-BX-OS01 of 7.5 μg/mL for 6 hrs. Overexpression of acetylated tubulin protein was observed.

FIG. 5(a) shows that NBM-C-BA-OS01 (5 μg/mL), NBM-C-BCX-OS01 (4d) (2.5, 5.0 μg/mL), and NBM-C-BMX-OS01 (4b) (2.5, 5.0 μg/mL) inhibited the cell growth of Rat C6 glioma cells in 24 hrs. FIG. 5(b) shows that treatment of NBM-C-BX-OS01 (7.5 μg/mL), NBM-C-BCX-OS01 (2.5, 5.0, 7.5 μg/mL) and NBM-C-BMX-OS01 (2.5, 5.0, 7.5 μg/mL) for 72 hrs induced A549 cells growth inhibition in a dose-dependent manner. Similar results can be seen in treatment of Rat C6 glioma cells with NBM-C-BCX-OS01 and NBM-C-BMX-OS01 of various concentrations for 24 hrs, as shown in FIG. 5(c). FIG. 5(d) shows the results of treatment of Human glioma Hs683 cells with NBM-C-BX-OS01 (1.25, 2.5, 5.0 μg/mL) for 72 hrs and in FIG. 5(e) shows the results of treatment of Human glioblastoma 05-MG cells with NBM-C-BCX-OS01 (1.0, 2.0, 4.0 μg/mL), and NBM-C-BMX-OS01 (1.0, 2.0, 4.0 μg/mL) for 72 hrs. Cell growth inhibition was observed. The treated cells counted by a trypan blue exclusion assay are plotted in FIG. 5(f).

As shown in FIG. 6(a), inhibition of the cell growth of human breast cancer MDA-MB-231 cells was observed after treating the cells with various concentrations of NBM-C-BCX-OS01, NBM-C-BMX-OS01, and NBM-C-BFX-OS01 (4c) for 72 hrs. The NBM-HB-OS01 derivatives significantly inhibited the growth of human breast cancer MDA-MB-231 cells. The treated cells counted by a trypan blue exclusion assay are shown in FIG. 6(b). FIGS. 6(c) and (d) shows the results of treatment of Human lung cancer A549 cells and Human glioblastoma 05-MG cells with NBM-C-BCX-OS01 and NBM-C-BMX-OS01 for 72 hrs, respectively. FIG. 6(e) shows that NBM-C-BCX-OS01 arrested the growth of Human glioma Hs683 cells. Human glioma Hs683 cells were treated with NBM-C-BCX-OS01 (1.0, 2.0, 4.0 μg/mL) for 72 hrs.

As shown in FIG. 7(a), the induction of acetylated Hsp90 and gelsolin proteins was detected in a dose-dependent manner, i.e., Hsp90 and CTPS proteins decreased in a dose-dependent manner. It can be observed in FIG. 7(b) that the expression of p21, acetylated tubulin, acetylated Histone H3, and acetylated Histone H4 was significantly increased in a dose-dependent manner. SAHA was used as a positive control and β-actin as an internal control.

DETAILED DESCRIPTION OF THE INVENTION

Figure 1:
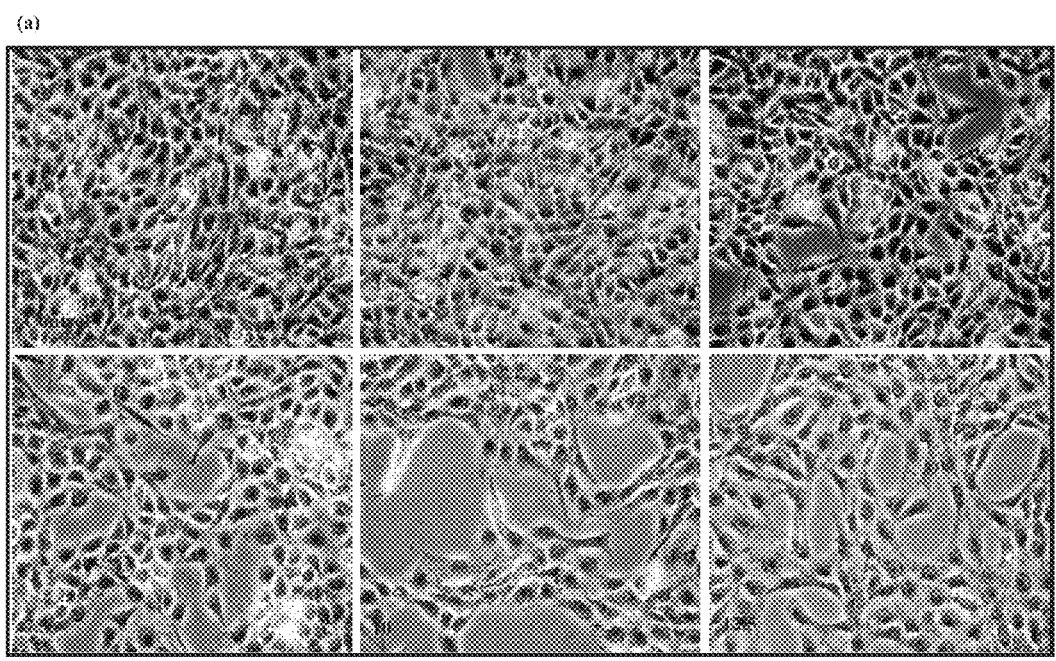
FIG. 1 shows the effects of NBM-HB-OS01(2h) on the inhibition of cells growth of various cancer cell lines. Inhibition of cancer cells was shown in Rat C6 glioma cells and Human colon cancer HT-29 cells after they were treated with various concentrations of NBM-HB-OS01 for 48 hrs and the results are shown in FIGS. 1(a) and (b), respectively.
Figure 1:
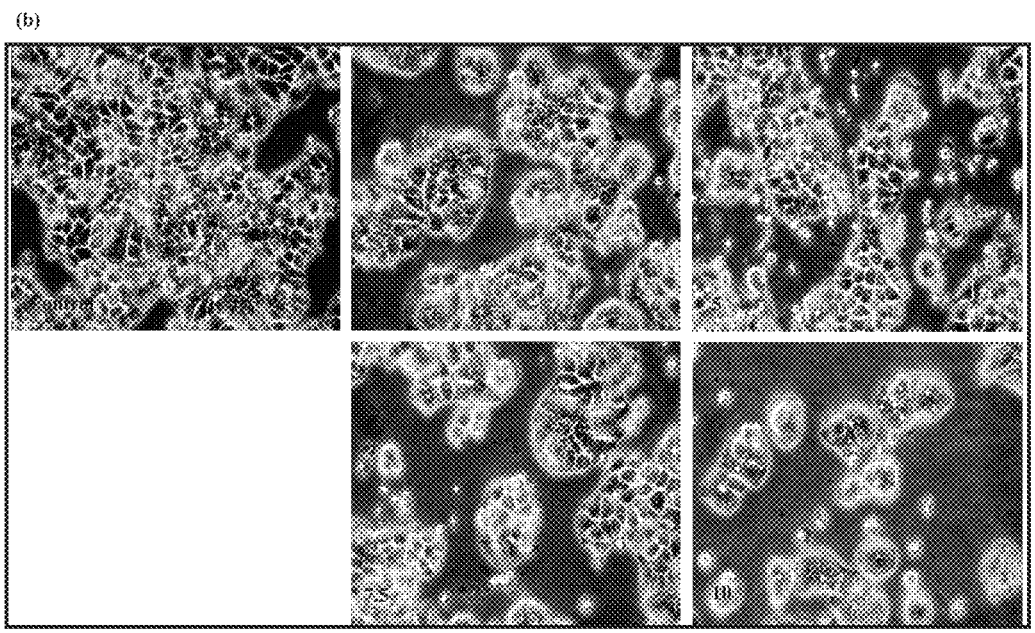
Figure 1:
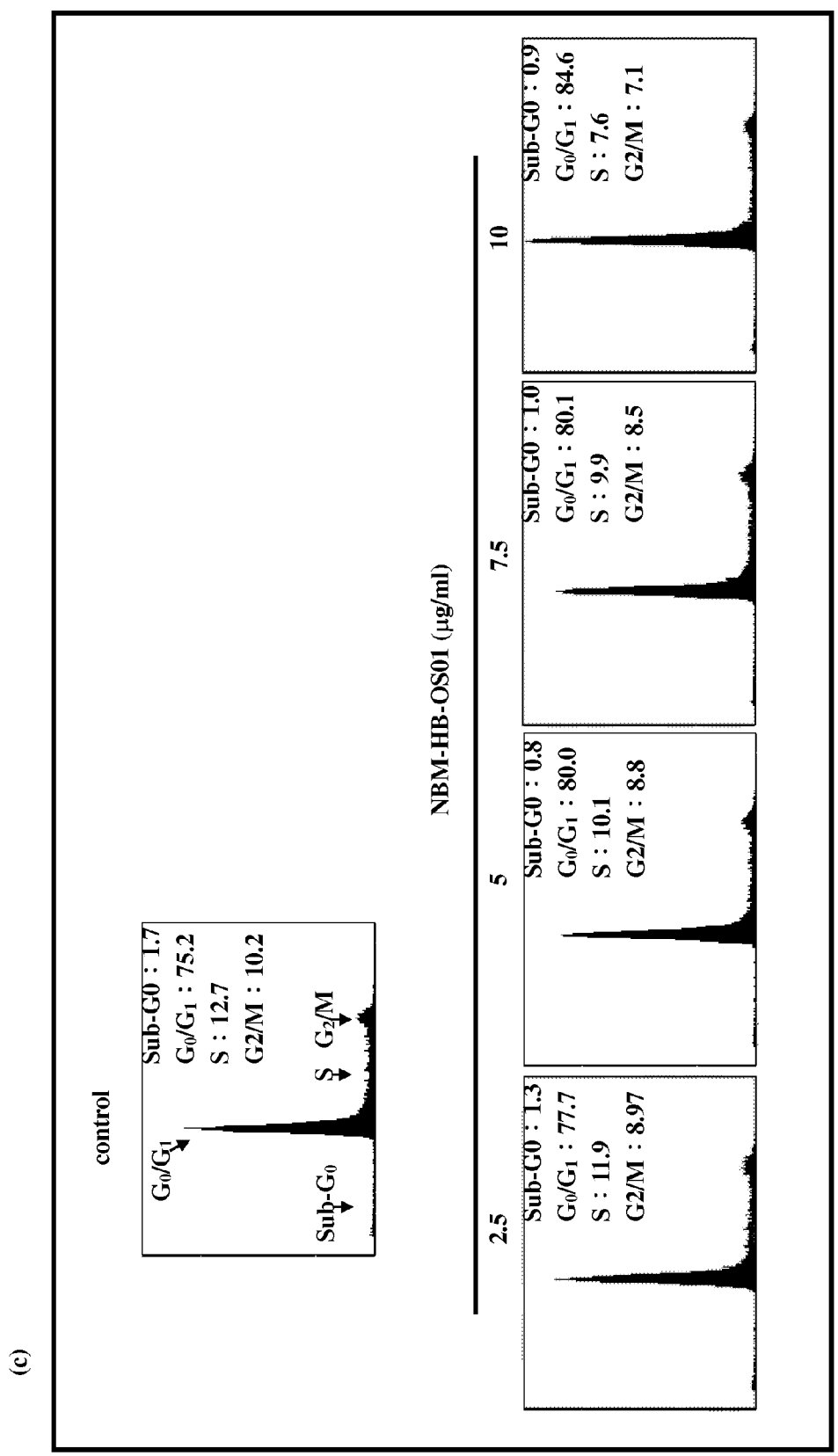
Figure 1:
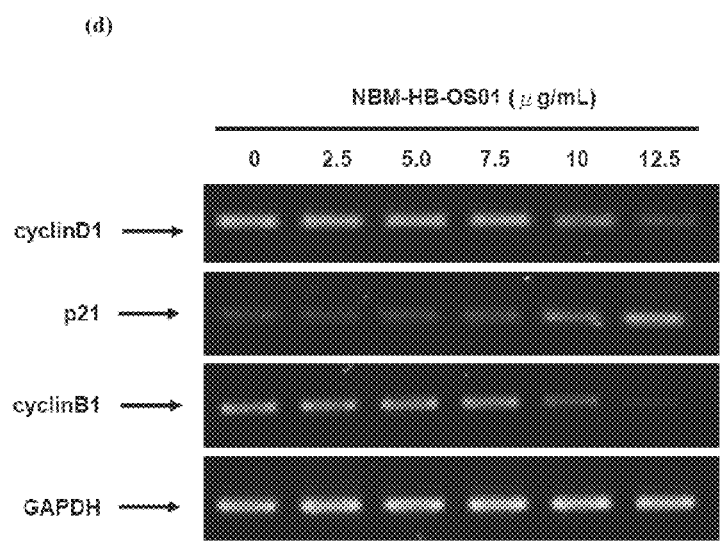
Figure 1:
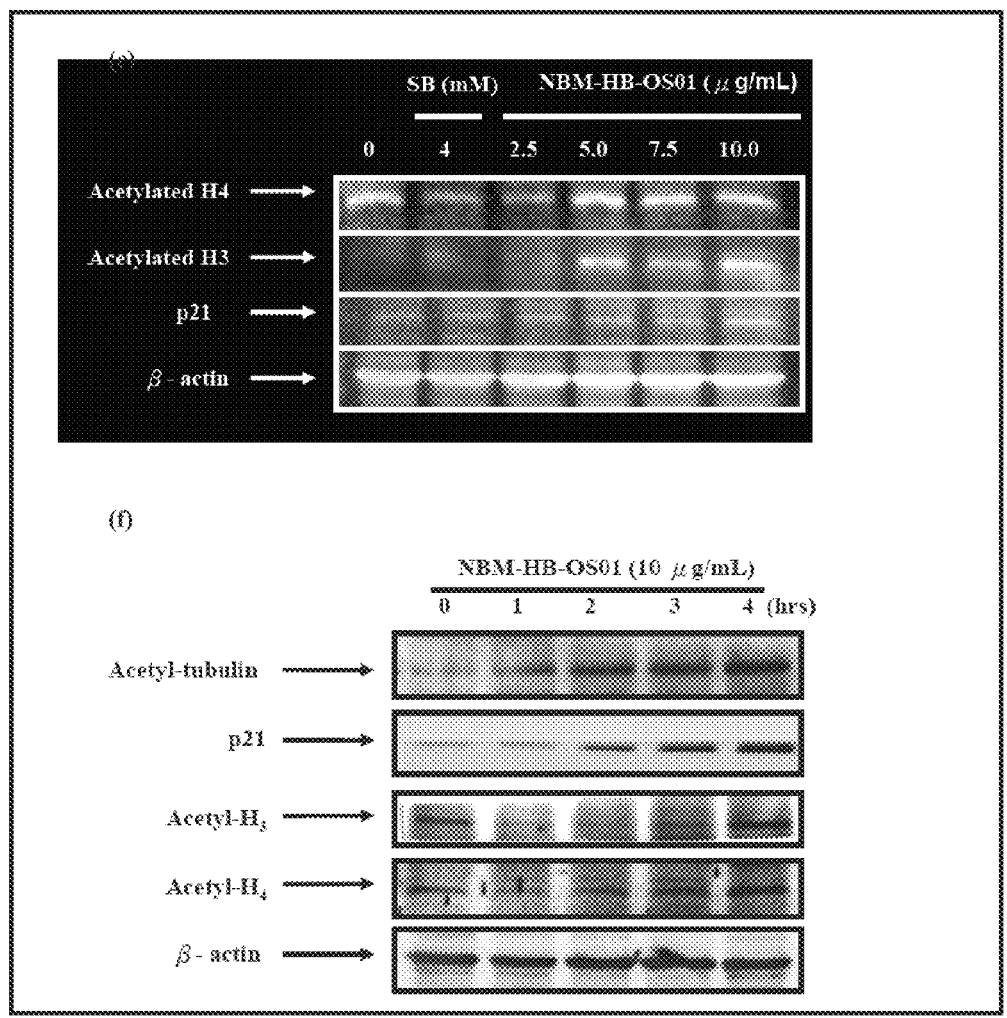
Figure 1:
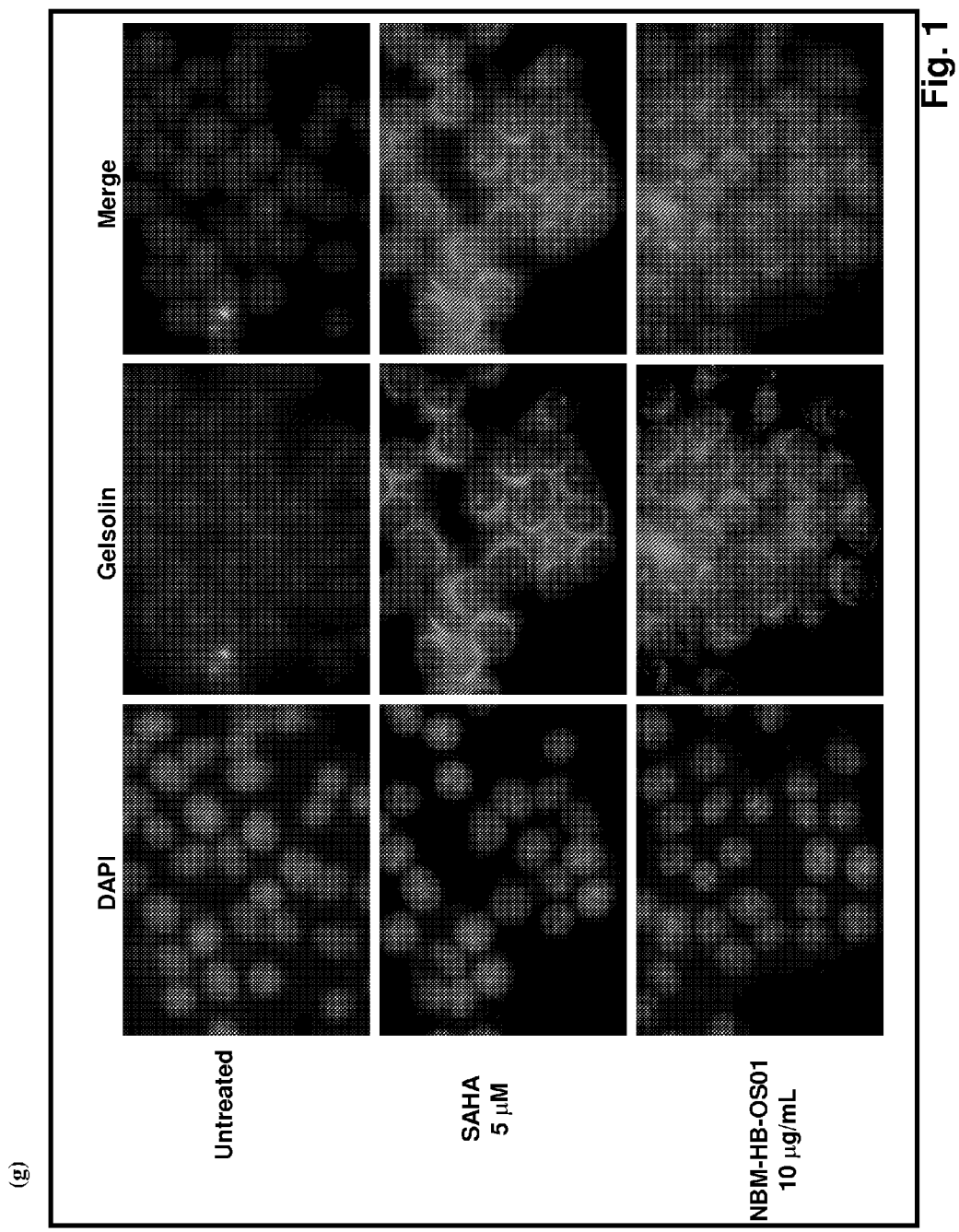

The present invention relates to novel cinamic derivatives, which are useful as agents for enhancing the neurite outgrowth and preventing and treating of diseases associated with HDAC, in particular, neurodegenerative diseases, stroke, diabetic, tumor or other cell proliferative diseases. The compounds of the invention are potent in inhibiting growth in cancer cells via differentiation pathway. In particular, they can be used as agents for anti-neurodegenerative diseases such as: Alzheimer's disease, Huntington's disease, Spinocerebellar Ataxias (SCA), and human spinal muscular atrophy (SMA).

Compounds of the Invention

Accordingly, the present invention relates to compounds represented by the following formula (I):

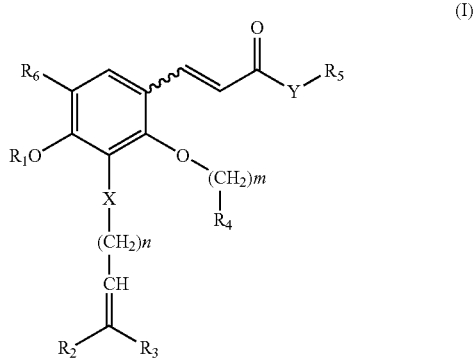

(I)

wherein $R_1$ is hydrogen, alkyl, alkenyl, $C_{5-6}$ cycloalkyl, 5-membered or 6-membered unsaturated carbocycle or 5-membered or 6-membered heterocycle;

X is C, O, N or S;

Y is O, NH or O—$C_{1-4}$alkyl;

n is an integer of 0 to 10;

m is an integer of 0 to 5;

$R_2$ and $R_3$ is independently $C_{1-6}$ alkyl;

$R_4$ is $C_{5-6}$ cycloalkyl or 5-membered or 6-membered unsaturated carbocycle or heterocycle which may be substituted with halogen, $CF_3$, $OR_7$ or $NR_7R_8$, wherein $R_7$ and $R_8$ are independently hydrogen or $C_{1-6}$ alkyl;

$R_5$ is OH, $NH_2$ or $C_{5-6}$ cycloalkyl, 5-membered or 6-membered unsaturated carbocycle or heterocycle wherein the cycloalkyl, carbocycle and heterocycle may be optionally substituted with halogen, $NH_2$, $NO_2$, $C_{1-6}$ alkoxy, $C_{1-6}$ alkylthio, $OR_7$, $NR_7R_8$ or $CF_3$; and $R_6$ is H, $C_{1-10}$alkyl which may be substituted by hydroxy or $C_{2-10}$alkenyl, or together with $R_1$ being —$C_2H_2$—;

and pharmaceutically acceptable salts, stereoisomers, enantiomers, prodrugs and solvates thereof.

In the context of the present specification, the term "alkyl" means straight or branched hydrocarbon chains. The alkyl is preferably $C_{1-10}$ alkyl. Preferably, the carbon number of alkyl is selected from the group consisting of 1 to 8; more preferably, it is $C_{1-6}$ alkyl or $C_{1-4}$ alkyl. Examples of alkyl groups include methyl (—$CH_3$), ethyl (—$CH_2CH_3$), propyl (—$CH_2CH_2CH_3$), isopropyl ($CH_3)_2CH$ and butyl (—$C_4H_9$).

In the context of the present specification, the term "alkenyl" means both straight and branched chain unsaturated hydrocarbon groups, wherein the unsaturation is present only as double bonds. According to the invention, the alkenyl includes one or more double bonds. The alkenyl is preferably $C_{2-16}$ alkenyl. More preferably, the carbon number of alkenyl is selected from the group consisting of 2 to 12. Examples of alkenyl groups include ethenyl (—CH=$CH_2$), propenyl (—CH=$CHCH_3$ or —$CH_2$CH=$CH_2$), butenyl (—$CH_2$CH=$CHCH_3$ or —CH=$CHCH_2CH_3$ or —$CH_2CH_2$CH=$CH_2$), —$CH_2$CH=$C(CH_3)CH_3$, —$CH_2$—CH=CH—$CH_2$—$CH_2$—CH=CH—$CH_3$ and —$CH_2$—CH=$C(CH_3)$—$CH_2$—$CH_2$—CH=$C(CH_3)$—$CH_3$.

In the context of the present specification, the term "cycloalkyl" means an aliphatic ring (saturated carbocyclic ring). Preferably, the carbon number of cycloalkyl is selected from the group consisting of 3 to 8. More preferably, the carbon number of cycloalkyl is selected from the group consisting of 5 to 6. Examples of cycloalkyl groups include cyclopropyl, cyclobutyl, cyclopentyl and cyclohexyl.

In the context of the present specification, the term "unsaturated carbocycle" includes a cyclic substituent consisting of carbon atom and hydrogen atom, and the cyclic part is unsaturated cycle, for example, aryl or cycloalkenyl or the like. The term "cycloalkenyl" includes alkenyl which is the cycloalkyl having one or more double bond, for example, cyclopropenyl (e.g., 1-cyclopropenyl), cyclobutenyl (e.g., 1-cyclobutenyl), cyclopentenyl (e.g., 1-cyclopenten-1-yl, 2-cyclopenten-1-yl, and 3-cyclopenten-1-yl), cyclohexenyl (e.g., 1-cyclohexen-1-yl, 2-cyclohexen-1-yl, and 3-cyclohexen-1-yl), cycloheptenyl (e.g., 1-cycloheptenyl), cyclooctenyl (e.g., 1-cyclooctenyl) or the like. Especially, preferred is 1-cyclohexen-1-yl, 2-cyclohexen-1-yl, or 3-cyclohexen-1-yl. The term "aryl" includes single and fused rings wherein at least one ring is aromatic, for example, phenyl, naphthyl and tetrahydronaphthalenyl.

In the context of the present specification, the phrase "5-membered or 6-membered heterocycle" refers to a cyclic ring of five or six atoms, wherein at least one atom of the ring is a heteroatom. The 5-membered or 6-membered heterocycle can be aromatic or non-aromatic which is saturated or unsaturated. Preferably, the heteroatom is selected from N, O and S. Examples of heterocycle includes, but not limited to, furyl (e.g., 2-furyl, 3-furyl), thienyl (e.g., 2-thienyl, 3-thienyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazolyl (e.g., 1,2,4-triazol-1-yl, 1,2,4-triazol-3-yl, 1,2,4-triazol-4-yl)tetrazolyl (e.g., 1-tetrazolyl, 2-tetrazolyl, 5-tetrazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), thiazolyl (e.g., 2-thiazolyl, 4-thiazolyl, 5-thiazolyl), thiadiazolyl, isothiazolyl (e.g., 3-isothiazolyl, 4-isothiazolyl, 5-isothiazolyl), pyridyl (e.g., 2-pyridyl, 3-pyridyl, 4-pyridyl), pyridazinyl (e.g., 3-pyridazinyl, 4-pyridazinyl)pyrimidinyl (e.g., 2-pyrimidinyl, 4-pyrimidinyl, 5-pyrimidinyl), furazanyl (e.g., 3-furazanyl), pyrazinyl (e.g., 2-pyrazinyl), oxadiazolyl (e.g., 1,3,4-oxadiazol-2-yl), 1-pyrrolinyl, 2-pyrrolinyl, 3-pyrrolinyl, pyrrolidino, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidyl, 3-piperidyl, 4-piperidyl, piperazino, 2-piperazinyl, 2-morpholinyl, 3-morpholinyl, morpholino, tetrahydropyranyl or the like.

In the context of the present specification, the term "halogen" means fluorine, chlorine, bromine and iodine.

In the context of the present specification, the term "pharmaceutically acceptable salt" includes those formed with both organic and inorganic acids and bases. Pharmaceutically acceptable acid addition salts include those formed from mineral acids such as: hydrochloric, hydrobromic, sulphuric, and phosphoric, acid; and organic acids such as: citric, tartaric, lactic, pyruvic, acetic, trifluoroacetic, succinic, oxalic, formic, fumaric, maleic, oxaloacetic, methanesulphonic, ethanesulphonic, p-toluenesulphonic, benzenesulphonic and isethionic acids. Pharmaceutically acceptable base salts include ammonium salts, alkali metal salts such as those of sodium and potassium, alkaline earth metal salts such as those of calcium and magnesium and salts with organic bases, including salts of primary, secondary and tertiary amines.

In the context of the present specification, the term "prodrug" means a compound which is converted within the body, e.g., by hydrolysis in the blood, into its active form that has medical effects.

In the context of the present specification, the term "solvate" means a complex comprising the compound of the invention and a solvent in which they are reacted or from which they are precipitated or crystallized.

In the context of the present specification, the term "stereoisomers" are isomeric molecules whose atomic connectivity is the same but whose atomic arrangement in space is different.

In the context of the present specification, the term "enantiomers" are stereoisomers that are nonsuperimposable complete mirror images of each other, much as one's left and right hands are "the same" but opposite.

According to the invention, the preferred compound of formula (I) of the invention is selected from the group consisting of the following:

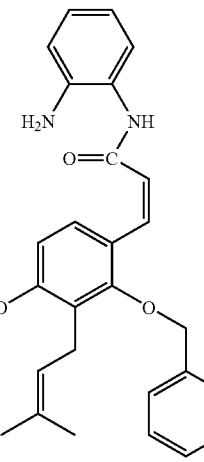

NBM-C-BA-OS01 (17a)

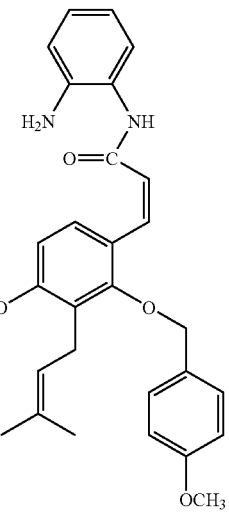

NBM-C-BMA-OS01 (17b)

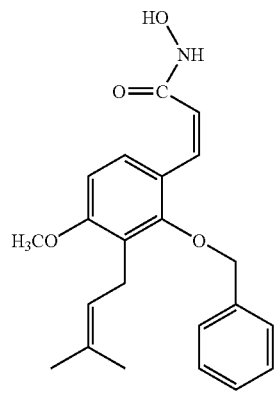

NBM-C-BX-OS01 (4a)

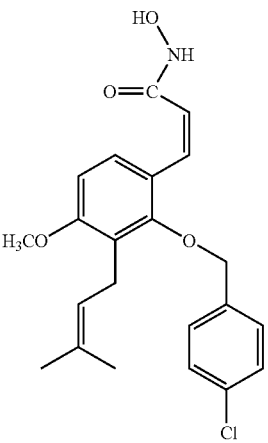

NBM-C-BCX-OS01 (4d)

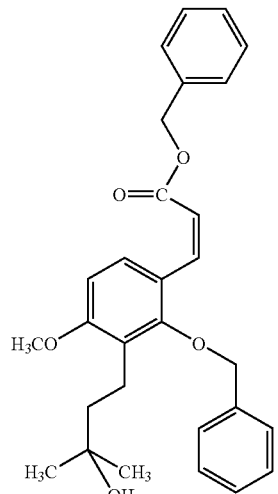

NBM-HB-OS01 (2h)

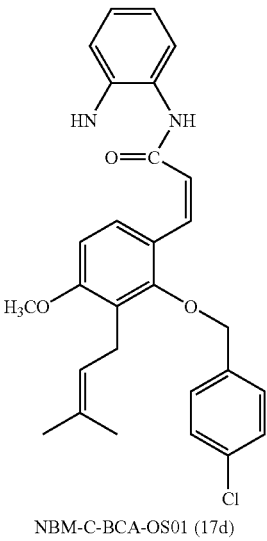

NBM-C-BCA-OS01 (17d)

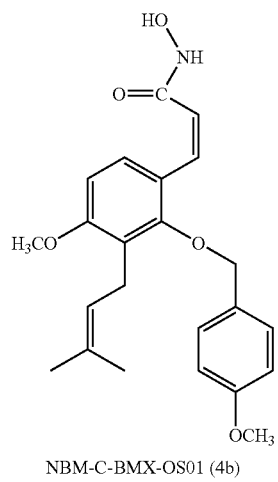

NBM-C-BMX-OS01 (4b)

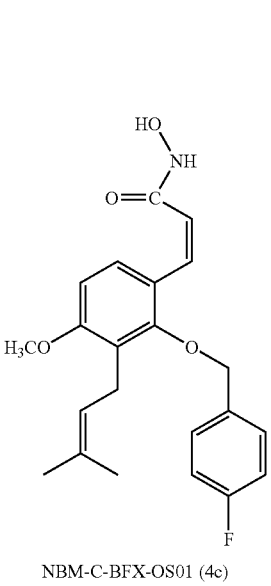

NBM-C-BFX-OS01 (4c)

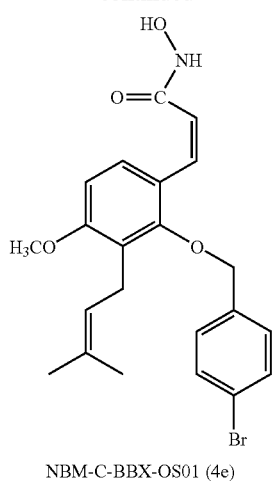
NBM-C-BBX-OS01 (4e)
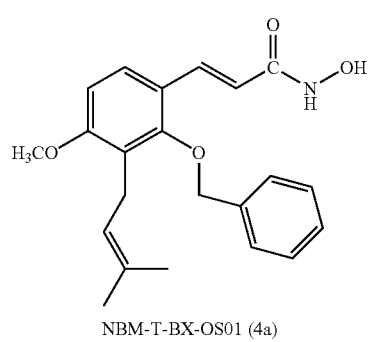
NBM-T-BX-OS01 (4a)
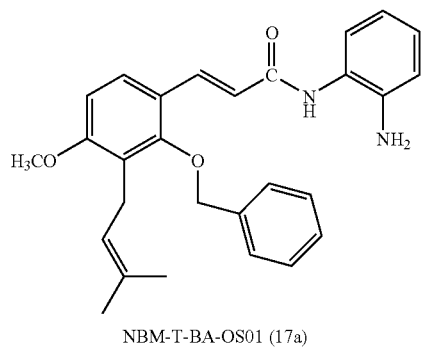
NBM-T-BA-OS01 (17a)
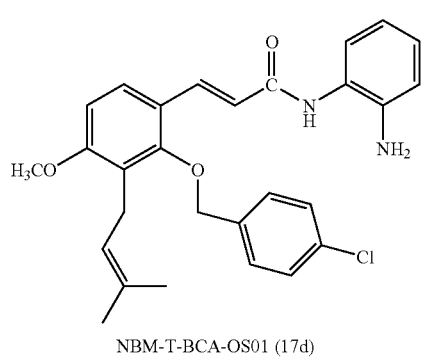
NBM-T-BCA-OS01 (17d)
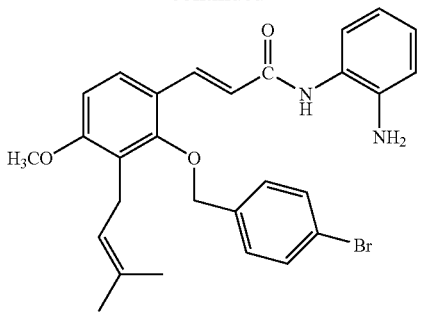
NBM-T-BBA-OS01 (17e)
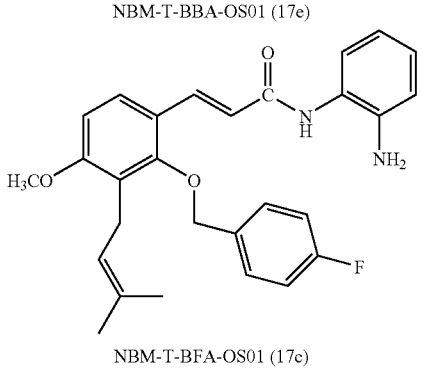
NBM-T-BFA-OS01 (17c)
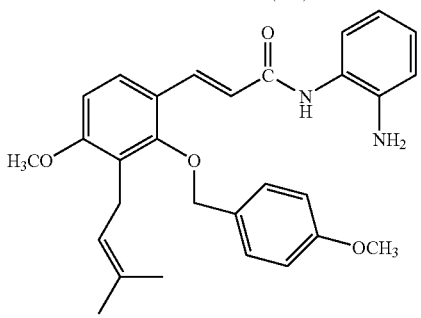
NBM-T-BMA-OS01 (17b)
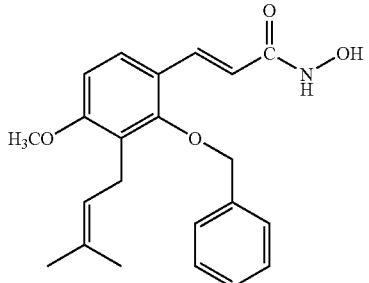
NBM-T-BCX-OS01 (4d)
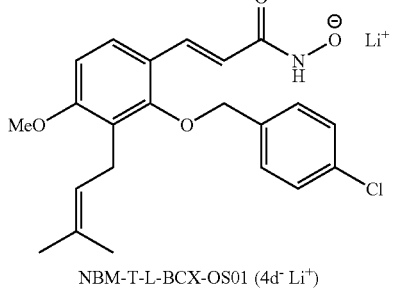
NBM-T-L-BCX-OS01 (4d$^-$ Li$^+$)

-continued
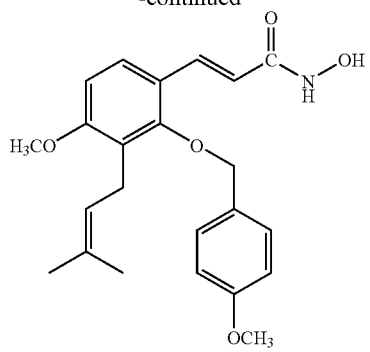
NBM-T-BMX-OS01 (4b)
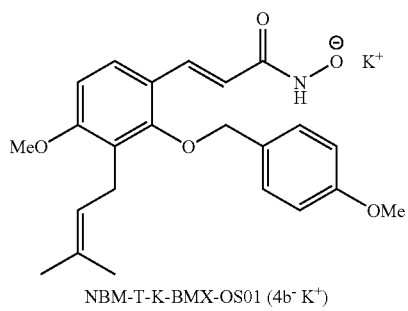
NBM-T-K-BMX-OS01 (4b⁻ K⁺)
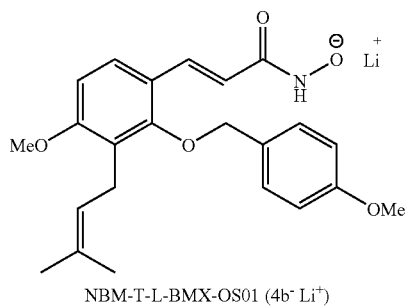
NBM-T-L-BMX-OS01 (4b⁻ Li⁺)
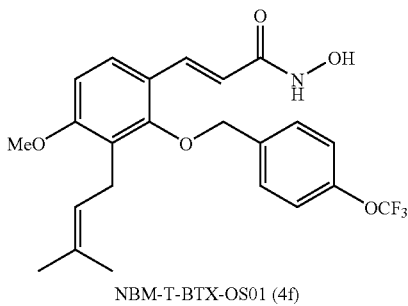
NBM-T-BTX-OS01 (4f)
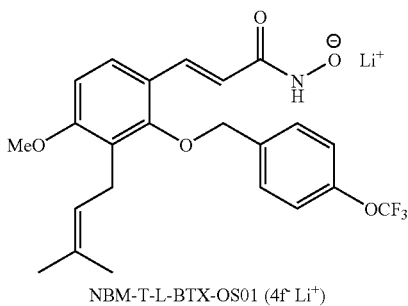
NBM-T-L-BTX-OS01 (4f⁻ Li⁺)
-continued
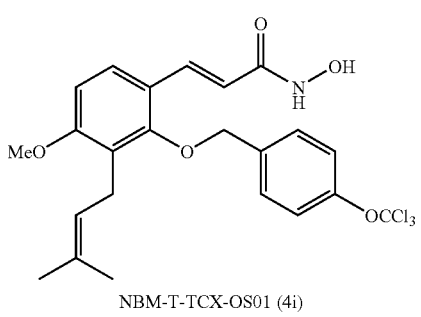
NBM-T-TCX-OS01 (4i)
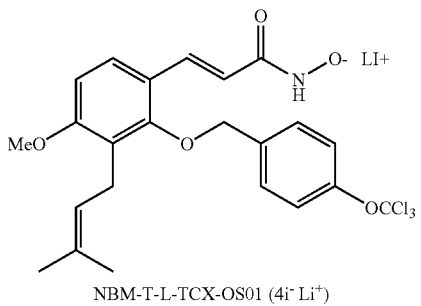
NBM-T-L-TCX-OS01 (4i⁻ Li⁺)
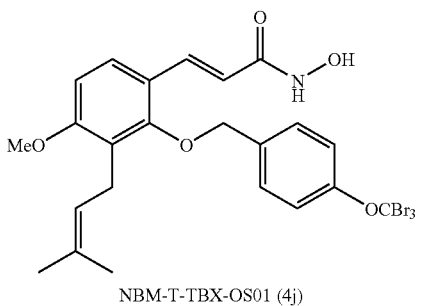
NBM-T-TBX-OS01 (4j)
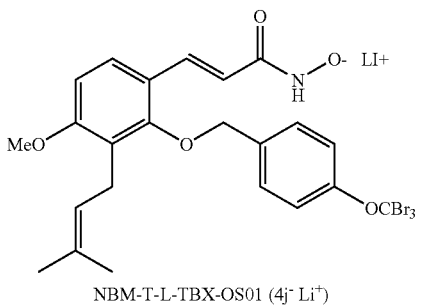
NBM-T-L-TBX-OS01 (4j⁻ Li⁺)
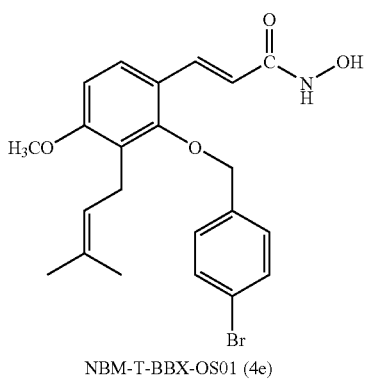
NBM-T-BBX-OS01 (4e)

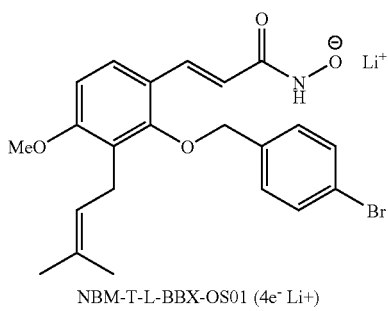
NBM-T-L-BBX-OS01 (4e⁻ Li+)
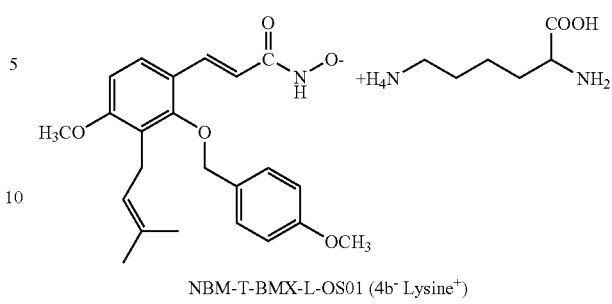
NBM-T-BMX-L-OS01 (4b⁻ Lysine+)
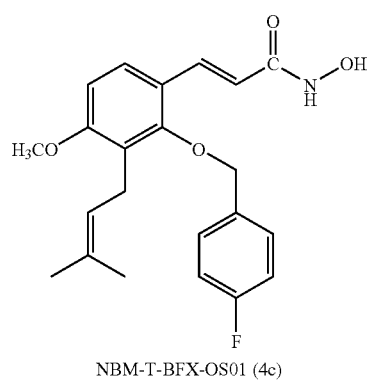
NBM-T-BFX-OS01 (4c)
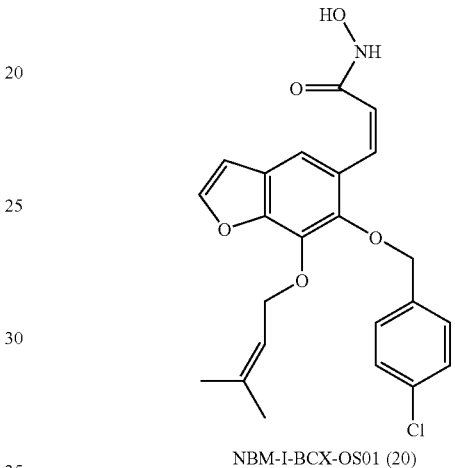
NBM-I-BCX-OS01 (20)
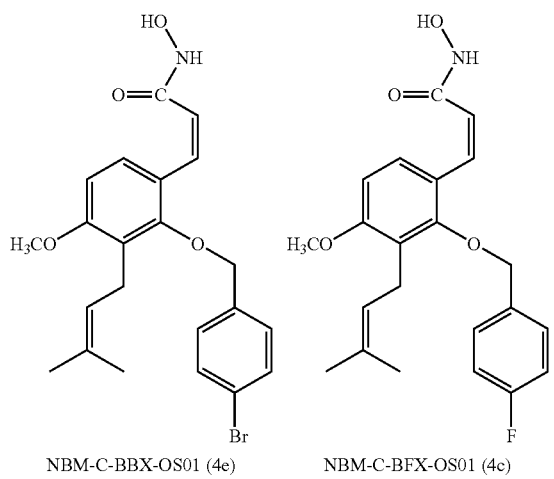
NBM-C-BBX-OS01 (4e)   NBM-C-BFX-OS01 (4c)
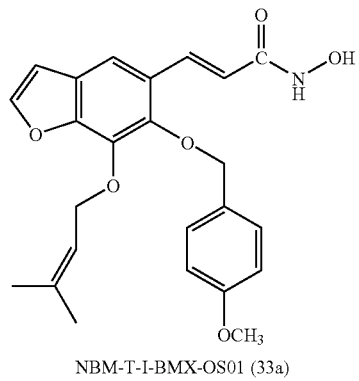
NBM-T-I-BMX-OS01 (33a)
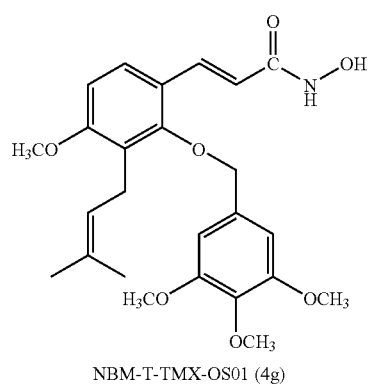
NBM-T-TMX-OS01 (4g)
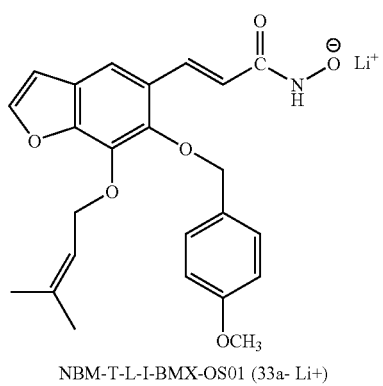
NBM-T-L-I-BMX-OS01 (33a- Li+)

-continued

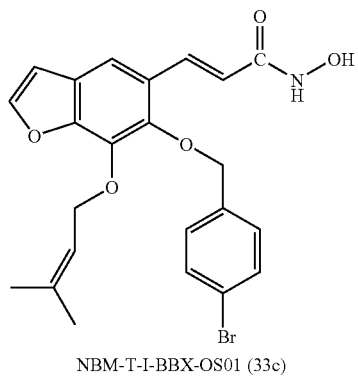

NBM-T-I-BBX-OS01 (33c)

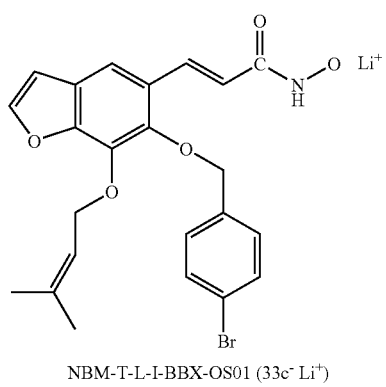

NBM-T-L-I-BBX-OS01 (33c⁻ Li⁺)

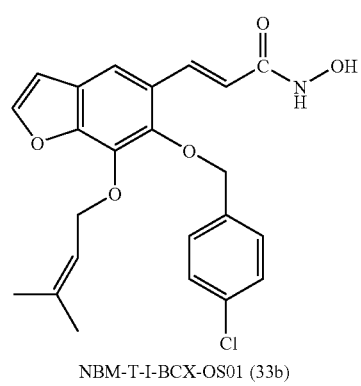

NBM-T-I-BCX-OS01 (33b)

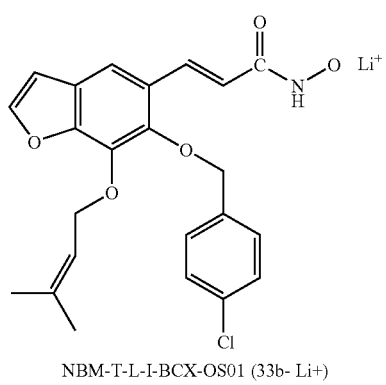

NBM-T-L-I-BCX-OS01 (33b- Li+)

-continued

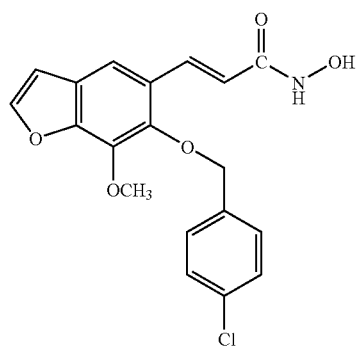

NBM-T-I-MCX-OS01 (26b)

According to the invention, the compounds of formula (I) of the invention can inhibit HDAC and thus can be used as agents for the prevention or treatment of diseases associated with histone deacetylase (HDAC). In addition, the compounds of the invention significantly inhibit growth of multiple cancer cell lines, including those of rat C6 glioma, human glioblastoma, human breast cancer cells, human leukemia cells, and human melanoma cells. The mechanism for inhibiting the growth of cancer cells may be via differentiation pathway, in particular via induced differentiation and regulated cell cycle regulator gene expression, including those of p21 and cyclin B1. In addition, the compounds of formula (I) of the invention can mediate neuronal differentiation of neural stem cells and thus can be used as agents against stroke and anti-neurodegenerative diseases such as Huntington's disease and poly-glutamine disease. These compounds also can be used to enhance long-term memory. In addition, the compounds of formula (I) of the invention can control whole-body energy balance through the regulation of GLUT4 transcription and therefore provide new therapeutic targets for the treatment of Type 2 diabetes.

For the therapeutic uses of the compounds of the invention, the dosage administered will, of course, vary with the compound employed, the mode of administration, the treatment desired and the disorder indicated. The daily dosage of the compound of formula (I) may be in the range from 1 mg/kg to 20 mg/kg. The invention provides the methods of inhibiting HDAC, treating tumor or cell proliferative disease, stroke, diabetic, or neurodegenerative diseases such as Alzheimer's disease, Huntington's disease, Spinocerebellar Ataxias (SCA) and human spinal muscular atrophy (SMA) and enhancing the neurite outgrowth in a subject, comprising administrating to the subject a therapeutically effective amount of the compounds of the invention, respectively.

General Synthesis of the Compounds of Formula I of the Invention

The compounds of the present invention can be prepared by any conventional means. Suitable processes for synthesizing these compounds are provided in the examples. Generally, compounds of formula (I) can be prepared according to one of the described synthetic schemes below:

Scheme 1

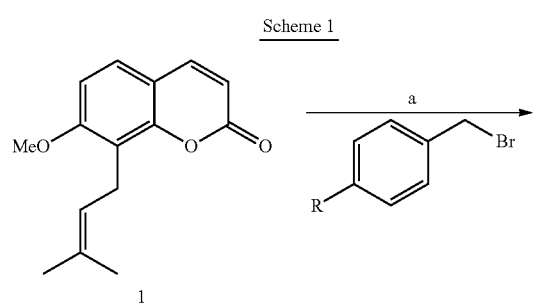

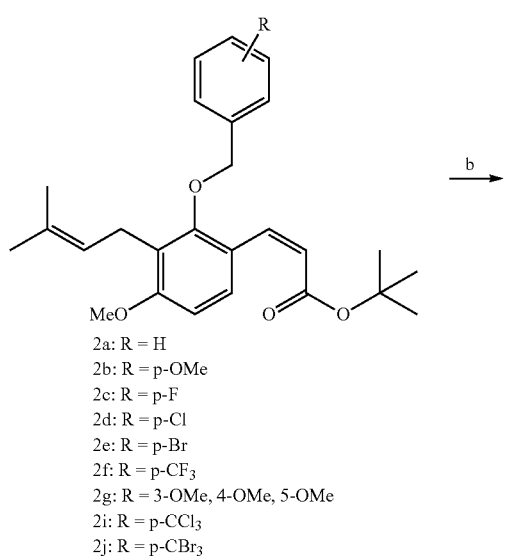

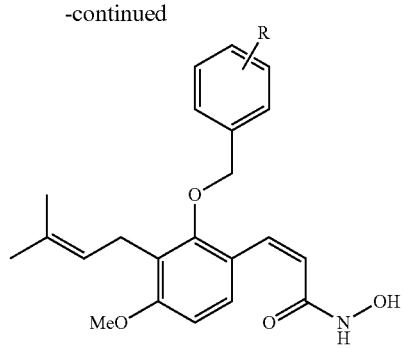

4a: R = H
4b: R = p-OMe
4c: R = p-F
4d: R = p-Cl
4e: R = p-Br
4f: R = p-CF₃
4g: R = 3-OMe, 4-OMe, 5-OMe
4i: R = p-CCl₃
4j: R = p-CBr₃

Reagents and conditions: (a)t-BuOK, DMF, rt; (b)KOH, MeOH, Δ; (c)NH₂OH, ClCO₂Et, EtOH

Scheme 1-1

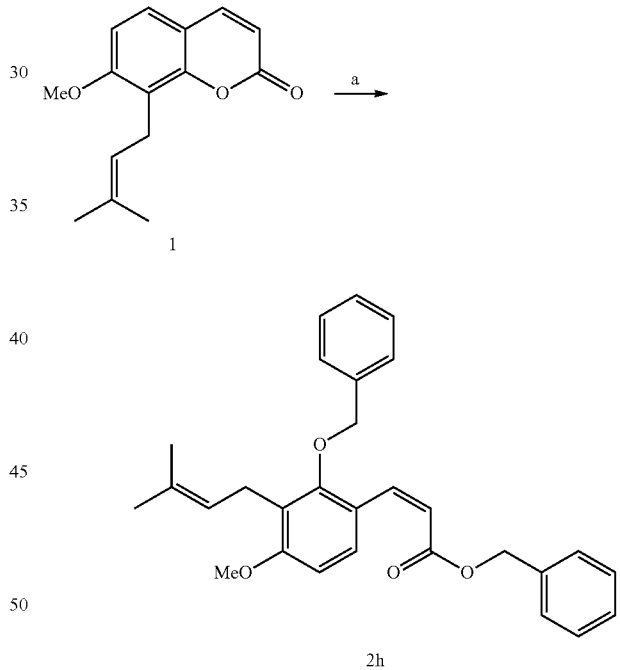

Reagents and conditions: (a)t-BuOK, DMF, 90° C.

General Procedure for the Preparation of 2

To the mixture of 1 (2 g, 8.20 mmol) and potassium t-butoxide (1.84 g, 16.4 mmol) in dry DMF (20 mL) was added various benzyl chlorides (16.4 mmol), the resulting solution was stirred at room temperature under nitrogen for 6 h and then diluted with EtOAc (50 mL), washed with dis-H₂O (25 mL×3) and dried over Na₂SO₄. After removal of EtOAC under reduced pressure, the residue was purified by silica gel (EtOAc:n-Hexane=1:10~1:1) to give 2.

2h can be prepared by a similar procedure with reaction temperature of 90° C.

2a: R = H
2b: R = p-OMe
2c: R = p-F
2d: R = p-Cl
2e: R = p-Br
2f: R = p-CF₃
2g: R = 3-OMe, 4-OMe, 5-OMe
2i: R = p-CCl₃
2j: R = p-CBr₃

3a: R = H
3b: R = p-OMe
3c: R = p-F
3d: R = p-Cl
3e: R = p-Br
3f: R = p-CF₃
3g: R = 3-OMe, 4-OMe, 5-OMe
3i: R = p-CCl₃
3j: R = p-CBr₃

(Z)-2-Benzoxy-3-prenyl-4-methoxy-t-butylcinamate (2a)

$^1$H-NMR (500 MHz, CDCl$_3$): δ 7.50 (1H, d, J=8.7 Hz), 7.43-7.32 (5H, m), 7.06 (1H, d, J=12.4 Hz), 6.67 (1H, d, J=8.7 Hz), 5.82 (1H, d, J=12.4 Hz), 5.15 (1H, t, J=6.5 Hz), 4.82 (2H, s), 3.84 (3H, s), 3.35 (2H, d, J=6.7 Hz), 1.70 (3H, s), 1.65 (3H, s), 1.44 (9H, s). (cis)

(Z)-2-(4-Methoxybenzoxy)-3-prenyl-4-methoxy-t-butyl cinamate (2b)

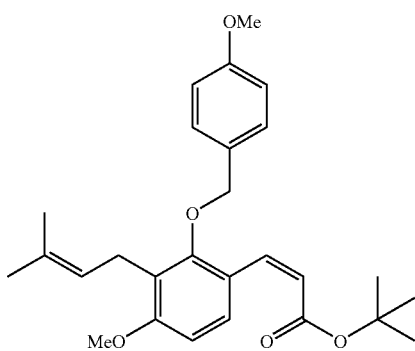

$^1$H-NMR (500 $^{MHz}$, CDCl$_3$): δ 7.50 (1H, d, J=8.6 Hz), 7.35-7.30 (2H, m), 7.06 (1H, d, J=12.3 Hz), 6.90 (2H, d, J=8.4 Hz), 6.67 (1H, d, J=8.6 Hz), 5.83 (1H, d, J=12.4 Hz), 5.15 (1H, t, J=6.5 Hz), 4.76 (2H, s), 3.86 (3H, s), 3.82 (3H, s), 3.34 (2H, d, J=6.6 Hz), 1.71 (3H, s), 1.65 (3H, s), 1.44 (9H, s). (cis)

(Z)-2-Benzoxy-4-methoxy-3-(2-Hydroxy-2-methyl-butyl)benzyl cinamate (2h)

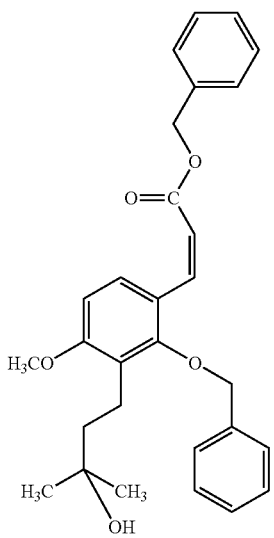

1H-NMR (500 MHz, CDCl3): δ 7.35 (1H, d, J=8.6 Hz), 7.25-7.12 (10H, m), 7.01 (1H, d, J=12.3 Hz), 6.45 (1H, d, J=8.6 Hz), 5.77 (1H, d, J=12.3 Hz), 4.98 (2H, s), 4.66 (2H, s), 3.68 (3H, s), 1.47 (2H, m), 1.04 (6H, s)

General Procedure for the Preparation of 3

The mixture of 2 (11.36 mmol) and 10% KOH/MeOH (40 mL) was refluxed overnight under N$_2$ and then diluted with dis-H$_2$O (100 mL), acidified with 2N HCl to pH 5~6 and extracted with EtOAC (50 mL×3), respectively. The combined EtOAc layer was dried over Na$_2$SO$_4$ and concentrated under reduced pressure. The residual was purified by silica gel (EtOAc:n-Hexane=1:2) to give 3.

(Z)-2-Benzoxy-3-prenyl-4-methoxy-cinamate (3a)

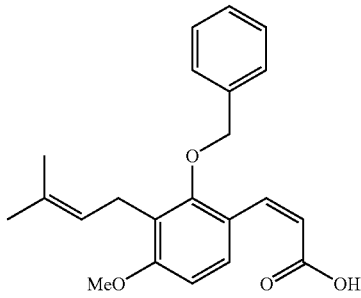

$^1$H-NMR (500 MHz, CDCl$_3$): δ 7.63 (1H, d, J=8.6 Hz), 7.42-7.26 (5H, m), 7.25 (1H, d, J=12.5 Hz), 6.80 (1H, d, J=8.7 Hz), 5.88 (1H, d, J=12.5 Hz), 5.16 (1H, t, J=6.6 Hz), 4.82 (2H, s), 3.85 (3H, s), 3.36 (2H, d, J=6.7 Hz), 1.65 (3H, s), 1.62 (3H, s). (cis)

General Procedure for the Preparation of 4

To a solution of potassium hydroxide (637 mg, 11.36 mmol) in MeOH (4 mL) was added hydroxylamine hydrochloride (790 mg, 11.36 mmol) dropwise and then stirred at ice-bath for 1 h. Filtration to remove the white salt yielded free hydroxylame in MeOH solution. To the mixture of 3a (1 g, 2.84 mmol) in dry THF (25 mL) was added ethyl chloroformate (0.6 mL, 5.68 mmol) and triethylamine (0.6 mL, 5.68 mmol) and the solution was stirred at for 0.5 h and then the prepared free hydroxylamine solution was added. After reacting for 3 h, the reaction mixture was concentrated under reduced pressure to give residue. The residue was purified by silica gel (EtOAc:n-Hexane=1:2) to give 4a.

(Z)-2-Benzoxy-3-prenyl-4-methoxy-N-hydroxy-cinamide (4a)

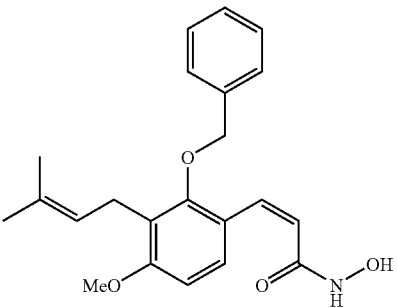

$^1$H-NMR (500 MHz, CDCl$_3$): δ 7.40-7.33 (5H, m), 7.30 (1H, d, J=8.6 Hz), 7.01 (1H, d, J=12.5 Hz), 6.66 (1H, d, J=8.7 Hz), 5.79 (1H, d, J=12.4 Hz), 5.17 (1H, t. J=6.6 Hz), 4.82 (2H, s), 3.83 (3H, s), 3.37 (2H, d, J=6.7 Hz), 1.69 (3H, s), 1.66 (3H, s); $^{13}$C-NMR (100 MHz, CDCl$_3$): δ 159.7 (s), 159.2 (s), 155.9 (s), 136.9 (s), 135.9 (d), 131.8 (s), 128.6 (d), 128.5 (d), 128.2 (d), 128.1 (d), 128.0 (d), 123.9 (s), 122.7 (d), 121.1 (s), 118.2 (d), 106.8 (d), 76.6 (t), 55.7 (q), 25.7 (q), 23.2 (t), 17.9 (q), 14.4 (q). (cis)

(Z)-2-(4-Methoxybenzoxy)-3-prenyl-4-methoxy-N-hydroxycinamide (4b)

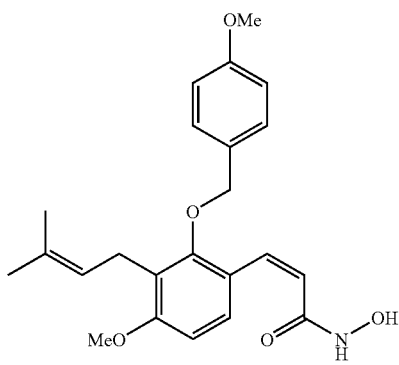

(4b)

$^{1}$H-NMR (500 MHz, CDCl$_3$): δ 7.35 (1H, d, J=8.6), 7.29 (2H, d, J=8.5 Hz), 6.99 (1H, d, J=12.5 Hz), 6.89 (2H, d, J=8.6 Hz), 6.66 (1H, d, J=8.6 Hz), 5.79 (1H, d, J=12.4 Hz), 5.17 (1H, t, J=6.8 Hz), 4.76 (2H, s), 3.83 (3H, s), 3.81 (3H, s), 3.37 (2H, d, J=6.6 Hz), 1.71 (3H, s), 1.67 (3H, s). (cis)

(Z)-2-(4-Fluorobenzoxy)-3-prenyl-4-methoxy-N-hydroxycinamide (4c)

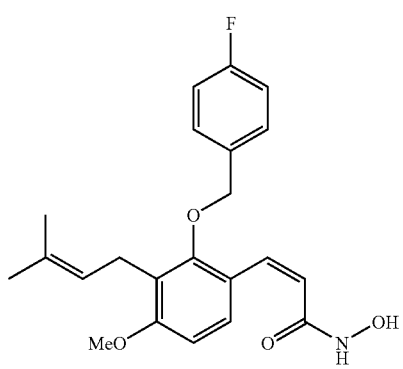

(4c)

$^{1}$H-NMR (500 MHz, CDCl$_3$): δ 7.40 (1H, d, J=7.8 Hz), 7.36 (2H, d, J=8.5 Hz), 7.06 (2H, d, J=8.5 Hz), 7.00 (1H, d, J=12.4 Hz), 6.65 (1H, d, J=7.8 Hz), 5.79 (1H, d, J=12.4 Hz), 5.14 (1H, t, J=6.2 Hz), 4.76 (2H, s), 3.80 (3H, s), 3.33 (2H, d, J=6.5 Hz), 1.67 (3H, s), 1.65 (3H, s). (cis)

(Z)-2-(4-Chlorobenzoxy)-3-prenyl-4-methoxy-N-hydroxycinamide (4d)

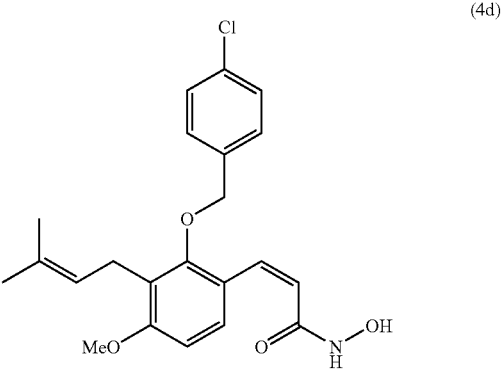

(4d)

$^{1}$H-NMR (500 MHz, CDCl$_3$): δ 7.34-7.31 (4H, m), 6.99 (1H, d, J=12.2 Hz), 6.69 (2H, d, J=8.3 Hz), 5.81 (1H, d, J=12.4 Hz), 5.13 (1H, t, J=6.2 Hz), 4.77 (2H, s), 3.85 (3H, s), 3.33 (2H, d, J=6.5 Hz), 1.67 (3H, s), 1.65 (3H, s). (cis)

(Z)-2-(4-Bromobenzoxy)-3-prenyl-4-methoxy-N-hydroxycinamide (4e)

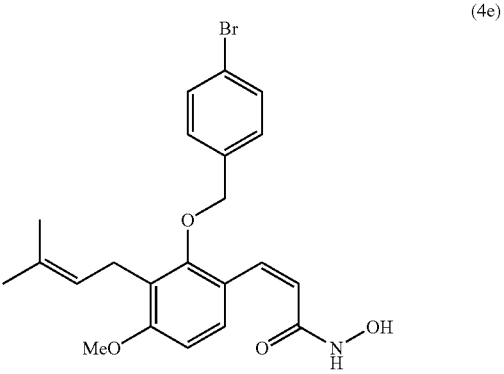

(4e)

$^{1}$H-NMR (500 MHz, CDCl$_3$): δ 7.47 (2H, d, J=8.1 Hz), 7.40 (1H, d, J=8.4 Hz), 7.28 (2H, d, J=8.1 Hz), 6.95 (1H, d, J=12.5 Hz), 6.62 (1H, d, J=8.4 Hz), 5.76 (1H, d, J=12.4 Hz), 4.73 (2H, s), 3.76 (3H, s), 3.31 (2H, d, J=6.1 Hz), 1.64 (6H, s). (cis)

(Z)-2-(4-Trifluoromethylbenzoxy)-3-prenyl-4-methoxy-N-hydroxycinamide (4f)

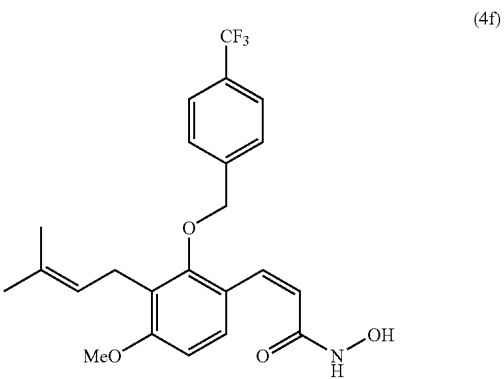

(4f)

¹H-NMR (500 MHz, CDCl₃): δ 7.64 (2H, d, J=8.1 Hz), 7.52 (2H, d, J=8.0 Hz), 7.43 (1H, d, J=8.4 Hz), 7.00 (1H, d, J=12.4 Hz), 6.68 (1H, d, J=8.6 Hz), 5.80 (1H, d, J=12.4 Hz), 5.14 (1H, t, J=6.4 Hz), 4.86 (2H, s), 3.84 (3H, s), 3.41 (2H, d, J=6.6 Hz), 1.66 (3H, s), 1.63 (3H, s). (cis)

(Z)-2-(3,4,5-Trimethoxybenzoxy)-3-prenyl-4-methoxy-N-hydroxycinamide (4g)

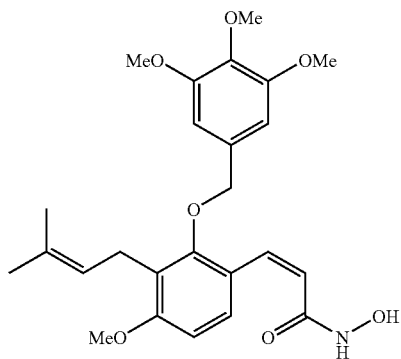

(4g)

¹H-NMR (500 MHz, CDCl₃): δ 7.41 (1H, d, J=8.3 Hz), 6.70 (1H, d, J=12.5 Hz), 6.65 (1H, d, J=8.4 Hz), 6.62 (1H, s), 6.61 (1H, s), 5.77 (1H, d, J=12.3 Hz), 5.17 (1H, t, J=6.6 Hz), 4.75 (2H, s), 3.84 (9H, s), 3.80 (3H, s), 3.35 (2H, d, J=6.4 Hz), 1.69 (3H, s), 1.65 (3H, s). (cis)

Scheme 2

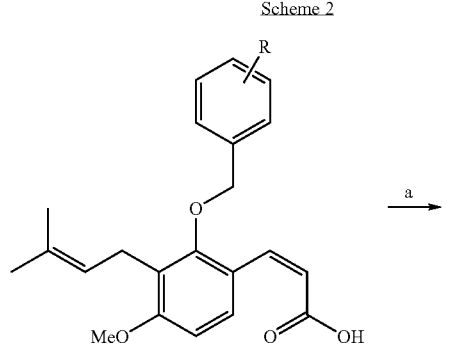

3a: R = H
3b: R = p-OMe
3d: R = p-Cl

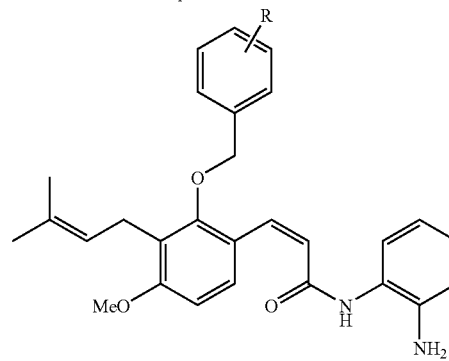

5a: R = H
5b: R = p-OMe
5c: R = p-Cl

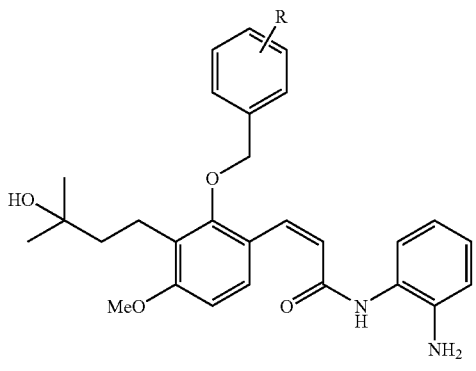

6a: R = H
6b: R = p-OMe
6c: R = p-Cl

Reagents and conditions: (a) (NH₂)₂C₆H₄, HOBT, DCC, CH₂Cl₂, rt; (b) H₂SO₄, THF, rt.

General Procedure for the Preparation of 5

The mixture of 3 (17.04 mmol), HOBT (2.76 g, 20.44 mmol) and DCC (4.22 g, 20.44 mmol) in dry THF (30 mL) was stirred at room temperature for 0.5 h and then added o-phenylenediamine (1.84 g, 17.04 mmol). The resulting solution was stirred continuously overnight and then concentrated under reduced pressure to obtain the residue. The residue was dissolved in CH₂Cl₂ (50 ml), washed with saturated NaHCO₃ (25 mL×3) and dried over Na₂SO₄. The organic layer was evaporated under reduced pressure and then purified by silica gel (EtOAc:n-Hexane=1:3~1:1) to give 5.

(Z)-2-Benzoxy-3-prenyl-4-methoxy-N-(2-aminophenyl)cinamide (5a)

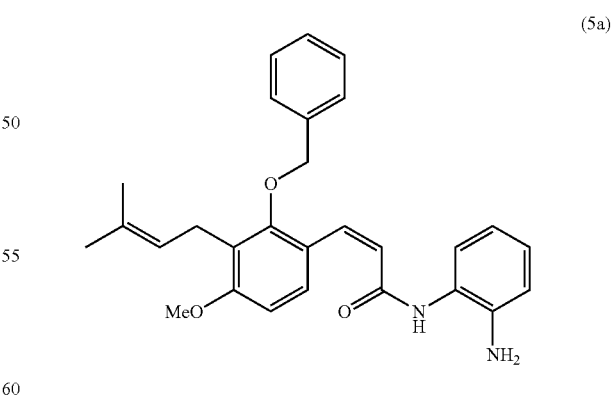

(5a)

¹H-NMR (500 MHz, CDCl₃): δ 7.43-7.38 (5H, m), 7.37 (1H, d, J=8.6 Hz), 7.03 (1H, d, J=12.5 Hz), 7.01-7.02 (2H, m), 6.74-6.72 (2H, m), 6.68 (1H, d, J=8.6 Hz), 6.06 (1H, d, J=12.4 Hz), 5.14 (1H, t. J=6.6 Hz), 4.90 (2H, s), 3.84 (3H, s), 3.65 (2H, s), 3.38 (2H, d, J=6.5 Hz), 1.72 (3H, s), 1.65 (3H, s). (cis)

25

(Z)-2-(4-Methoxybenzoxy)-3-prenyl-4-methoxy-N-(2-aminophenyl)cinamide (5b)

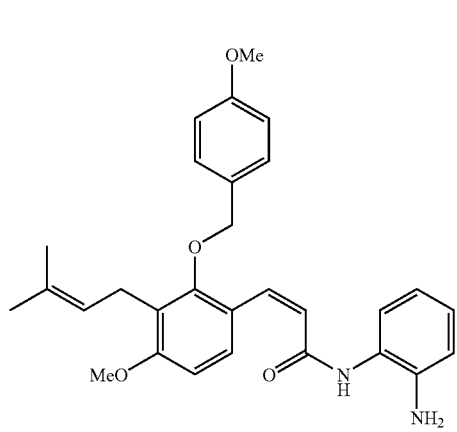

¹H-NMR (500 MHz, CDCl₃): δ 7.41 (1H, d, J=8.5 Hz), 7.33 (2H, d, J=8.3 Hz), 7.00 (1H, d, J=12.9 Hz), 6.88 (2H, d, J=8.4 Hz), 6.73-6.72 (2H, m), 6.67 (1H, d, J=8.6 Hz), 6.04 (1H, d, J=12.4 Hz), 5.15 (1H, t, J=6.6 Hz), 4.83 (2H, s), 3.87 (3H, s), 3.77 (3H, s), 3.38 (2H, d, J=6.3 Hz), 1.74 (3H, s), 1.67 (3H, s). (cis)

(Z)-2-(4-Chlorobenzoxy)-3-prenyl-4-methoxy-N-(2-aminophenyl)cinamide (5c)

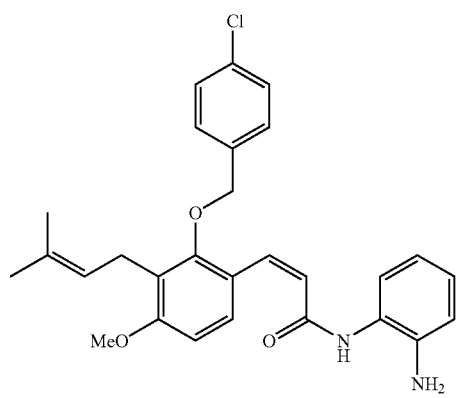

¹H-NMR (500 MHz, CDCl₃): δ 7.44 (1H, d, J=8.6 Hz), 7.35 (4H, m), 7.12 (1H, d, J=12.4 Hz), 7.00 (2H, d, J=10.5 Hz), 6.74 (2H, m), 6.69 (1H, d, J=8.6 Hz), 6.07 (1H, d, J=12.4 Hz), 5.13 (1H, t, J=6.6 Hz), 4.85 (2H, s), 3.84 (3H, s), 3.35 (2H, d, J=6.3 Hz), 1.65 (3H, s), 1.59 (3H, s). (cis)

General Procedure for the Preparation of 6

To a solution of 5 (1 mmol) in THF (15 mL) was added 49% H₂SO₄ (10 mL) and stirred at room temperature for 6 h. The resulting solution was extracted with CH₂Cl₂ (50 mL×3) and then dried over Na₂SO₄ to give residue. The residue was purified by silica gel (EtOAc:n-Hexane=2:1).

26

(Z)-2-Benzoxy-3-(2-Hydroxy-2-methylbutyl)-4-methoxy-N-(2-aminophenyl)cinamide (6a)

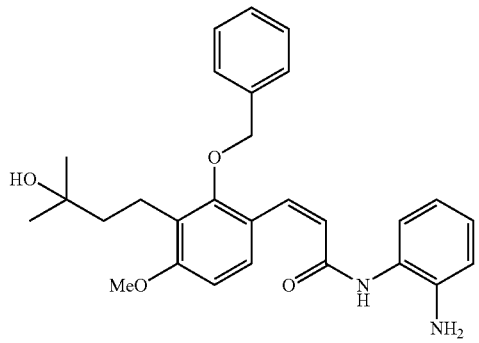

¹H-NMR (500 MHz, CDCl₃): δ 7.43-7.38 (5H, m), 7.37 (1H, d, J=8.6 Hz), 7.03 (1H, d, J=12.5 Hz), 7.01-7.02 (2H, m), 6.74-6.72 (2H, m), 6.68 (1H, d, J=8.6 Hz), 6.06 (1H, d, J=12.4 Hz), 4.92 (2H, s), 3.81 (3H, s), 2.68 (2H, m), 1.62 (2H, m), 1.18 (6H, s). (cis)

(Z)-2-(4-Methoxybenzoxy)-3-(2-Hydroxy-2-methyl-butyl)4-methoxy-N-(2-aminophenyl)cinamide (6b)

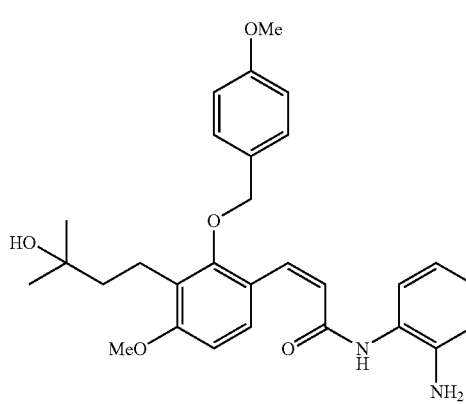

¹H-NMR (500 MHz, CDCl₃): δ 7.41 (1H, d, J=8.5 Hz), 7.33 (2H, d, J=8.3 Hz), 7.00 (2H, d, J=12.9 Hz), 6.88 (2H, d, J=8.4 Hz), 6.73-6.72 (4H, m), 6.67 (1H, d, J=8.6 Hz), 6.04 (1H, d, J=12.4 Hz), 4.83 (2H, s), 3.87 (3H, s), 3.77 (3H, s), 2.67 (2H, m), 1.64 (2H, m), 1.74 (3H, s), 1.67 (3H, s). (cis)

(Z)-2-(4-Chlorobenzoxy)-3-(2-Hydroxy-2-methylbutyl)-4-methoxy-N-(2-aminophenyl)cinamide (6c)

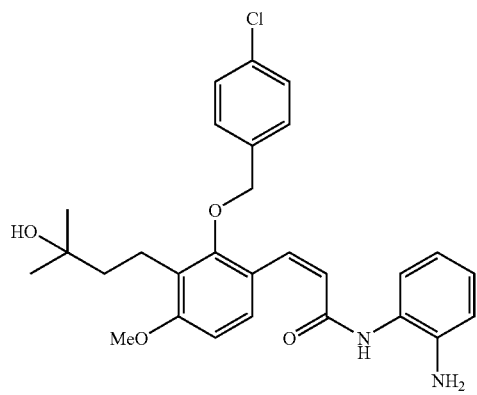

¹H-NMR (500 MHz, CDCl₃): δ 7.44 (1H, d, J=8.6 Hz), 7.35 (4H, m), 7.12 (1H, d, J=12.4 Hz), 7.00 (2H, d, J=10.5 Hz), 6.74 (2H, m), 6.69 (1H, d, J=8.6 Hz), 6.07 (1H, d, J=12.4 Hz), 4.85 (2H, s), 3.84 (3H, s), 3.35 (2H, d, J=6.3), 2.68-2.64 (2H, m), 1.65 (3H, s), 1.63-1.57 (2H, m), 1.59 (3H, s). (cis)

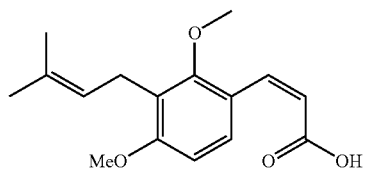

¹H-NMR (500 MHz, CDCl₃): δ 7.62 (1H, d, J=8.6 Hz), 7.23 (1H, d, J=12.5 Hz), 6.64 (1H, d, J=8.7 Hz), 5.92 (1H, d, J=12.5 Hz), 5.17 (1H, t, J=6.3 Hz), 3.84 (3H, s), 3.71 (3H, s), 3.34 (2H, d, J=6.7 Hz), 1.77 (3H, s), 1.67 (3H, s).

(Z)-2,4-Dimethoxy-3-prenyl-N-hydroxy cinamide (8)

Following the procedure similar to that of 4 and further purification by silica gel (EtOAc:n-Hexane=1:1) gave 8.

Scheme 3

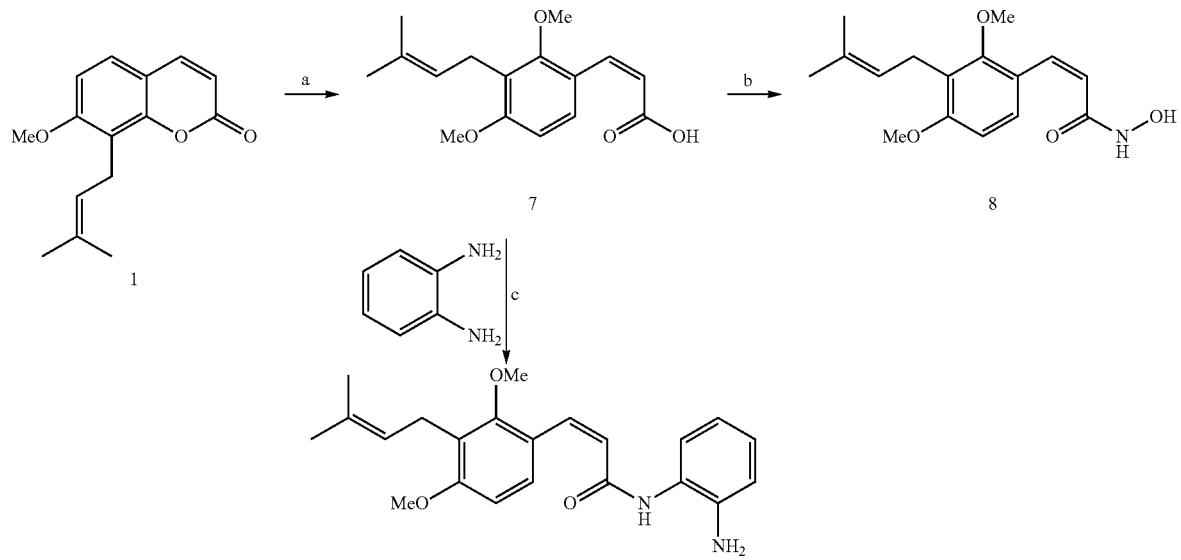

Reagents and conditions: (a) KOH, EtOH, MeI, Δ; (b) NH₂OH, ClCO₂Et, EtOH; (c) DCC, HOBT, THF, rt.

(Z)-2,4-Dimethoxy-3-prenyl cinamate (7)

To a solution of 1 (2.44 g, 10 mmol) and KOH (4.20 g, 75 mmol) dissolved in EtOH (100 ml) was added MeI (2.51 ml, 40 mmol) dropwise and then heated to 90° C. for 24 h. The mixture was diluted with dis-H₂O (100 ml), acidified with 1N HCl to pH 3-4 and then extracted with EtOAc (50 ml×3). The combined EtOAc layer was dried over Na₂SO₄, filtered and concentrated under reduced pressure. The residue was purified by silica gel (EtOAc:n-Hexane=6:1) to obtain 7.

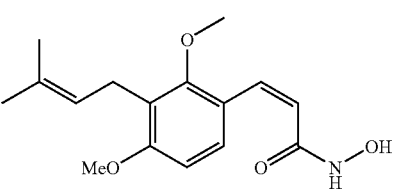

¹H-NMR (500 MHz, CDCl₃): δ 7.36 (1H, d, J=8.6 Hz), 7.02 (1H, d, J=12.5 Hz), 6.65 (1H, d, J=8.6 Hz), 5.87 (1H, d,

J=12.5 Hz), 5.16 (1H, t. J=6.9 Hz), 3.82 (3H, s), 3.70 (3H, s), 3.34 (2H, d, J=6.8 Hz), 1.77 (3H, s), 1.68 (3H, s).

(Z)-2,4-Dimethoxy-3-prenyl-N-(2-aminophenyl) cinamide (9)

Following the procedure similar to that of 5 and further purification by silica gel (EtOAc:n-Hexane=2:3) gave 9.

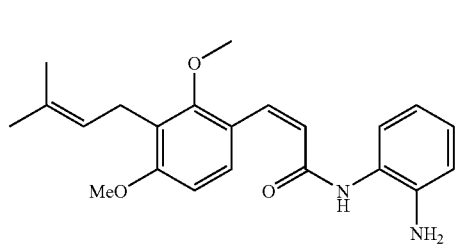

(9)

$^1$H-NMR (500 MHz, CD$_3$OD): δ 7.48 (1H, d, J=8.6 Hz), 7.09 (1H, d, J=12.4 Hz), 7.00-6.97 (2H, m), 6.83 (1H, d, J=8.1 Hz), 6.72-6.70 (2H, m), 6.16 (1H, d, J=12.4 Hz), 5.12 (1H, t, J=6.9 Hz), 3.81 (3H, s), 3.73 (3H, s), 3.35 (2H, d, J=6.7 Hz), 1.75 (3H, s), 1.63 (3H, s).

(Z)-2-Benzoxy-3-(2-Hydroxy-2-methylbutyl)-4-methoxy-t-butyl cinamate (10)

To a solution of 2a (0.27 mmol) in THF (15 mL) was added 49% H$_2$SO$_4$ (10 mL) and stirred at room temperature for 6 h. The resulting solution was extracted with CH$_2$Cl$_2$ (50 mL×3) and then dried over Na$_2$SO$_4$ to give residue. The residue was purified by silica gel (EtOAc:n-Hexane=1:1).

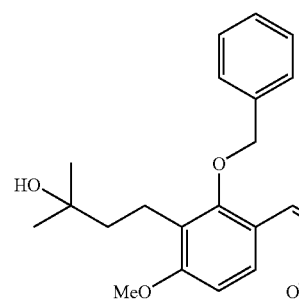

(10)

$^1$H-NMR (500 MHz, CDCl$_3$): δ 7.38 (1H, d, J=8.7 Hz), 7.36-7.27 (5H, m), 7.00 (1H, d, J=12.4 Hz), 6.60 (1H, d, J=8.7

Scheme 4

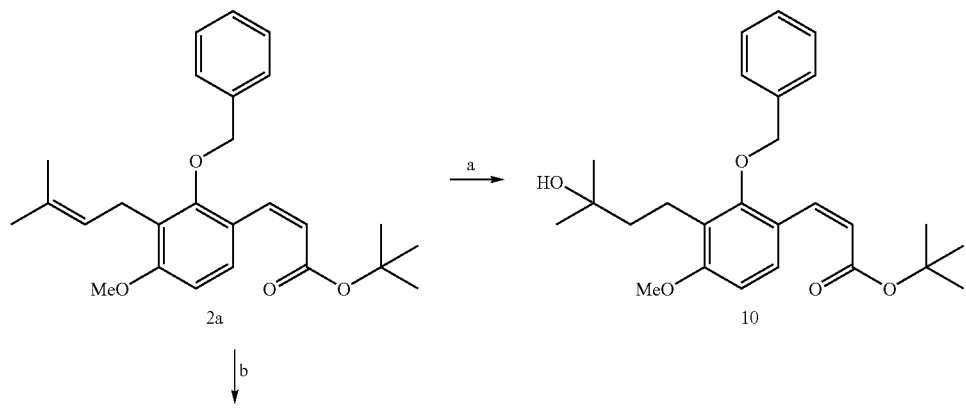

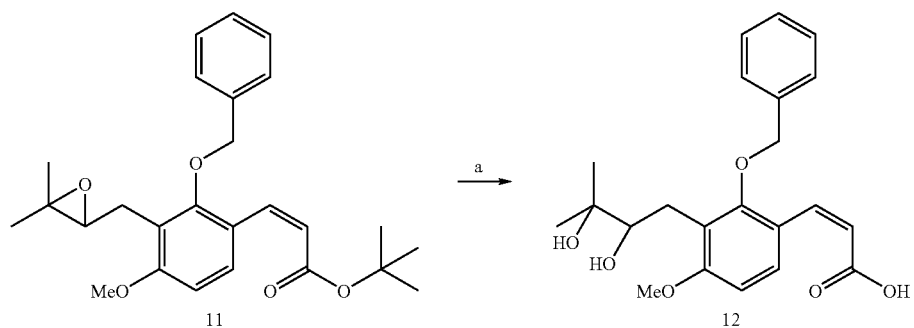

Reagents and conditions: (a) H$_2$SO$_4$, THF, rt; (b) MCPBA, CH$_2$Cl$_2$, rt.

Hz), 5.94 (1H, d, J=12.4 Hz), 5.13 (2H, s), 4.81 (2H, s), 3.82 (3H, s), 2.67 (2H, t, J=8.2 Hz), 1.61 (2H, t, J=8.2 Hz), 1.44 (9H, s), 1.18 (6H, s).

(Z)-2-Benzoxy-3-(2,3-epoxy-2-methylbutyl)-4-methoxy-t-butyl cinamate (11)

To a solution of 2a (1 g, 2.67 mmol) in CH$_2$Cl$_2$ (10 ml) was added 70% MCPBA (553 mg, 3.20 mmol) and stirred at rt for 2 h. The reaction mixture was washed with 1NaHSO$_3$, 10% NaHCO$_3$ and dried over Na$_2$SO$_4$. The CH$_2$Cl$_2$ was evaporated under reduced pressure and then purified by silica gel (EtOAc:n-Hexane=9:1) to obtain 11.

(1H, d, J=11.1 Hz), 4.83 (1H, d, J=11.1 Hz), 3.86 (3H, s), 2.97-2.94 (2H, m), 2.83-2.79 (1H, m), 1.44 (9H, s), 1.33 (3H, s), 1.25 (3H, s).

(Z)-2-Benzoxy-3-(2,3-dihydroxy-2-methylbutyl)-4-methoxy-cinamate (12)

Following the reaction procedure similar to that of 5 and further purification by silica gel (EtOAc:n-Hexane=1:4) gave 12.

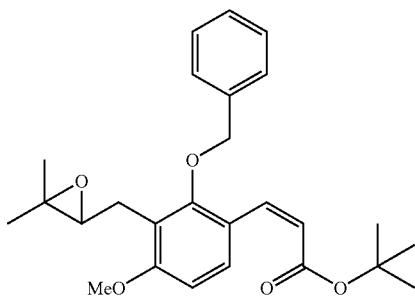

(11)

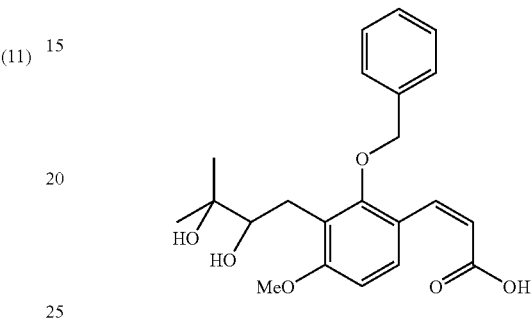

(12)

$^1$H-NMR (500 MHz, CDCl$_3$): δ 7.55 (1H, d, J=8.6 Hz), 7.43 (2H, d, J=7.1 Hz), 7.38-7.32 (3H, m), 7.08 (1H, d, J=12.4 Hz), 6.69 (1H, d, J=8.7 Hz), 5.86 (1H, d, J=12.4 Hz), 4.92

$^1$H-NMR (500 MHz, CDCl$_3$): δ 7.57 (1H, d, J=8.6 Hz), 7.40-7.34 (5H, m), 7.23 (1H, d, J=12.6 Hz), 6.72 (1H, d, J=8.7 Hz), 5.97 (1H, d, J=12.4 Hz), 4.91 (1H, d, J=11.1 Hz), 4.81 (1H, d, J=11.1 Hz), 3.88 (1H, t, J=10.5 Hz), 3.85 (3H, s), 2.63 (2H, d, J=10.5 Hz), 1.22 (3H, s), 1.16 (3H, s).

Scheme 5

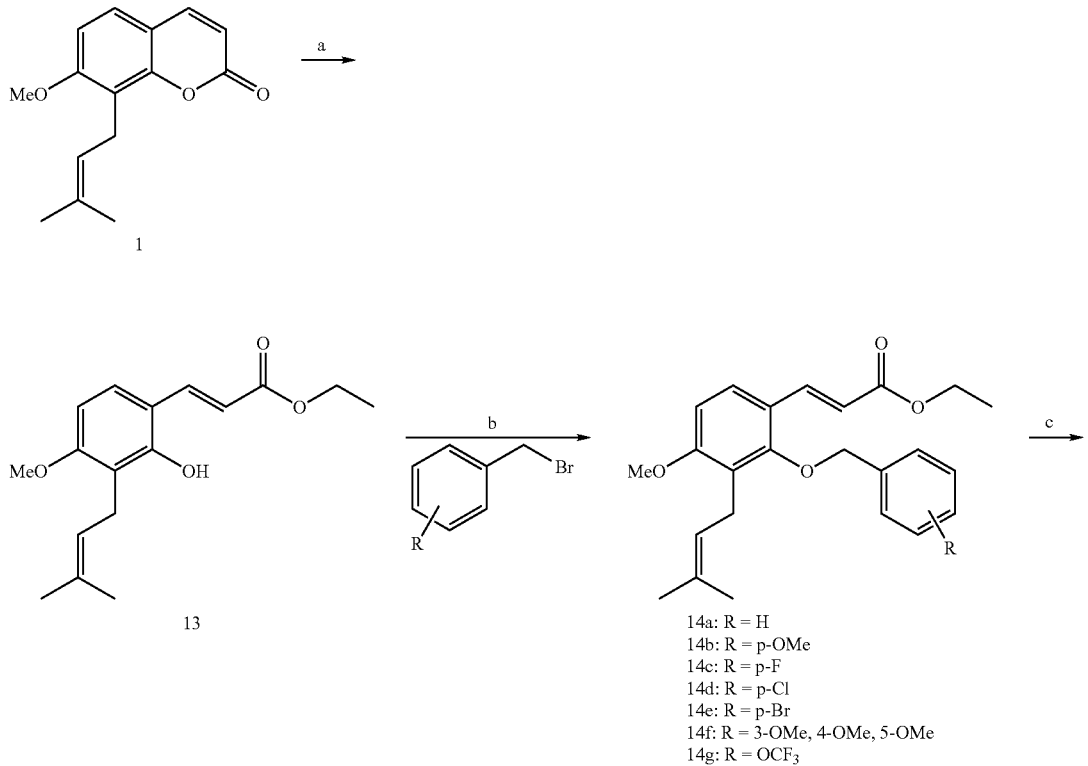

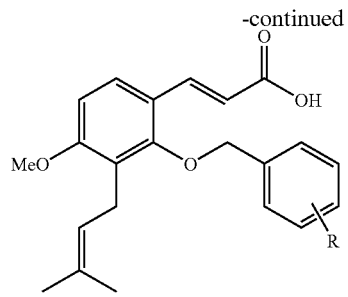

15a: R = H
15b: R = p-OMe
15c: R = p-F
15d: R = p-Cl
15e: R = p-Br
15f: R = 3-OMe, 4-OMe, 5-OMe
15g: R = OCF₃

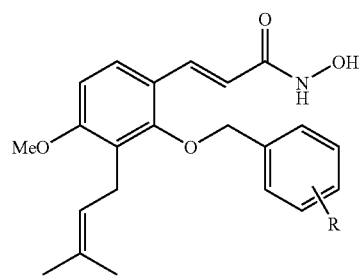

16a: R = H
16b: R = p-OMe
16c: R = p-F
16d: R = p-Cl
16e: R = p-Br
16f: R = 3-OMe, 4-OMe, 5-OMe
16g: R = OCF₃

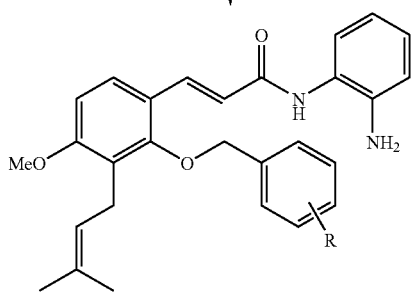

17a: R = H
17b: R = p-OMe
17c: R = p-F
17d: R = p-Cl
17e: R = p-Br
17f: R = 3-OMe, 4-OMe, 5-OMe
17g: R = OCF₃

Reagents and conditions: (a) NaOEt, EtOH, N₂, Δ; (b) K₂CO₃, acetone, Δ; (c) KOH, MeOH, Δ; (d) NH₂OH, ClCO₂Et, EtOH; (e) DCC, HOBT, THF, rt.

(E) 2-Hydroxy-3-prenyl-4-methoxy-ethyl cinamate (13)

To the solution of 1 (2.40 g, 10 mmol) in dry EtOH (20 mL) was added the mixture of sodium ethoxide (1.36 g, 20 mmol) in dry EtOH (20 mL) dropwise, the resulting solution was heated under nitrogen for 6 h and then diluted with dis-H₂O (50 mL), acidified with 1N HCl$_{(aq)}$ to pH 4-5, extracted with EtOAc (50 mL×3) and dried over Na₂SO₄. After removal of EtOAc under reduced pressure, the residue was purified by silica gel (EtOAc:n-Hexane=10:1) to give 13.

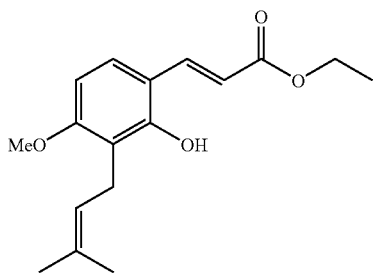

(13)

¹H-NMR (500 MHz, CDCl₃): δ 7.92 (1H, d, J=16.1 Hz), 7.33 (1H, d, J=8.7 Hz), 6.49 (1H, d, J=8.7 Hz), 6.44 (1H, d, J=16.1 Hz), 6.10 (1H, s), 5.20 (1H, t, J=7.0 Hz), 4.23 (2H, q, J=7.2 Hz), 3.82 (3H, s), 3.42 (1H, d, J=7.1 Hz), 1.82 (3H, s), 1.75 (3H, s), 1.31 (3H, t, J=7.2 Hz). (trans)

General Procedure for the Preparation of 14

To the mixture of 13 (1.72 mmol) and K₂CO₃ (4.3 mmol) in acetone (20 mL) was added appropriate benzyl bromide (3.44 mmol), the resulting solution was heated under N₂ overnight. After filteration to remove K₂CO₃, the filtrate was condensed under reduced pressure. The resulting residue was purified by gel (EtOAc:n-Hexane=15:1) to give 14.

(E)-2-(4-Methoxybenzoxy)-3-prenyl-4-methoxy-ethyl cinamate (14a)

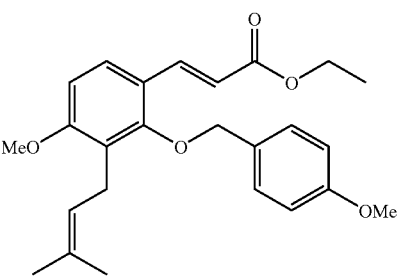

(14a)

¹H-NMR (500 MHz, CDCl₃): δ 7.98 (1H, d, J=16.1 Hz), 7.44 (1H, d, J=8.7 Hz), 7.40 (2H, d, J=8.4 Hz), 6.92 (2H, d,

J=8.4 Hz), 6.71 (1H, d, J=8.7 Hz), 6.34 (1H, d, J=16.1 Hz), 5.17 (1H, t, J=6.4 Hz), 4.74 (2H, s), 4.25 (2H, q, J=7.1 Hz), 3.86 (3H, s), 3.83 (3H, s), 3.39 (2H, d, J=6.5 Hz), 1.73 (3H, s), 1.67 (3H, s), 1.33 (3H, t, J=7.1 Hz). (trans)

(E)-2-(4-Chlorobenzoxy)-3-prenyl-4-methoxy-ethyl cinamate (14b)

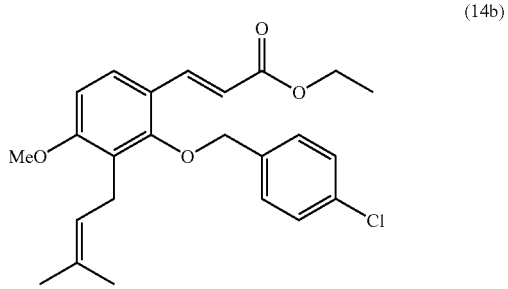

(14b)

$^1$H-NMR (500 MHz, CDCl$_3$): δ 7.92 (1H, d, J=16.1 Hz), 7.44 (1H, d, J=8.7 Hz), 7.41 (2H, d, J=8.4 Hz), 7.37 (2H, d, J=8.4 Hz), 6.72 (1H, d, J=8.7 Hz), 6.34 (1H, d, J=16.0 Hz), 5.16 (1H, t, J=6.6 Hz), 4.77 (2H, s), 4.23 (2H, q, J=7.2 Hz), 3.86 (3H, s), 3.37 (2H, d, J=6.6 Hz), 1.69 (3H, s), 1.67 (3H, s), 1.31 (3H, t, J=7.2 Hz). (trans)

(E)-2-(4-Bromobenzoxy)-3-prenyl-4-methoxy-ethyl cinamate (14c)

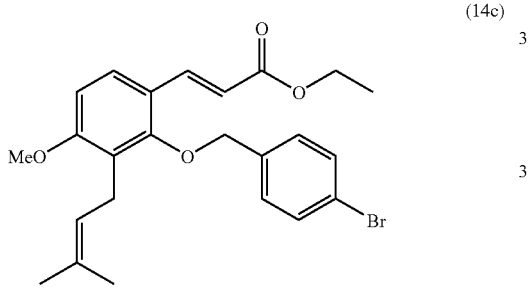

(14c)

$^1$H-NMR (500 MHz, CDCl$_3$): δ 7.91 (1H, d, J=16.1 Hz), 7.52 (2H, d, J=8.4 Hz), 7.44 (1H, d, J=8.7 Hz), 7.34 (2H, d, J=8.4 Hz), 6.72 (1H, d, J=8.7 Hz), 6.34 (1H, d, J=16.0 Hz), 5.16 (1H, t, J=6.6 Hz), 4.75 (2H, s), 4.23 (2H, q, J=7.1 Hz), 3.87 (3H, s), 3.36 (2H, d, J=6.6 Hz), 1.70 (3H, s), 1.68 (3H, s), 1.31 (3H, t, J=7.1 Hz). (trans)

(E)-2-(3,4,5-Trimethoxybenzoxy)-3-prenyl-4-methoxy-ethyl cinamate (14d)

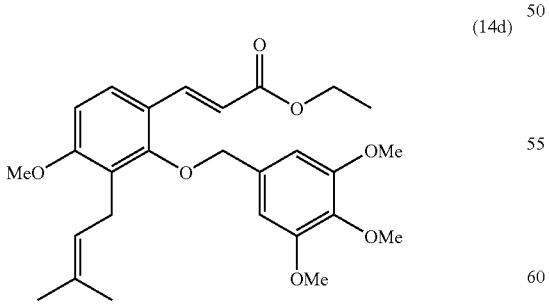

(14d)

$^1$H-NMR (500 MHz, CDCl$_3$): δ 7.96 (1H, d, J=16.1 Hz), 7.45 (1H, d, J=8.6 Hz), 6.72 (1H, d, J=8.8 Hz), 6.70 (2H, s), 6.38 (1H, d, J=16.0 Hz), 5.20 (1H, t, J=6.6 Hz), 4.74 (2H, s), 4.22 (2H, q, J=7.1 Hz), 3.90 (6H, s), 3.87 (3H, s), 3.86 (3H, s), 3.40 (2H, d, J=6.5 Hz), 1.74 (3H, s), 1.68 (3H, s), 1.30 (3H, t, J=7.2 Hz). (trans)

General Procedure for the Preparation of 15

The mixture of 14 (1.81 mmol) and 10% KOH/MeOH (20 mL) was refluxed overnight under N$_2$ and then diluted with dis-H$_2$O (100 mL), acidified with 2N HCl to pH 5~6 and extracted with EtOAc (50 mL×3), respectively. The combined EtOAc layer was dried over Na$_2$SO$_4$ and concentrated under reduced pressure to give 15.

(E)-2-(4-Methoxybenzoxy)-3-prenyl-4-methoxy-cinamate (15a)

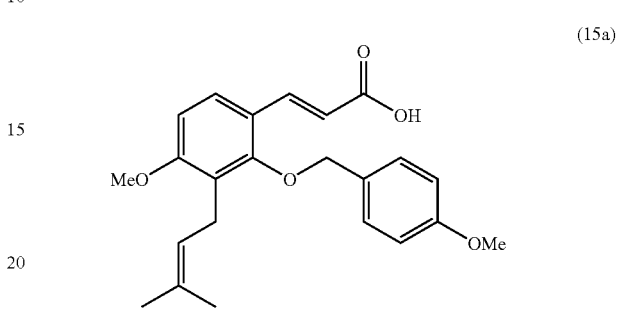

(15a)

$^1$H-NMR (500 MHz, CDCl$_3$): δ 8.06 (1H, d, J=16.1 Hz), 7.47 (1H, d, J=8.7 Hz), 7.39 (2H, d, J=8.5 Hz), 6.93 (2H, d, J=8.5 Hz), 6.73 (1H, d, J=8.7 Hz), 6.35 (1H, d, J=16.0 Hz), 5.18 (1H, t, J=6.5 Hz), 4.76 (2H, s), 3.88 (3H, s), 3.82 (3H, s), 3.39 (1H, d, J=6.5 Hz), 1.73 (3H, s), 1.68 (3H, s). (trans)

(E)-2-(4-Chlorobenzoxy)-3-prenyl-4-methoxy-cinamate (15b)

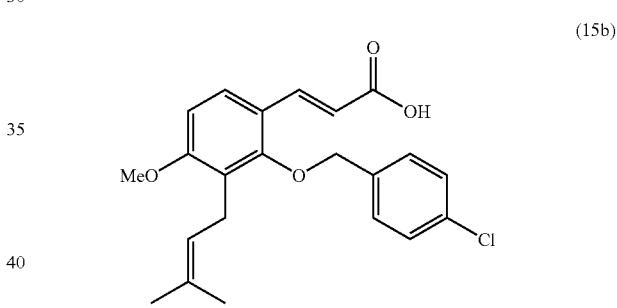

(15b)

$^1$H-NMR (500 MHz, DMSO-d6): δ 7.69 (1H, d, J=16.0 Hz), 7.64 (1H, d, J=8.8 Hz), 7.47 (2H, d, J=9.3 Hz), 7.44 (2H, d, J=9.3 Hz), 6.87 (1H, d, J=8.8 Hz), 6.37 (1H, d, J=16.0 Hz), 5.06 (1H, t, J=6.4 Hz), 4.75 (2H, s), 3.82 (3H, s), 3.25 (1H, d, J=6.6 Hz), 1.58 (6H, s). (trans)

(E)-2-(4-Bromobenzoxy)-3-prenyl-4-methoxy-cinamate (15c)

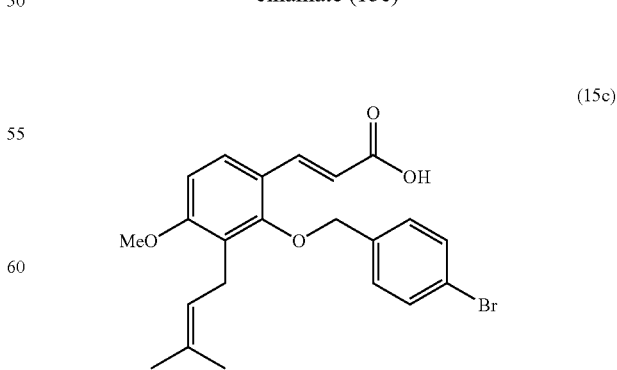

(15c)

$^1$H-NMR (500 MHz, DMSO-d6): δ 7.71 (1H, d, J=16.1 Hz), 7.65 (1H, d, J=8.7 Hz), 7.60 (2H, d, J=8.3 Hz), 7.40 (2H, d, J=8.3 Hz), 6.88 (1H, d, J=8.8 Hz), 6.38 (1H, d, J=16.1 Hz), 5.06 (1H, t, J=6.5 Hz), 4.74 (2H, s), 3.82 (3H, s), 3.26 (2H, d, J=6.6 Hz), 1.59 (6H, s). (trans)

(E)-2-(3,4,5-Trimethoxybenzoxy)-3-prenyl-4-methoxy-cinamate (15d)

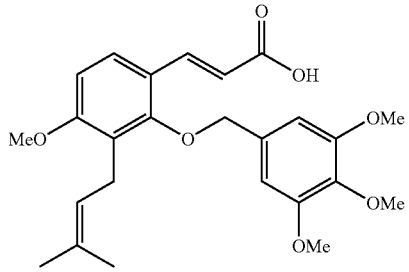

(15d)

$^1$H-NMR (500 MHz, CDCl$_3$): δ 7.96 (1H, d, J=16.1 Hz), 7.45 (1H, d, J=8.6 Hz), 6.72 (1H, d, J=8.8 Hz), 6.70 (2H, s), 6.38 (1H, d, J=16.0 Hz), 5.20 (1H, t, J=6.6 Hz), 4.74 (2H, s), 3.90 (6H, s), 3.87 (3H, s), 3.86 (3H, s), 3.40 (2H, d, J=6.5 Hz), 1.74 (3H, s), 1.68 (3H, s). (trans)

General Procedure for the Preparation of 16

To a solution of potassium hydroxide (637 mg, 11.36 mmol) in MeOH (4 mL) was added hydroxylamine hydrochloride (790 mg, 11.36 mmol) dropwise and then stirred in an ice-bath for 1 h. Filtration to remove the white salt gave free hydroxylame in MeOH solution. To the mixture of 15 (2.84 mmol) in dry THF (25 mL) was added ethyl chloroformate (0.6 mL, 5.68 mmol) and triethylamine (0.6 mL, 5.68 mmol) and stirred for 0.5 h and then added the prepared free hydroxylamine solution. After reacting for 3 h, the reaction mixture was concentrated under reduced pressure to give residue. The residue was purified by silica gel (EtOAc:n-Hexane=1:1) to give 16.

(E)-2-(4-Methoxybenzoxy)-3-prenyl-4-methoxy-N-hydroxy cinamide (16a)

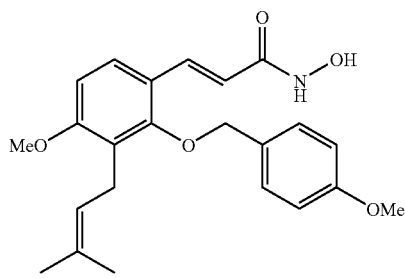

(16a)

$^1$H-NMR (500 MHz, CDCl$_3$): δ 7.83 (1H, d, J=15.5 Hz), 7.33 (2H, d, J=8.4 Hz), 7.27 (1H, d, J=8.6 Hz), 6.88 (2H, d, J=8.3 Hz), 6.52 (1H, d, J=8.6 Hz), 6.28 (1H, d, J=15.5 Hz), 5.12 (1H, t, J=5.7 Hz), 4.64 (2H, s), 3.76 (3H, s), 3.74 (3H, s), 3.33 (2H, d, J=6.2 Hz), 1.70 (3H, s), 1.64 (3H, s). (trans)

(E)-2-(4-Chlorobenzoxy)-3-prenyl-4-methoxy-N-hydroxy cinamide (16b)

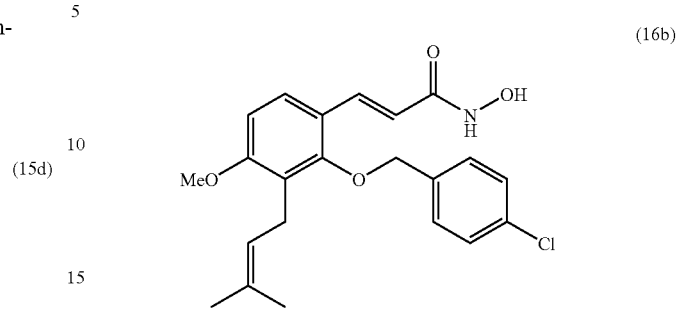

(16b)

$^1$H-NMR (500 MHz, MeOH-d4): δ 7.83 (1H, d, J=15.8 Hz), 7.47 (1H, d, J=8.7 Hz), 7.44 (2H, d, J=8.2 Hz), 7.37 (2H, d, J=8.3 Hz), 6.81 (1H, d, J=8.7 Hz), 6.36 (1H, d, J=15.8 Hz), 5.09 (1H, t, J=6.5 Hz), 4.76 (2H, s), 3.84 (3H, s), 3.32 (1H, d, J=6.6 Hz), 1.63 (3H, s), 1.62 (3H, s). (trans)

(E)-2-(4-Bromobenzoxy)-3-prenyl-4-methoxy-N-hydroxy cinamide (16c)

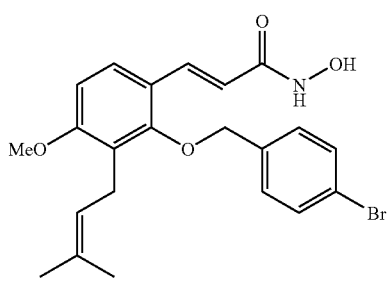

(16c)

$^1$H-NMR (500 MHz, acetone-d6): δ 7.86 (1H, d, J=15.8 Hz), 7.60 (2H, d, J=8.4 Hz), 7.51 (1H, d, J=8.7 Hz), 7.49 (2H, d, J=8.3 Hz), 6.86 (1H, d, J=8.7 Hz), 6.50 (1H, d, J=15.8 Hz), 5.14 (1H, t, J=6.7 Hz), 4.80 (2H, s), 3.87 (3H, s), 3.36 (1H, d, J=6.7 Hz), 1.65 (3H, s), 1.61 (3H, s). (trans)

(E)-2-(3,4,5-Trimethoxybenzoxy)-3-prenyl-4-methoxy-N-hydroxy cinamide (16d)

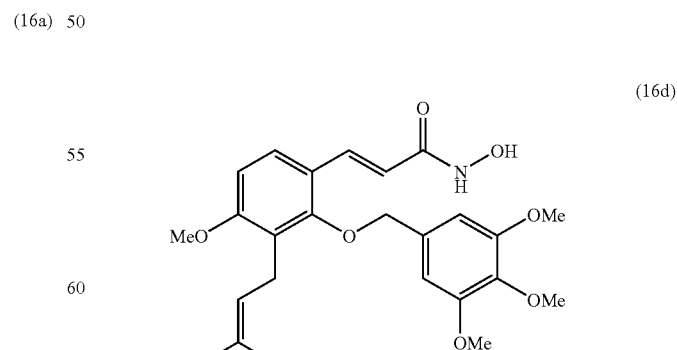

(16d)

$^1$H-NMR (500 MHz, CDCl$_3$): δ 7.88 (1H, d, J=15.7 Hz), 7.35 (1H, d, J=8.6 Hz), 6.68 (2H, s), 6.62 (1H, d, J=8.7 Hz), 6.28 (1H, d, J=15.7 Hz), 5.18 (1H, t, J=6.0 Hz), 4.68 (2H, s), 3.86 (6H, s), 3.84 (3H, s), 3.82 (3H, s), 3.38 (2H, d, J=6.4 Hz), 1.73 (3H, s), 1.66 (3H, s). (trans)

(E)-2-Benzoxy-3-prenyl-4-methoxy-N-(2-aminophenyl)cinamide (17a)

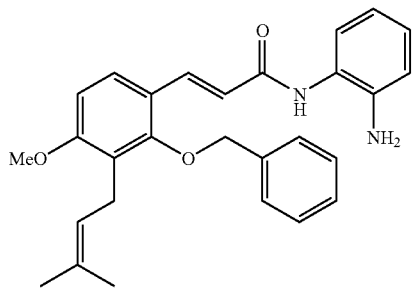

(17a)

¹H-NMR (500 MHz, CDCl₃): δ 7.87 (1H, d, J=15.1 Hz), 7.40-7.35 (5H, m), 7.32 (1H, d, J=7.8 Hz), 7.03 (2H, m), 6.77 (2H, m), 6.67 (1H, d, J=8.1 Hz), 6.49 (1H, d, J=15.6 Hz), 5.19 (1H, m), 4.79 (2H, s), 3.85 (3H, s), 3.40 (2H, d, J=6.1 Hz), 1.70 (3H, s), 1.67 (3H, s)

(E)-2-(4-Methoxybenzoxy)-3-prenyl-4-methoxy-N-(2-aminophenyl)cinamide

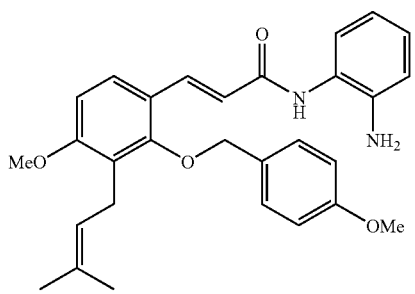

(17b)

¹H-NMR (500 MHz, CDCl₃): δ 7.85 (1H, d, J=15.1 Hz), 7.39 (4H, d, J=7.6 Hz), 7.12-7.04 (2H, m), 6.90 (1H, d, J=8.2 Hz), 6.78 (2H, d, J=7.3 Hz), 6.68 (1H, d, J=8.1 Hz), 6.54 (1H, d, J=15.2 Hz), 5.19 (1H, m), 4.73 (2H, s), 3.86 (3H, s), 3.77 (3H, s), 3.41 (2H, m), 1.74 (3H, s), 1.67 (3H, s)

(E)-2-(4-Fluorobenzoxy)-3-prenyl-4-methoxy-N-(2-aminophenyl)cinamide (17c)

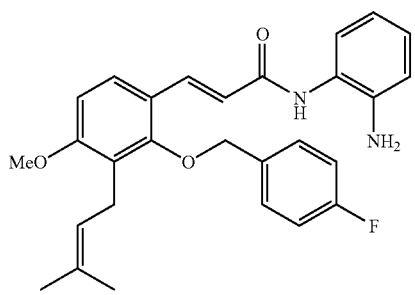

(17c)

¹H-NMR (500 MHz, CDCl₃): δ 7.90 (1H, d, J=15.2 Hz), 7.43-7.38 (4H, m), 7.07-7.03 (4H, m), 6.76 (2H, d, J=7.0 Hz), 6.65 (1H, d, J=8.4 Hz), 6.51 (1H, d, J=15.7 Hz), 5.16 (1H, m), 4.76 (2H, s), 3.84 (3H, s), 3.34 (2H, d, J=6.5 Hz), 1.69 (3H, s), 1.66 (3H, s)

(E)-2-(4-Chlorobenzoxy)-3-prenyl-4-methoxy-N-(2-aminophenyl)cinamide (17d)

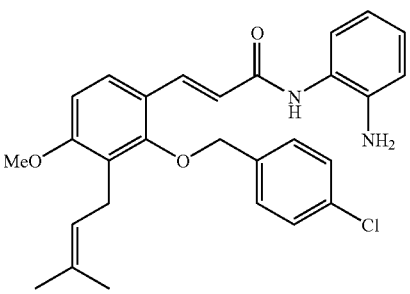

(17d)

¹H-NMR (500 MHz, CDCl₃): δ 7.88 (1H, d, J=15.4 Hz), 7.39-7.35 (4H, m), 7.34 (1H, d, J=7.9), 7.05 (2H, m), 6.78 (2H, m), 6.69 (1H, d, J=8.0 Hz), 6.50 (1H, d, J=15.4 Hz), 5.15 (1H, m), 4.78 (2H, s), 3.86 (3H, s), 3.34 (2H, d, J=6.3 Hz), 1.68 (3H, s), 1.66 (3H, s)

(E)-2-(4-Bromobenzoxy)-3-prenyl-4-methoxy-N-(2-aminophenyl)cinamide (17e)

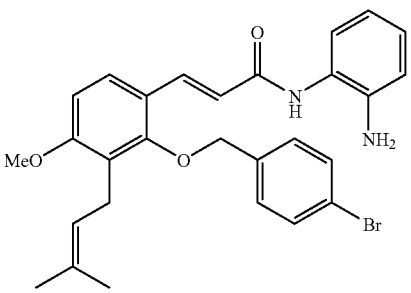

(17e)

¹H-NMR (500 MHz, CDCl₃): δ 7.88 (1H, d, J=15.3 Hz), 7.50 (2H, d, J=7.8 Hz), 7.40 (1H, d, J=7.4 Hz), 7.34 (2H, m), 7.05 (2H, m), 6.81 (2H, m), 6.71 (1H, d, J=7.6 Hz), 6.52 (1H, d, J=15.5 Hz), 5.15 (1H, m), 4.77 (2H, s), 3.86 (3H, s), 3.37 (2H, m), 1.66 (3H, s), 1.57 (3H, s)

Scheme 6

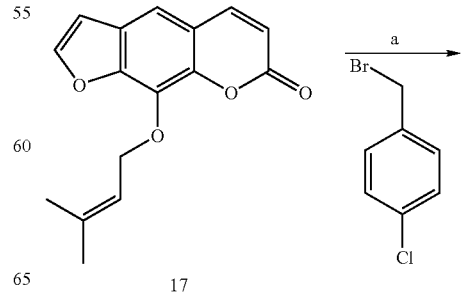

17

41
-continued

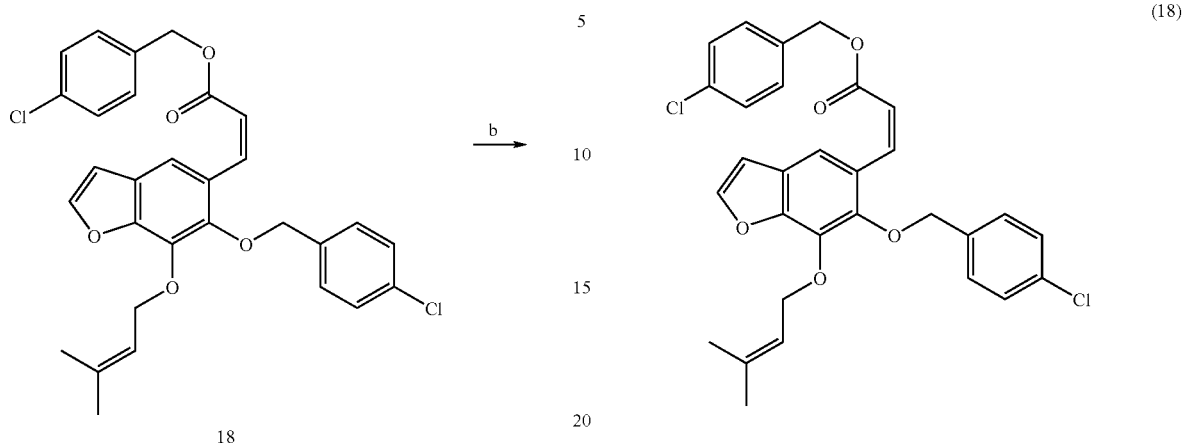

18

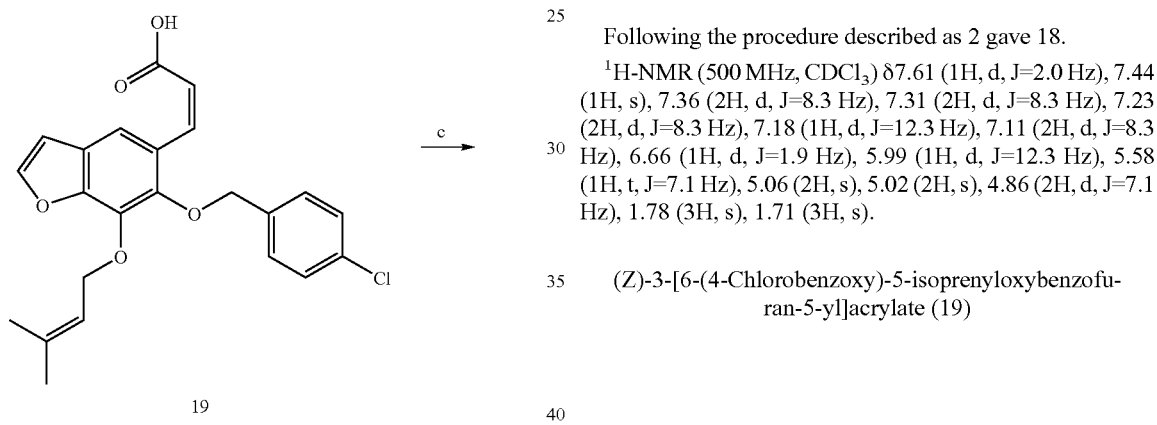

19

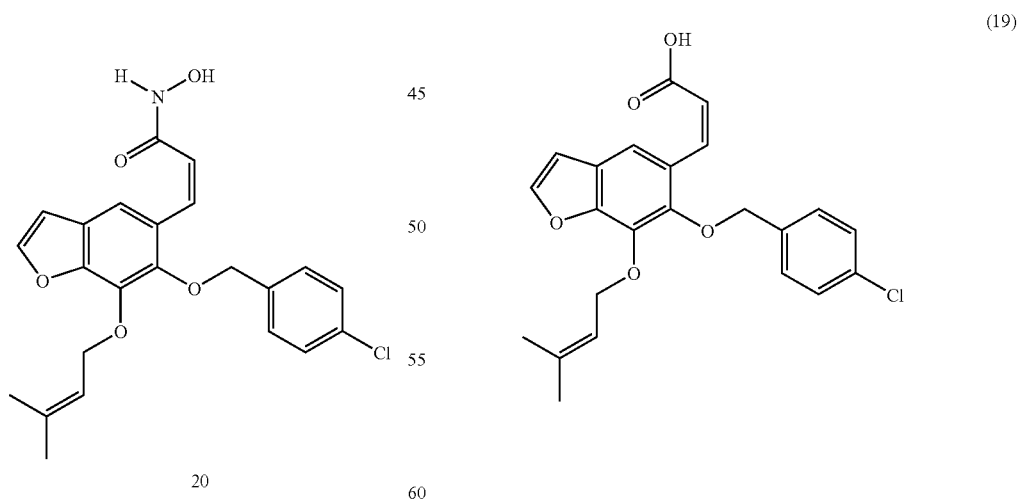

20

Reagents and conditions: (a) t-BuOK, DMF, 90° C.; (b) LiOH, MeOH, Δ (c) NH₂OH, ClCO₂Et, EtOH, rt

42

(Z)-3-[6-(4-Chlorobenzoxy)-5-isoprenyloxybenzofuran-5-yl]4-chlorobenzyl acrylate (18)

(Z)-3-[6-(4-Chlorobenzoxy)-5-isoprenyloxybenzofuran-5-yl]4-chlorobenzyl acrylate (18)

Following the procedure described as 2 gave 18.

$^1$H-NMR (500 MHz, CDCl$_3$) δ7.61 (1H, d, J=2.0 Hz), 7.44 (1H, s), 7.36 (2H, d, J=8.3 Hz), 7.31 (2H, d, J=8.3 Hz), 7.23 (2H, d, J=8.3 Hz), 7.18 (1H, d, J=12.3 Hz), 7.11 (2H, d, J=8.3 Hz), 6.66 (1H, d, J=1.9 Hz), 5.99 (1H, d, J=12.3 Hz), 5.58 (1H, t, J=7.1 Hz), 5.06 (2H, s), 5.02 (2H, s), 4.86 (2H, d, J=7.1 Hz), 1.78 (3H, s), 1.71 (3H, s).

(Z)-3-[6-(4-Chlorobenzoxy)-5-isoprenyloxybenzofuran-5-yl]acrylate (19)

Following the procedure described as 3 gave 19.

$^1$H-NMR (500 MHz, CDCl$_3$) δ7.58 (1H, d, J=2.0 Hz), 7.53 (1H, s), 7.33 (2H, d, J=8.3 Hz), 7.30 (2H, d, J=8.3 Hz), 7.22 (1H, d, J=12.5 Hz), 6.71 (1H, d, J=2.1 Hz), 5.92 (1H, d, J=12.4 Hz), 5.56 (1H, t, J=7.2 Hz), 5.02 (2H, s), 4.85 (2H, d, J=7.1 Hz), 1.75 (3H, s), 1.66 (3H, s).

(Z)-3-[6-(4-Chlorobenzoxy)-5-isoprenyloxybenzofuran-5-yl]-N-hydroxyacrylmide (20)

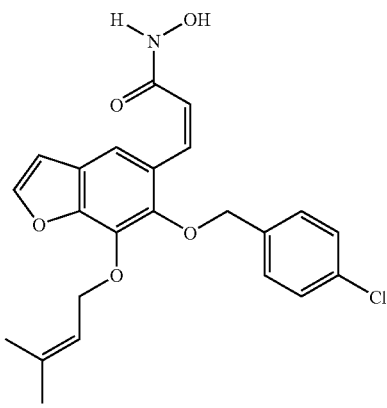

Following the procedure described as 4 gave 20.

$^1$H-NMR (500 MHz, CDCl$_3$) δ7.58 (1H, s), 7.35~7.30 (4H, m), 7.32 (1H, s), 7.00 (1H, d, J=12.4 Hz), ~~ (1H, s), 5.86 (1H, d, J=12.5 Hz), 5.56 (1H, t, J=6.9 Hz), 5.50 (2H, s), 4.89 (2H, d, J=7.1 Hz), 1.76 (3H, s), 1.69 (3H, s)

Scheme 7

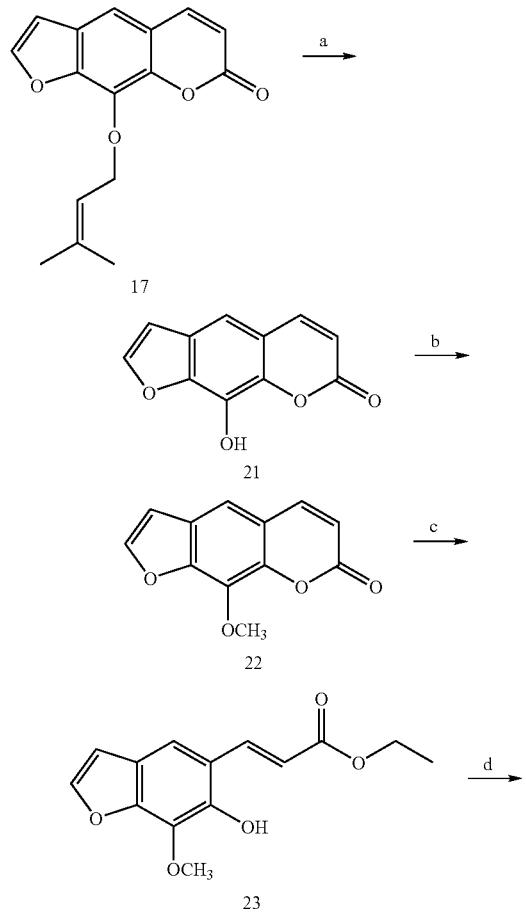

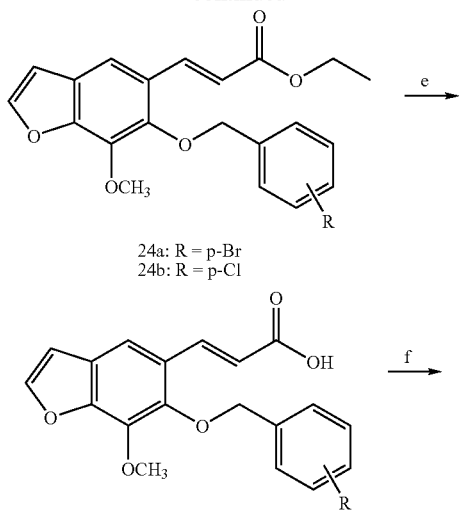

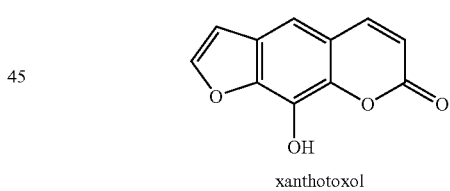

Reagents and conditions: (a) H$_2$SO$_4$, THF, rt; (b) K$_2$CO$_3$, DMS, acetone, Δ; (c) NaOEt, EtOH, N$_2$ Δ; (d) K$_2$CO$_3$, acetone, Δ; (e)KOH, MeOH, Δ; (f)NH$_2$OH, ClCO$_2$Et, EtOH To a solution of 1 (18.51 mmol) in THF (150 mL) was added 49% H$_2$SO$_4$ (100 mL) and stirred at room temperature for 6 h. The resulting solution was extracted with CH$_2$Cl$_2$ (50 mL×3) and then dried over Na$_2$SO$_4$ to give residue. The residue was purified by silica gel (EtOAc:n-Hexane=1:2).

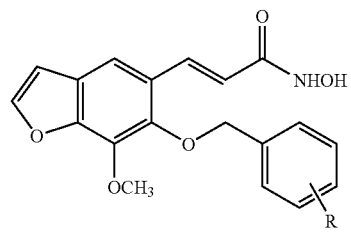

xanthotoxol $^1$H-NMR (500 MHz, d$_6$-acetone): δ 8.02 (1H, d, J=9.5 Hz), 7.91 (1H, d, J=2.1 Hz), 7.41 (1H, s), 6.96 (1H, d, J=2.1 Hz), 6.32 (1H, d, J=9.5 Hz)

Preparation of 8-Methyl-xanthotoxol (22)

Compound 21 (1 g, 4.95 mmol) dissolved in acetone (150 mL). To the mixture of the solution of 1 and K$_2$CO$_3$ (1.7 g, 12.4 mmol) was added dimethyl sulfate (0.96 mL, 5.85 mmol), the resulting solution was refluxed for 2 hour under nitrogen. After filteration to remove K$_2$CO$_3$, the filtrate was condensed under reducted pressure and then diluted with EtOAc (50 mL), washed with dis-H$_2$O (25 mL×3) and dried over Na$_2$SO$_4$. After removal of EtOAc under reduced pressure, the residue was purified by silica gel (EtOAc:n-Hexane=1:2) to give 22

8-Methyl-xanthotoxol (22)

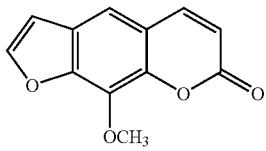

22

¹H-NMR (500 MHz, CDCl₃): δ 7.75 (1H, d, J=9.5 Hz), 7.67 (1H, d, J=5.0 Hz), 7.32 (1H, s), 6.80 (1H, d, J=5.0 Hz), 6.35 (1H, d, J=9.5 Hz)

To the solution of 22 (1.06 g, 4.94 mmol) in dry EtOH (25 mL) was added the mixture of sodium ethoxide (0.50 g, 7.41 mmol) in dry EtOH (25 mL) dropwise, the resulting solution was refluxed under nitrogen overnight and then diluted with dis-H₂O (50 mL), neutralized with 1N HCl$_{(aq)}$ to pH 4-5, extracted with EtOAc (50 mL×3) and dried over Na₂SO₄. After removal of EtOAc under reduced pressure, the residue was purified by silica gel (EtOAc:n-Hexane=2:1) to give 23.

(E)-3-(6-Hydroxy-5-methoxybenzofuran-5-yl)-4-ethyl acrylate (23)

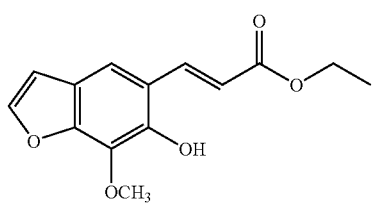

23

¹H-NMR (500 MHz, CDCl₃) δ8.03 (1H, d, J=16.0 Hz), 7.51 (1H, d, J=2.0 Hz), 7.35 (1H, s), 6.68 (1H, d, J=2.0 Hz), 6.63 (1H, d, J=16.5 Hz), 4.29 (2H, q, J=7.1 Hz), 4.21 (3H, s), 1.33 (3H, t, J=7.2 Hz).

General Procedure for the Preparation of 24

To the mixture of 23 (1.96 mmol) and K₂CO₃ (4.9 mmol) in acetone (20 mL) was added appropriate benzyl bromide (3.92 mmol), the resulting solution was refluxed under nitrogen overnight. After filteration to remove K₂CO₃, the filtrate was condensed under reducted pressure and then diluted with EtOAc (50 mL), washed with dis-H₂O (25 mL×3) and dried over Na₂SO₄. After removal of EtOAc under reduced pressure, the residue was purified by silica gel (EtOAc:n-Hexane=1:10) to give 24.

(E)-3-[6-(4-Bromobenzoxy)-5-methoxybenzofuran-5-yl]-4-ethyl acrylate (24a)

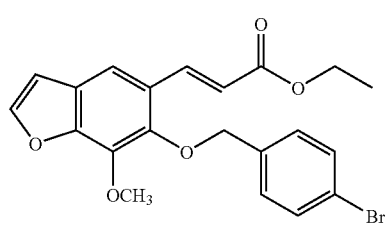

24a

¹H-NMR (500 MHz, CDCl₃) δ 8.00 (1H, d, J=16.1 Hz), 7.60 (1H, d, J=2.0 Hz), 7.50 (2H, d, J=8.3 Hz), 7.43 (1H, s), 7.35 (2H, d, J=8.3 Hz), 6.72 (1H, d, J=2.0 Hz), 6.41 (1H, d, J=16.1 Hz), 5.00 (2H, s), 4.27 (2H, q, J=7.0 Hz), 4.17 (3H, s), 1.34 (3H, t, J=7.1 Hz).

(E)-3-[6-(4-Chlorobenzoxy)-5-methoxybenzofuran-5-yl]-4-ethyl acrylate (24b)

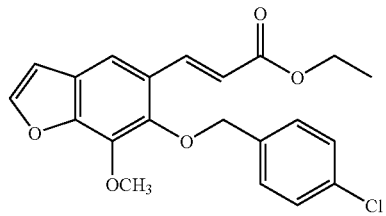

24b

¹H-NMR (500 MHz, CDCl₃) δ 8.00 (1H, d, J=16.0 Hz), 7.61 (1H, d, J=2.5 Hz), 7.44 (1H, s), 7.41 (2H, d, J=8.0 Hz), 7.34 (2H, d, J=8.0 Hz), 6.73 (1H, d, J=2.0 Hz), 6.41 (1H, d, J=16.0 Hz), 5.02 (2H, s), 4.27 (2H, q, J=7.0 Hz), 4.18 (3H, s), 1.34 (3H, t, J=7.0 Hz).

General Procedure for the Preparation of 25

The mixture of 24 (1.68 mmol) and 10% KOH/MeOH (20 mL) was refluxed for 6 hour under N₂ and then diluted with dis-H₂O (100 mL), acidified with 2N HCl to pH 2~3 and extracted with EtOAc (50 mL×3), respectively. The combined EtOAc layer was dried over Na₂SO₄ and concentrated under reduced pressure to give 25.

(E)-3-[6-(4-Bromobenzoxy)-5-methoxybenzofuran-5-yl]acrylate (25a)

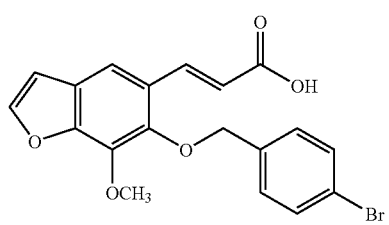

25a

¹H-NMR (500 MHz, d₆-acetone): δ 8.02 (1H, d, J=16.1 Hz), 7.89 (1H, d, J=2.1 Hz), 7.79 (1H, s), 7.58 (2H, d, J=8.3 Hz), 7.49 (2H, d, J=8.2 Hz), 6.92 (1H, d, J=2.1 Hz), 6.50 (1H, d, J=16.0 Hz), 5.10 (2H, s), 4.19 (3H, s)

(E)-3-[6-(4-Chlorobenzoxy)-5-methoxybenzofuran-5-yl]-acrylate (25b)

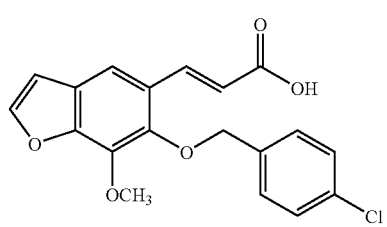

25b

¹H-NMR (500 MHz, CDCl₃): δ 8.11 (1H, d, J=16.0 Hz), 7.63 (1H, d, J=2.0 Hz), 7.48 (1H, s), 7.41 (2H, d, J=8.5 Hz), 7.36 (2H, d, J=8.0 Hz), 6.75 (1H, d, J=2.0 Hz), 6.44 (1H, d, J=16.0 Hz), 5.04 (2H, s), 4.19 (3H, s)

General Procedure for the Preparation of 26

To a solution of potassium hydroxide (379 mg, 6.76 mmol) in MeOH (1.8 mL) was added hydroxylamine hydrochloride (470 mg, 6.76 mmol) in MeOH (4.7 mL) dropwise for 1 h. Filtration to remove the white salt gave the free hydroxylame in MeOH solution. To the mixture of 25 (1.69 mmol) in dry THF (25 mL) was added ethyl chloroformat (0.3 mL, 2.62 mmol) and triethylamine (0.4 mL, 6.38 mmol) and stirred at for 0.5 h and then added the prepared free hydroxylamine solution under N₂. After reaction for 2 h, the reaction mixture was diluted with dis-H₂O (100 mL), acidified with 1N HCl to pH 2~3 and extracted with EtOAc (50 mL×3), respectively. The combined EtOAc layer was dried over Na₂SO₄ and concentrated under reduced pressure to give residue. The residue was purified by silica gel (EtOAc:n-Hexane=1:1) to give 26.

(E)-3-[6-(4-Bromobenzoxy)-5-Methoxybenzofuran-5-yl]-N-hydroxyacrylmide (26a)

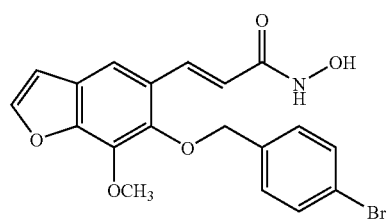

26a

¹H-NMR (500 MHz, CD₃OD) δ 7.92 (1H, d, J=16.0 Hz), 7.75 (1H, d, J=2.0 Hz), 7.50 (2H, d, J=8.0 Hz), 7.47 (1H, s), 7.39 (2H, d, J=8.0 Hz), 6.81 (1H, d, J=2.0 Hz), 6.43 (1H, d, J=16.0 Hz), 5.07 (2H, s), 4.14 (3H, s)

(E)-3-[6-(4-Chlorobenzoxy)-5-Methoxybenzofuran-5-yl]-N-hydroxyacrylmide (26b)

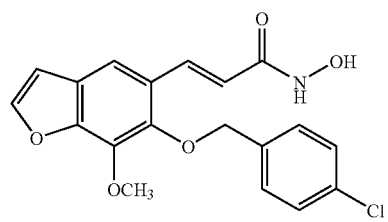

26b

¹H-NMR (500 MHz, d₆-acetone) δ 7.96 (1H, d, J=15.8 Hz), 7.83 (1H, d, J=2.0 Hz), 7.53 (2H, d, J=8.1 Hz), 7.52 (1H, s), 7.38 (2H, d, J=8.1 Hz), 6.85 (1H, d, J=2.0 Hz), 6.59 (1H, d, J=15.5 Hz), 5.05 (2H, s), 4.15 (3H, s)

Scheme 8

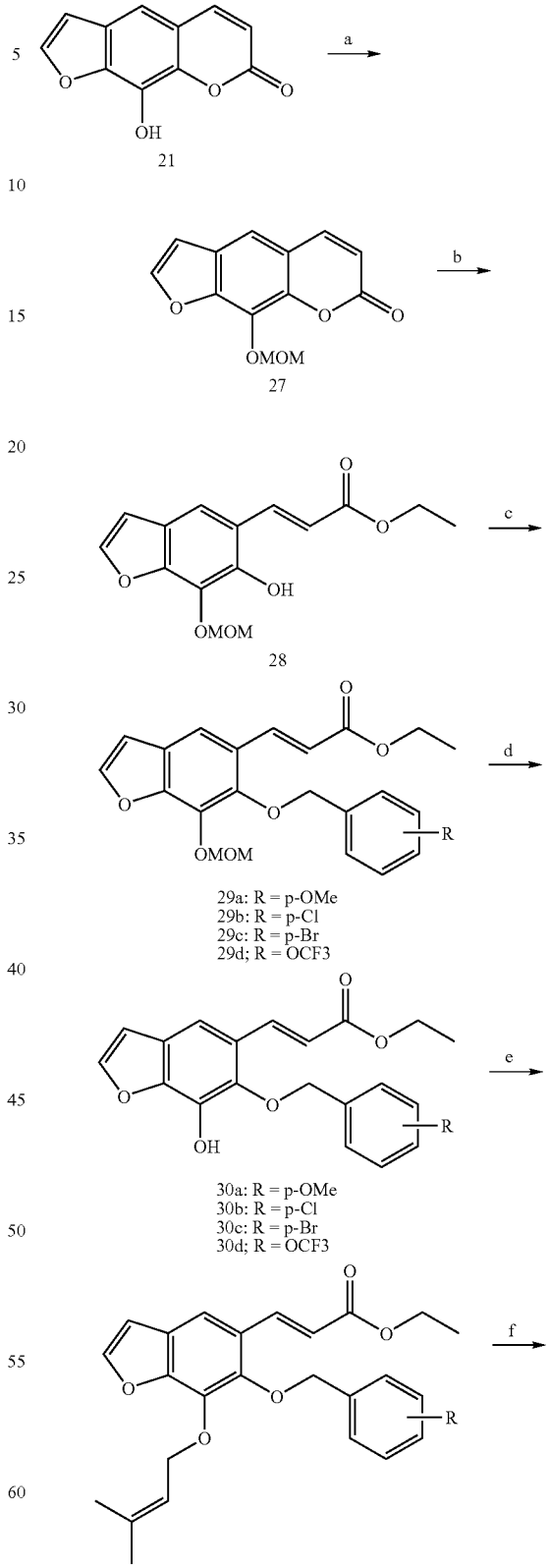

-continued

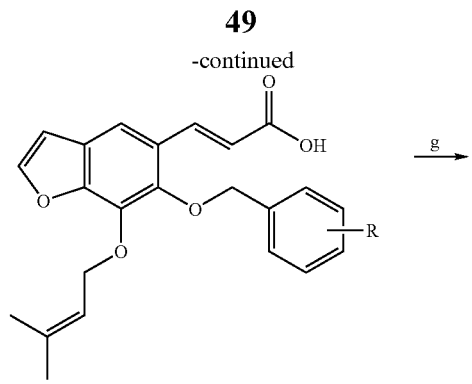

32a: R = p-OMe
32b: R = p-Cl
32c: R = p-Br
32d; R = OCF3

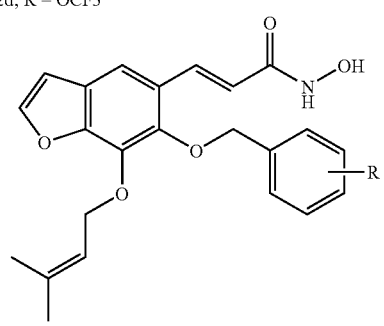

33a: R = p-OMe
33b: R = p-Cl
33c: R = p-Br
33d; R = OCF3

Reagents and conditions:: (a) MOMCl, K₂CO₃, acetone, rt; (b)NaOEt, EtOH, N₂ Δ; (c) K₂CO₃, acetone, Δ; (d) HCl, MeOH, rt; (e) (CH₃)₂(CH)₂CH₂Br, K₂CO₃, acetone, Δ; (f) KOH, MeOH, Δ; (g)NH₂OH, ClCO₂Et, EtOH; (e) DCC, HOBT, THF, rt.

8-Methoxymethyl-xanthotoxol (27)

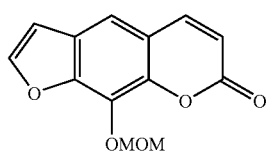

To the mixture of xanthotoxol (21), $K_2CO_3$ (2.5 eq.) and acetone was added MOMCl (2 eq.), the resulting solution was stirred at room temperature for 12 h. After removal of acetone, the residue was diluted with EtOAc, washed with dis-$H_2O$ and dried over $Na_2SO_4$. The EtOAC layer was concentrated under reduced pressure. The residue was subjected to silica gel chromatography to give 27.

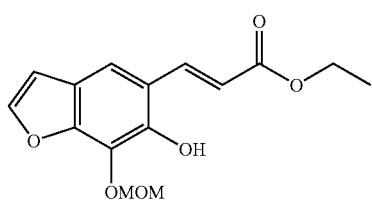

Following the procedure similar to that of 13 gave 28.

29

General Procedure for the Preparation of 29

Following the procedure similar to that of 14 gave 29.

30

General Procedure for the Preparation of 30

To the mixture of 29 and MeOH was added 37% HCl(aq), the resulting solution was stirred at rt for 2 h, then diluted with dis-H2O and extracted with EtOAc. The combined organic layer was dried over $Na_2SO_4$ and concentrated under reduced pressure. The residue was subjected to silica gel to give 30.

31

General Procedure for the Preparation of 31

To the mixture of 30, K2CO3 (2.5 eq.) and acetone was added isoprenyl bromide (2 eq.), the resulting solution was stirred at room temperature for 24 h. After removal of acetone, the residue was diluted with EtOAc, washed with dis-$H_2O$ and dried over $Na_2SO_4$. The EtOAC layer was concentrated under reduced pressure. The residue was subjected to silica gel chromatography to give 31.

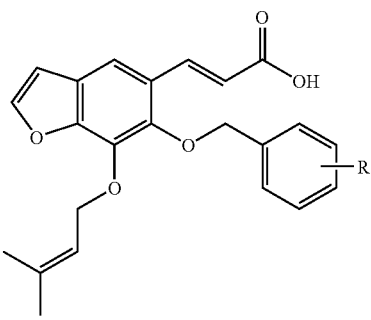

32

General Procedure for the Preparation of 32
Following the procedure described as 3 gave 32.

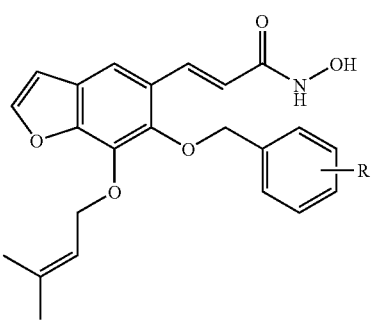

33

General Procedure for the Preparation of 33
Following the procedure described as 4 gave 33.

Salts

Pharmaceutically acceptable salts of the compounds of the present invention can be prepared by any conventional means. Exemplified processes for synthesizing the salts are provided below.

(E)-2-(4-Methoxybenzoxy)-4-methoxy-3-prenyl-N-hydroxycinamide lysine salt

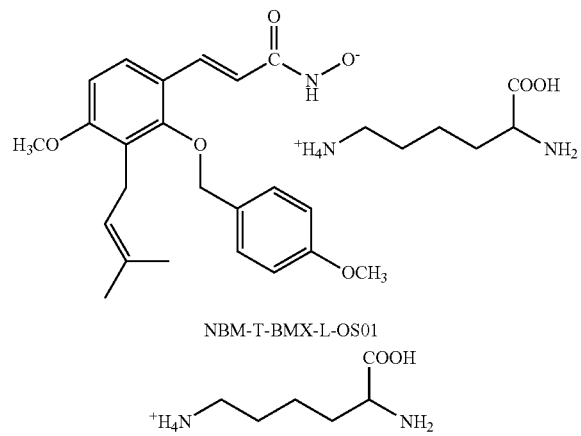

NBM-T-BMX-L-OS01

To the mixture of hydroxamate (1 mmole) and EtOH (15 mL) was added a solution of L-lysine (1 mmole) in H$_2$O (10 mL). The resultant was stirred at 40° C. for 4 h, cooled to room temperature, then stirred for additional 12 h. The solvent was removed under reduced pressure and the residue was precipitate from EtOH. After filtration, the solid was wash with dis-H$_2$O and dried in a vacuum oven.

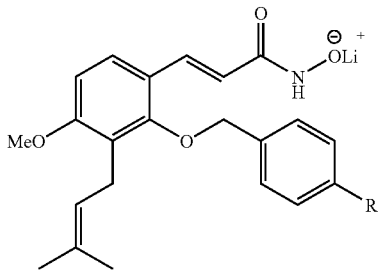

R = OCF$_3$  T-L-BTX
  = OMe    T-L-BMX
  = Br     T-L-BBX
  = Cl     T-L-BCX

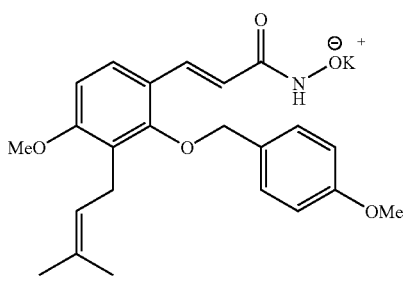

T-K-BMX

To the mixture of hydroxamate (1 mmole) and EtOH (15 mL) was added a solution of lithium hydroxide or potassium hydroxide (1.2 mmole) in H$_2$O (5 mL). The resultant was stirred at room temperature overnight. The solvent was removed under reduced pressure and the residue was precipitate from EtOH. After filtration, the solid was wash with dis-H$_2$O and dried in a vacuum oven.

Pharmaceutical Composition of the Invention

The compounds of formula (I) and pharmaceutically acceptable salts, stereoisomers, enantiomers, prodrugs and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 10 to 30 wt % (percent by weight), more preferably from 30 to 50 wt %, still more preferably from 50 to 70 wt %, and even more preferably from 70 to 100 wt %, of the active ingredient, all percentages by weight being based on total composition. In addition, the pharmaceutical composition of the invention may further comprise other agents for the prevention or treatment of diseases associated with histone deacetylase (HDAC).

The pharmaceutical compositions may be administered systemically, e.g., by oral administration in the form of tablets, capsules, syrups, powders or granules; or by parenteral administration in the form of solutions or suspensions; or by subcutaneous administration; or by rectal administration in the form of suppositories; or transdermally.

The compounds and pharmaceutical compositions of the invention are an HDAC inhibitor and can be retained long in the cells and continuously induce the acetylation of histone H4. They are HDAC inhibitors inducing differentiation of cells and neural stem cells. In addition, the compounds of the invention significantly inhibit HDAC activity. The compounds of the invention significantly decrease both S and G2/M phases of the cells in a dose-dependent manner and change the morphology of cancer cells. Therefore, the compounds of the invention can treat tumor or cell proliferative disease. Moreover, the compounds of the invention can enhance the neurite outgrowth and treat neurodegenerative diseases (such as Huntington's disease and poly-glutamine disease) and human spinal muscular atrophy (SMA).

EXAMPLE

The following examples illustrate preferred methods for synthesizing and using the compounds:

Example 1

Preparation of 2-(4-Nitrobenzoxy)-4-methoxy-3-prenyl-4-nitrobenzyl cinamate

To the mixture of 1 (2 g, 8.20 mmol) and potassium t-butoxide (1.84 g, 16.4 mmol) in dry DMF (20 mL) were added various benzyl chlorides (16.4 mmol), and the resulting solution was stirred at room temperature under nitrogen for 6 h and then diluted with EtOAc (50 mL), washed with dis-$H_2O$ (25 mL×3) and dried over $Na_2SO_4$. After removal of EtOAC under reduced pressure, the residue was purified by silica gel (EtOAc:n-Hexane=1:10~1:1) to give the title compound: $^1$H-NMR (400 MHz, CDCl$_3$) 8.24-8.22 (4H, m), 7.59-7.46 (4H, m), 7.45 (1H, d, J=8.6 Hz), 6.98 (1H, d, J=12.3 Hz), 6.69 (1H, d, J=8.6 Hz), 5.81 (1H, d, J=12.3 Hz), 5.12 (1H, t, J=6.5 Hz), 4.91 (2H, s), 4.64 (2H, s), 3.85 (3H, s), 3.32 (2H, d, J=6.6 Hz), 1.61 (3H, s), 1.57 (3H, s).

Example 2

Preparation of 2-Benzoxy-4-methoxy-3-prenyl cinamate

The mixture of 2 (11.36 mmol) and 10% KOH/MeOH (40 mL) was refluxed overnight under $N_2$ and then diluted with dis-$H_2O$ (100 mL), acidified with 2N HCl to pH 5-6 and extracted with EtOAC (50 mL×3). The combined EtOAc layer was dried over $Na_2SO_4$ and concentrated under reduced pressure. The residual was purified by silica gel (EtOAc:n-Hexane=1:2) to give the title compound: $^1$H-NMR (400 MHz, CDCl$_3$) 7.63 (1H, d, J=8.6 Hz), 7.42-7.26 (5H, m), 7.25 (1H, d, J=12.5 Hz), 6.80 (1H, d, J=8.7 Hz), 5.88 (1H, d, J=12.5 Hz), 5.16 (1H, t, J=6.6 Hz), 4.82 (2H, s), 3.85 (3H, s), 3.36 (2H, d, J=6.7 Hz), 1.65 (3H, s), 1.62 (3H, s). ESIMS m/z [M-H]$^-$ 351.13 (100).

Example 3

Preparation of 2-Benzoxy-4-methoxy-3-prenyl-N-hydroxy cinnamamide

To a solution of potassium hydroxide (637 mg, 11.36 mmol) in MeOH (4 mL) was added hydroxylamine hydrochloride (790 mg, 11.36 mmol) dropwise, and then the solution was stirred in an ice bath for 1 h. Filtration was performed to remove the white salt to give free hydroxylame in MeOH solution. To the mixture of 3a (1 g, 2.84 mmol) in dry THF (25 mL) were added ethyl chloroformat (0.6 mL, 5.68 mmol) and triethylamine (0.6 mL, 5.68 mmol), the mixture was stirred for 0.5 h, and then the prepared free hydroxylamine solution was added. After reaction for 3 h, the reaction mixture was concentrated under reduced pressure to give residual. The residual was purified by silica gel (EtOAc:n-Hexane=1:2) to give the title compound: $^1$H-NMR (400 MHz, CDCl$_3$) 7.40-7.33 (5H, m), 7.30 (1H, d, J=8.6 Hz), 7.24 (1H, d, J=8.7 Hz), 7.01 (1H, d, J=12.5 Hz), 6.66 (1H, d, J=8.7 Hz), 5.79 (1H, d, J=12.4 Hz), 5.17 (1H, t. J=6.6 Hz), 4.82 (2H, s), 3.83 (3H, s), 3.37 (2H, d, J=6.7 Hz), 1.69 (3H, s), 1.66 (3H, s); $^{13}$C-NMR (100 MHz, CDCl$_3$) 159.7 (s), 159.2 (s), 155.9 (s), 136.9 (s), 135.9 (d), 131.8 (s), 128.6 (d), 128.5 (d), 128.2 (d), 128.1 (d), 128.0 (d), 123.9 (s), 122.7 (d), 121.1 (s), 118.2 (d), 106.8 (d), 76.6 (t), 55.7 (q), 25.7 (q), 23.2 (t), 17.9 (q), 14.4 (q); ESIMS m/z [M+H]$^+$ 368.13 (100).

Example 4

Preparation of 2-Benzoxy-4-methoxy-3-(2-Hydroxy-2-methylbutyl)-N-hydroxy cinnamamide To a solution of 4a (100 mg, 0.27 mmol) in THF (15 mL) was added 49% $H_2SO_4$ (10 mL) and the solution was stirred at room temperature for 6 hours. The resulting solution was extracted with $CH_2Cl_2$ (50 mL×3) and then dried over $Na_2SO_4$ to give residue. The residue was purified by silica gel (EtOAc:n-Hexane=1:1) to give the title compound: $^1$H-NMR (400 MHz, CDCl$_3$) 7.40-7.33 (5H, m), 7.30 (1H, d, J=8.6 Hz), 7.00 (1H, d, J=12.4 Hz), 6.69 (1H, d, J=8.6 Hz), 5.89 (1H, d, J=12.4 Hz), 4.83 (2H, s), 3.82 (3H, s), 2.66 (2H, t, J=7.8 Hz), 1.65 (2H, t, J=7.8 Hz), 1.16 (6H, s).

Example 5

Preparation of 2-Benzoxy-4-methoxy-3-prenyl-N-(2-aminophenyl)cinamamide

The mixture of 3 (17.04 mmol), HOBT (2.76 g, 20.44 mmol) and DCC (4.22 g, 20.44 mmol) in dry THF (30 mL) was stirred at room temperature for 0.5 h and then o-phenylenediamine (1.84 g, 17.04 mmol) was added. The resulting solution was continuously stirred overnight and then concentrated under reduced pressure to give residue. The residue was dissolved in $CH_2Cl_2$ (50 ml), washed with saturated $NaHCO_3$ (25 mL×3), and dried over $Na_2SO_4$. The organic layer was evaporated under reduced pressure and then purified by silica gel (EtOAc:n-Hexane=1:3-1:1) to give the title compound: $^1$H-NMR (400 MHz, CDCl$_3$) 7.43-7.38 (5H, m), 7.37 (1H, d, J=8.6 Hz), 7.26 (1H, d, J=8.7 Hz), 7.03 (1H, d, J=12.5 Hz), 7.01-7.02 (2H, m), 6.74-6.72 (2H, m), 6.68 (1H, d, J=8.6 Hz), 6.06 (1H, d, J=12.4 Hz), 5.14 (1H, t. J=6.6 Hz), 4.90 (2H, s), 3.84 (3H, s), 3.65 (2H, s), 3.38 (2H, d, J=6.5 Hz), 1.72 (3H, s), 1.65 (3H, s).

Example 6

Preparation of 2-Benzoxy-4-methoxy-3-(2-Hydroxy-2-methylbutyl)-benzyl cinamamate To a solution of 2 (0.27 mmol) in THF (15 mL) was added 49% $H_2SO_4$ (10 mL) and the solution was stirred at room temperature for 6 h. The resulting solution was extracted with $CH_2Cl_2$ (50 mL×3) and then dried over $Na_2SO_4$ to give residue. The residue was purified by silica gel (EtOAc:n-Hexane=1:1) give the title compound: $^1$H-NMR (400 MHz, CDCl$_3$) 7.38 (1H, d, J=8.7 Hz), 7.36-7.27 (10H, m), 7.00 (1H, d, J=12.4 Hz), 6.60 (1H, d, J=8.7 Hz), 5.94 (1H, d, J=12.4

Hz), 5.13 (2H, s), 4.81 (2H, s), 3.82 (3H, s), 2.67 (2H, t, J=8.2 Hz), 1.61 (2H, t, J=8.2 Hz), 1.18 (6H, s); ESIMS m/z [M+Na]⁺ 483.6 (100).

Example 7

Inhibition of Cancer Cell Growth by the Compounds of the Invention

Figure 4:
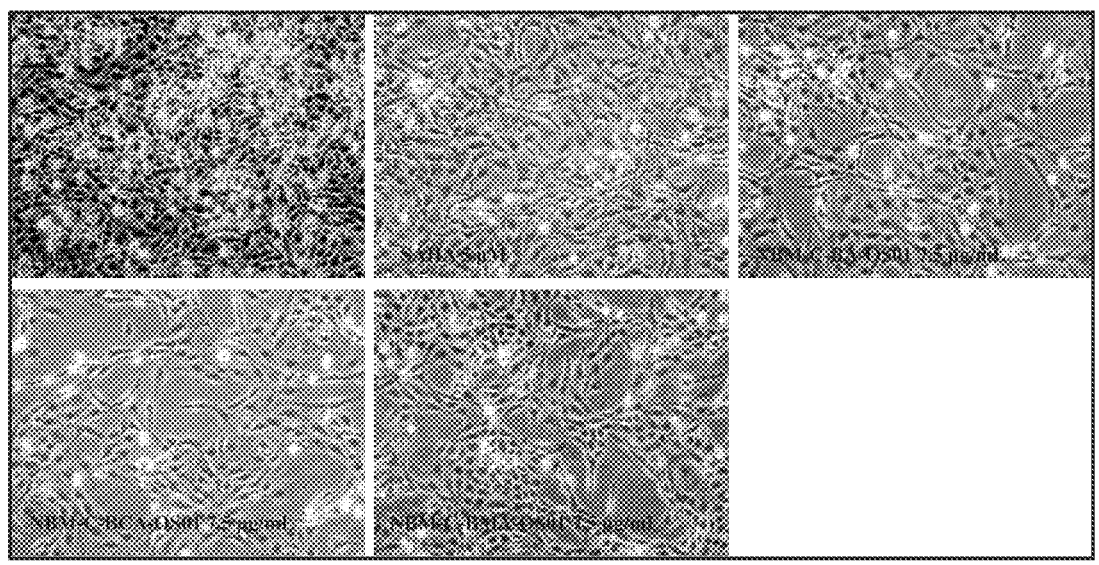
FIG. 4 shows the cell growth inhibition by the treatment of various NBM-C-BA-OS01 derivatives. Treatment of NBM-C-BA-OS01, NBM-C-BCA-OS01 (17d), and NBM-C-BMA-OS01 (17b) of 7.5 μg/mL inhibited the Rat C6 glioma cells growth in 48 hrs.
Figure 5:
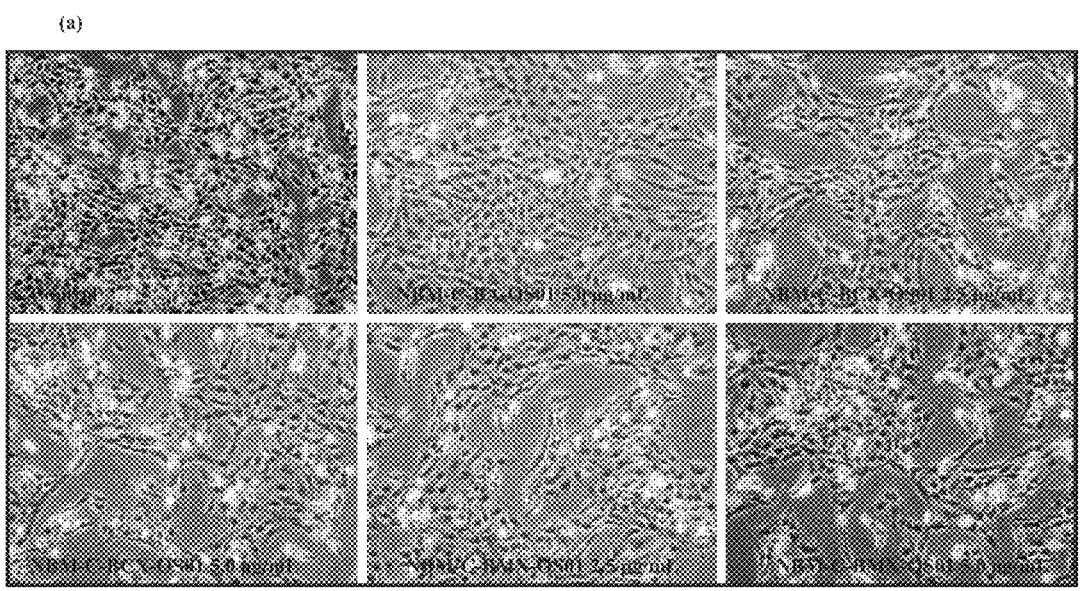
FIG. 5 shows the effect of NBM-HB-OS01 derivatives on the cell growth inhibition.
Figure 5:
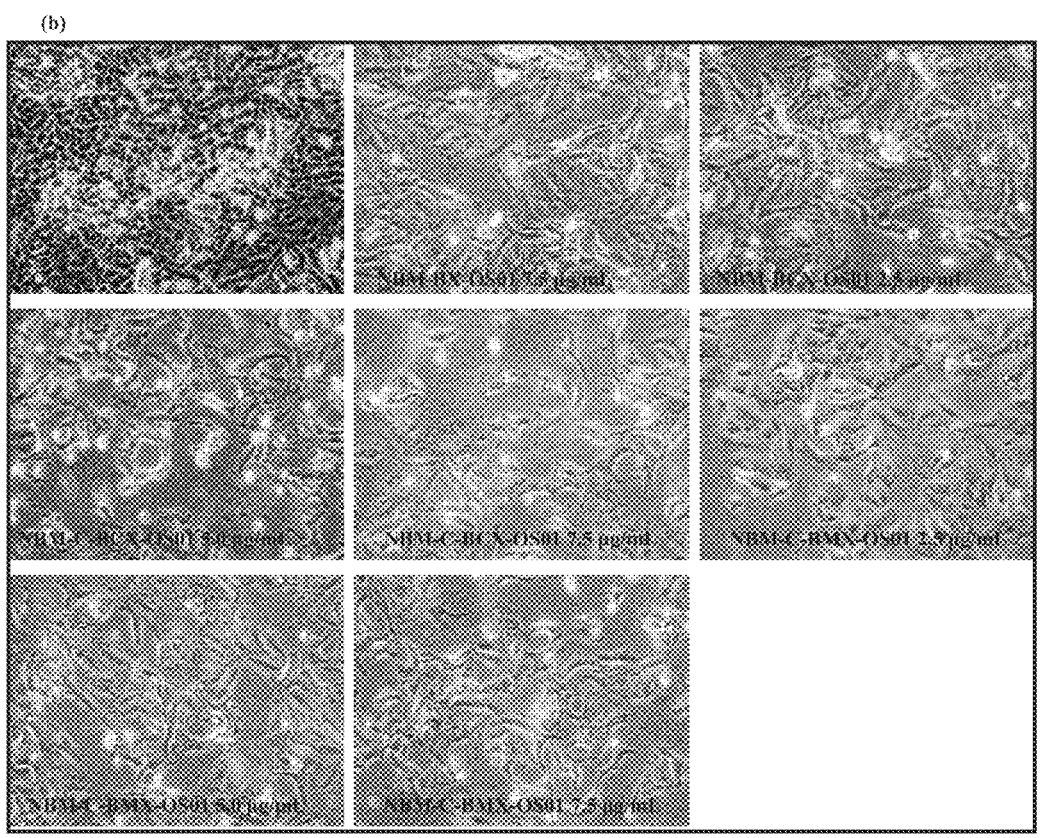
Figure 5:
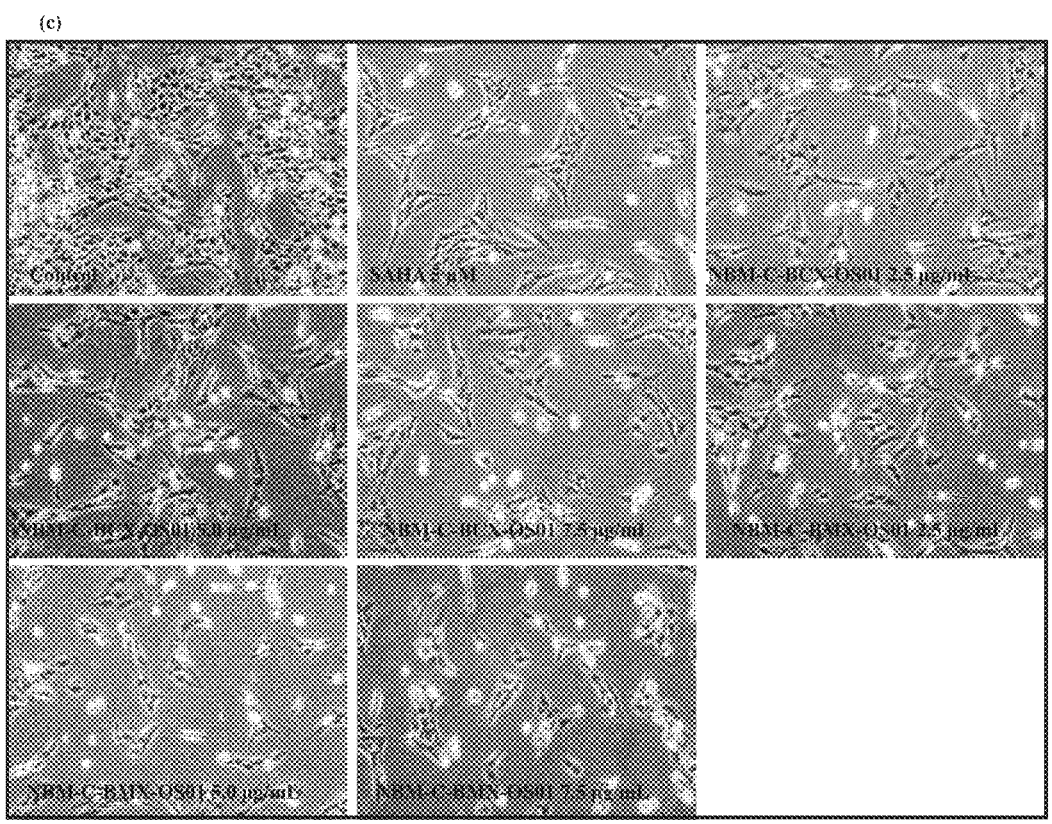
Figure 5:
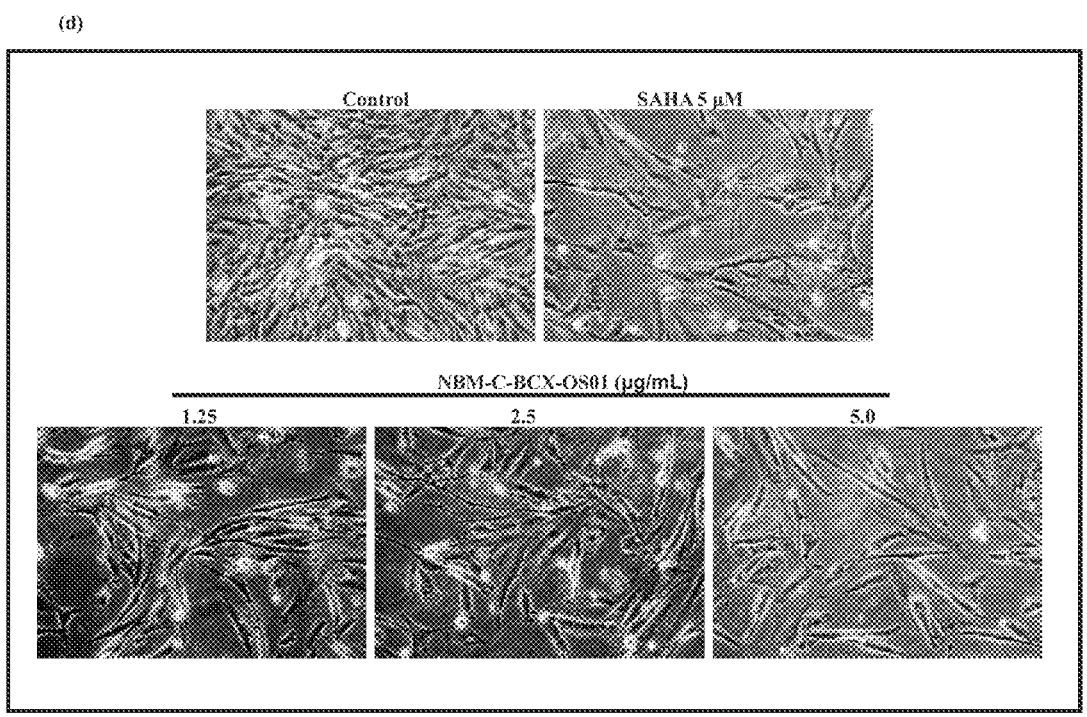
Figure 5:
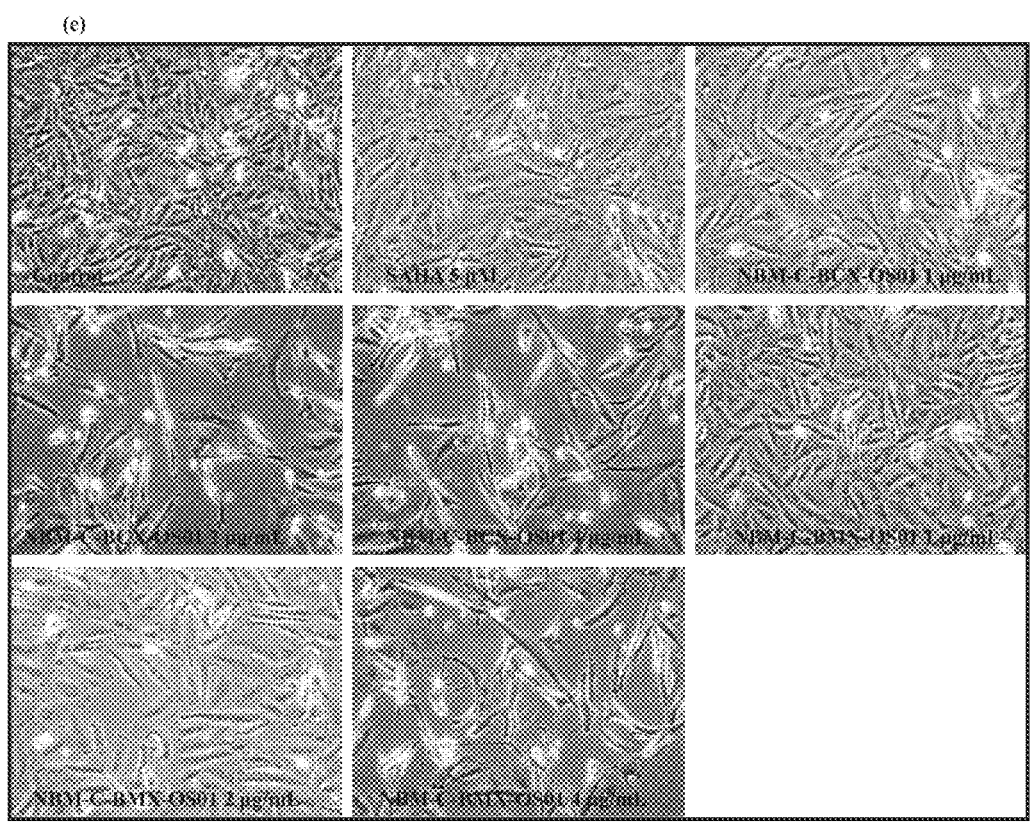
Figure 5:
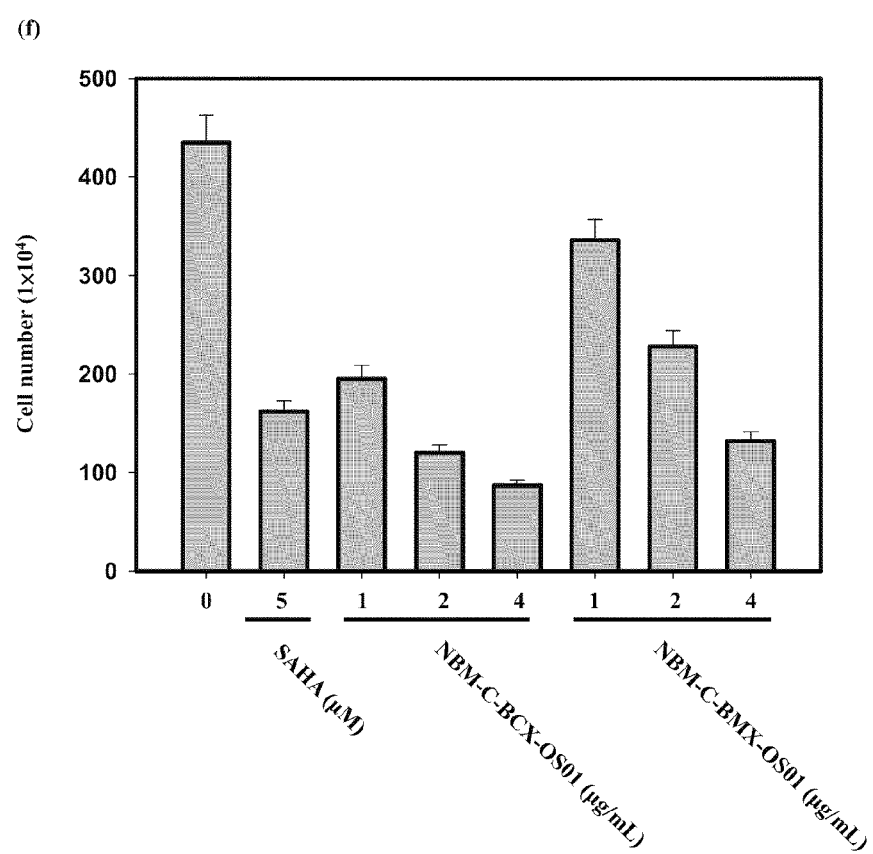

Three cancer cell lines, Rat C6 giloma cells, Human breast cancer MCF-7 cells, and Human lung cancer A549 cells, were cultured in Dulbecco's modified Eagle's medium (DMEM; Gibco) containing 10% fetal bovine serum (FBS) and 1% penicillin/streptomycin. All three cell lines were maintained at 37° C. in a humidified atmosphere of 95% air and 5% $CO_2$. For the experiments, the cells were seeded in 6-well plates. After 24 hours, the cells were treated with different concentrations of the various compounds. The cells were observed at 24, 48, and 72 hours. Inhibition of cancer cell growth of NBM-HB-OS01 in various concentrations after 48 hours in Rat C6 glioma cells (see FIG. 1(a)) or in Human colon cancer HT-29 cells (see FIG. 1(b)) was shown. NBM-C-BX-OS01 arrested the cell growth in various concentrations in Rat C6 glioma cells in 48 hours (see FIG. 2(a)), in human breast cancer MCF-7 cells in 24 hours (see FIG. 2(b)) and in human lung cancer A549 cells in 48 hours (see FIG. 2(c)). Treatments with NBM-C-BA-OS01, NBM-C-BCA-OS01 and NBM-C-BMA-OS01 inhibited the Rat C6 glioma cell growth in a fixed concentration (7.5 μg/mL) in 48 hours (see FIG. 4). NBM-C-BA-OS01 (5 μg/mL), NBM-C-BCX-OS01 (2.5, 5.0 μg/mL), and NBM-C-BMX-OS01 (2.5, 5.0 μg/mL) inhibited the cell growth of Rat C6 glioma cells in 24 hours (see FIG. 5(a)).

Example 8

Figure 3:
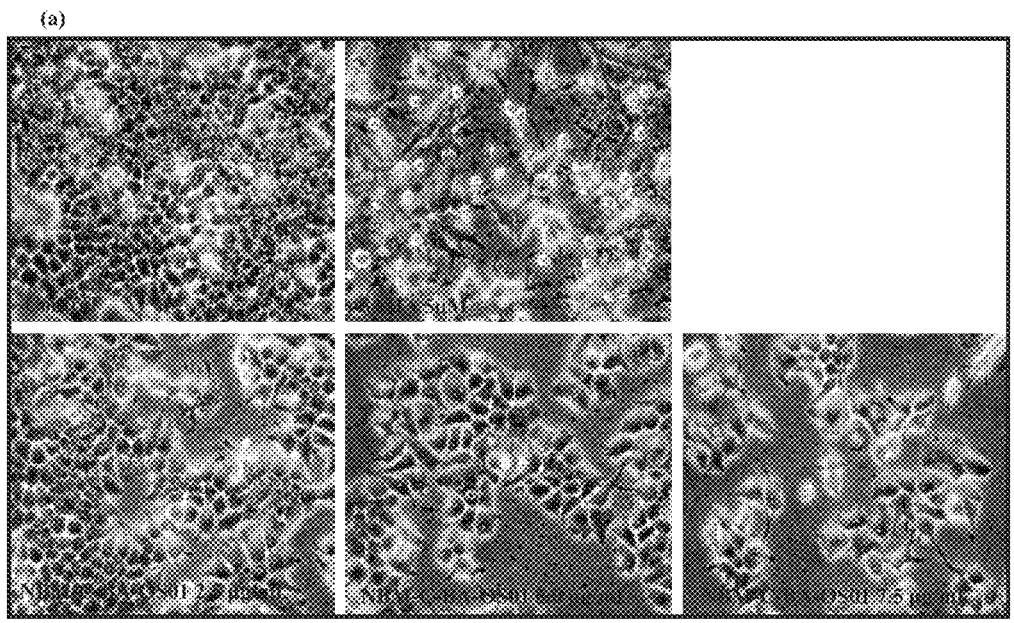
FIG. 3 shows the effect of NBM-C-BA-OS01 (17a) on the inhibition of cells growth of three cancer cell lines. Morphology changes of Human breast cancer MCF-7 cells and Rat C6 glioma cells in response to NBM-C-BA-OS01 (2.5, 5.0, 7.5 μg/mL) for 72 hrs are shown in FIGS. 3(a) and (b). Hyperacetylation of Histone H3 protein was detected by treating Human lung cancer A549 cells for 6 hrs with NBM-C-BA-OS01 of 7.5 μg/mL. The results are shown in FIG. 3(c).
Figure 3:
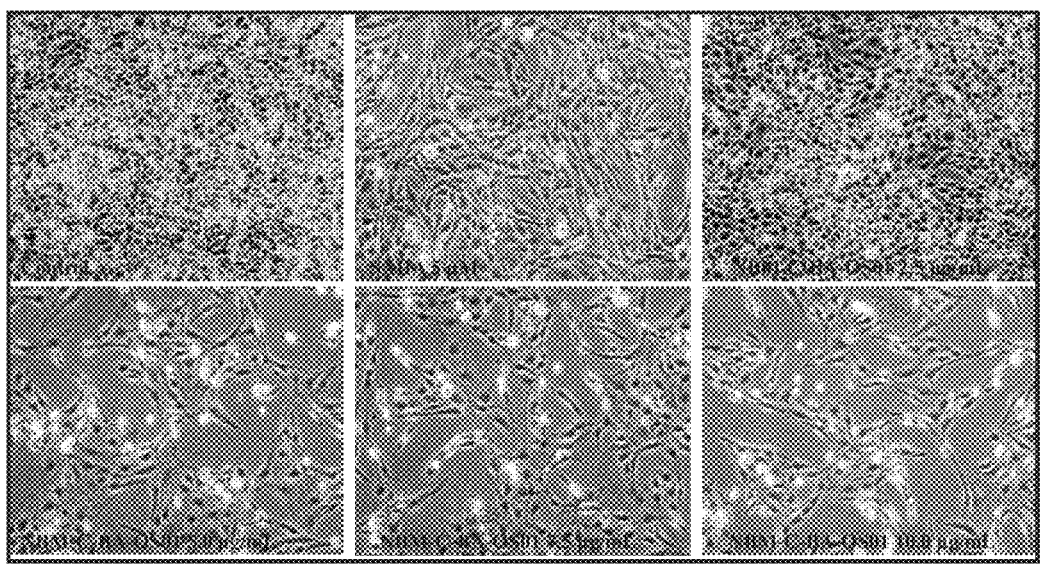
Figure 3:
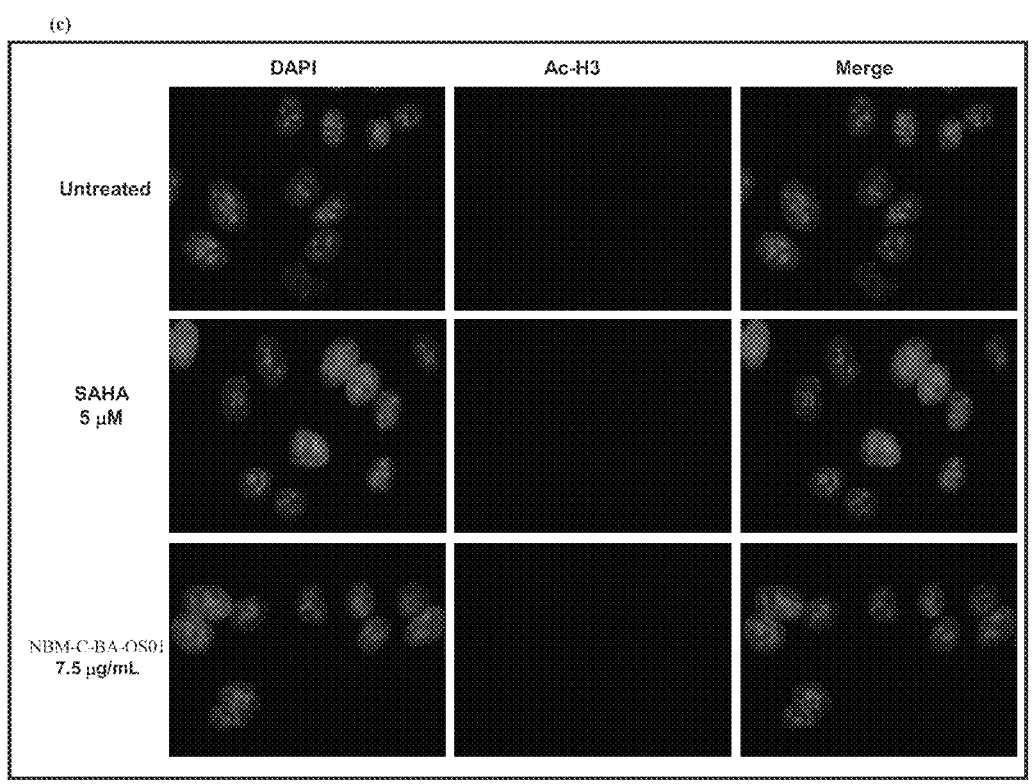
Figure 6:
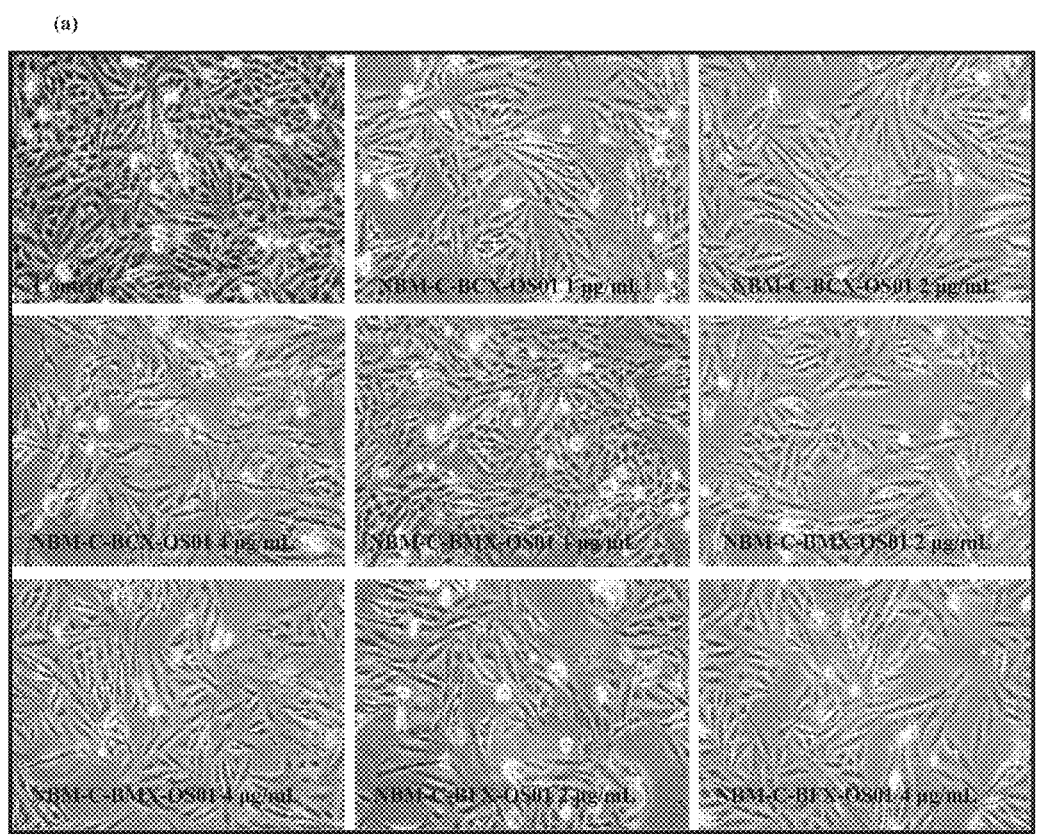
FIG. 6 shows the effects of NBM-HB-OS01 derivatives on the biological activity in various human cancer cell lines.
Figure 6:
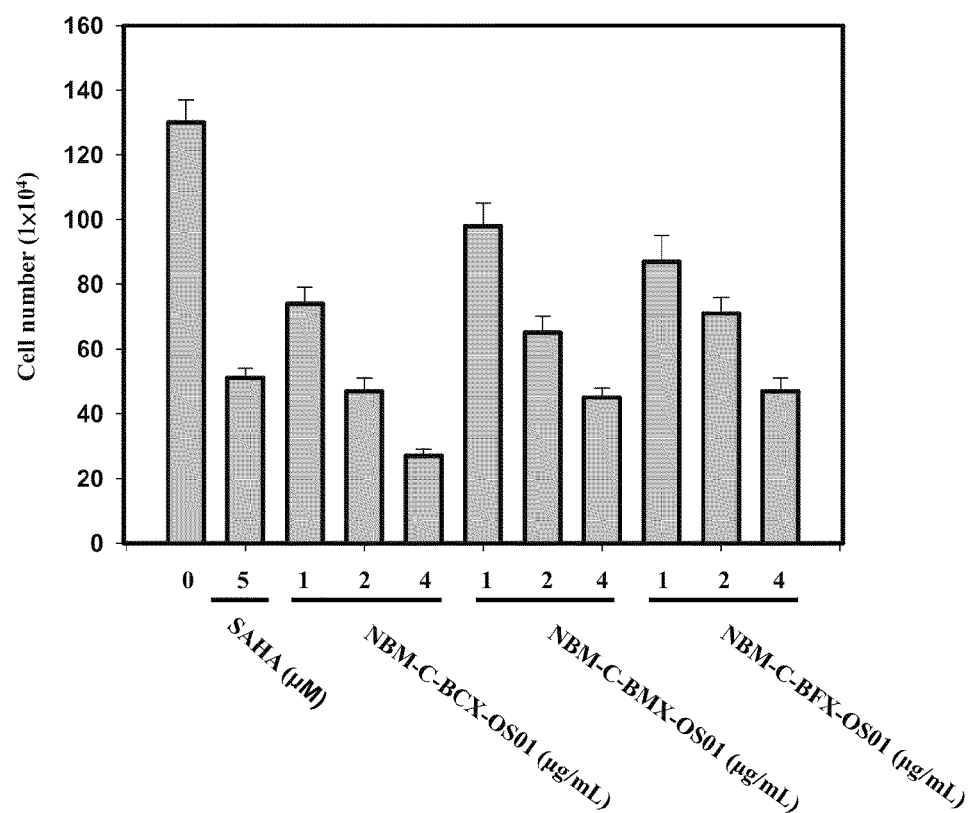
Figure 6:
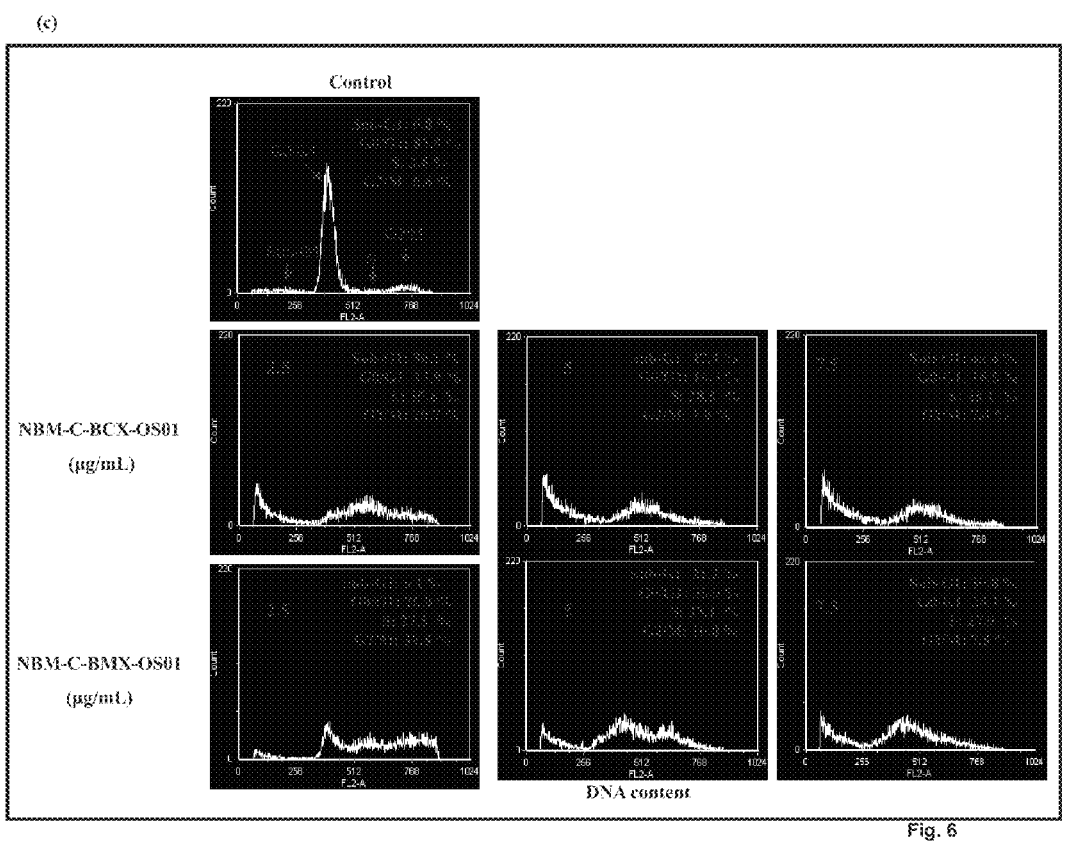
Figure 6:
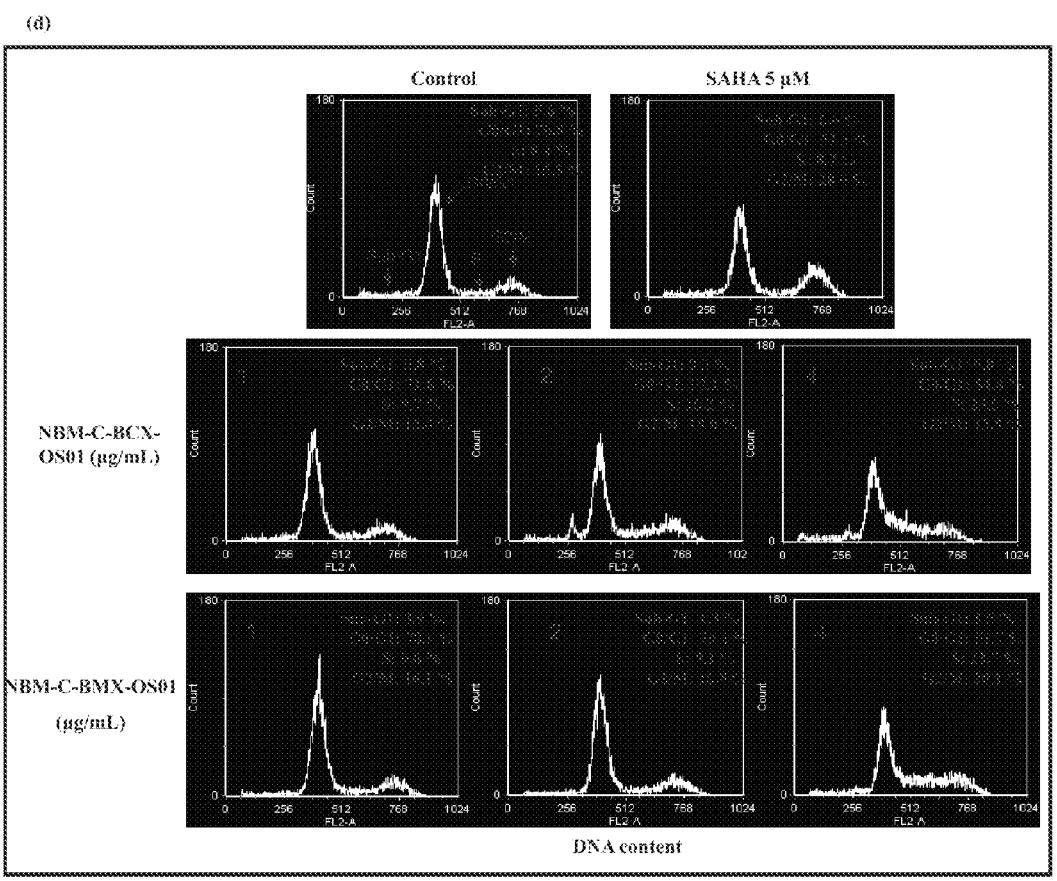
Figure 6:
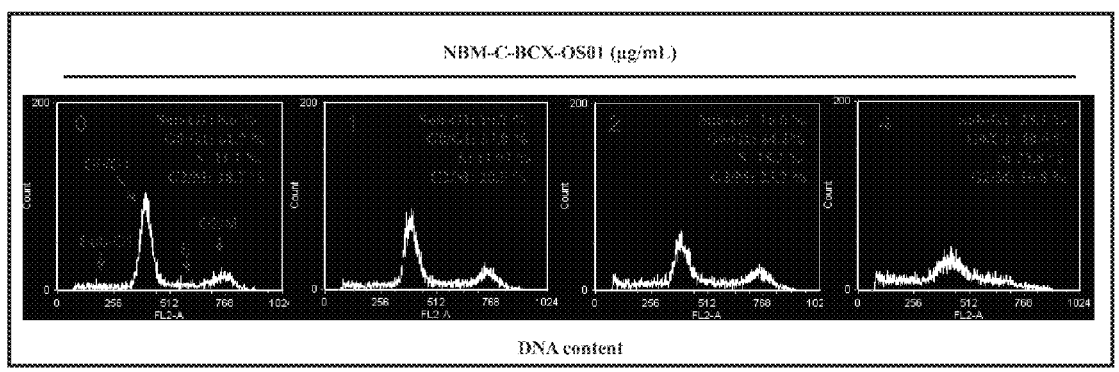

Inhibition of Cancer Cell Growth and Change of the Morphology by the Compounds of the Invention Five cancer cell lines, Rat C6 giloma cells, Human breast cancer MCF-7 cells, Human glioma Hs683 cells, Human glioblastoma 05-MG cells, and Human lung cancer A549 cells, were cultured in Dulbecco's modified Eagle's medium (DMEM; Gibco) containing 10% fetal bovine serum (FBS) and 1% penicillin/streptomycin, and were kept at 37° C. in a humidified atmosphere of 95% air and 5% $CO_2$. Human breast cancer MDA-MB-231 cells were cultured in L-15 medium (Gibco) containing 10% fetal bovine serum (FBS), 1% penicillin/streptomycin, and 2 mM glutamine, and were maintained at 37° C. in a humidified atmosphere of 95% air and 0% $CO_2$. For these experiments, the cells were seeded in 6-well plates or a 60-mm dish. After 24 hours, the cells were treated with different concentrations of the various compounds. The cells were observed at 24, 48 and 72 hours. Human breast cancer MCF-7 cells (see FIG. 3(a)), and Rat C6 glioma cells (see FIG. 3(b)) exhibited changes in morphology in response to NBM-C-BA-OS01 2.5, 5.0, 7.5 μg/mL treatment for 72 hours. Treatments with NBM-C-BX-OS01 (7.5 μg/mL), NBM-C-BCX-OS01 (2.5, 5.0, 7.5 μg/mL) and NBM-C-BMX-OS01 (2.5, 5.0, 7.5 μg/mL) induced A549 cell growth inhibition in dose-dependent amounts for 72 hours (see FIG. 5(b)) and the results were similar to those in Rat C6 glioma cells for 24 hours (see FIG. 5(c)). Human glioma Hs683 cells were treated with NBM-C-BX-OS01 (1.25, 2.5, 5.0 μg/mL) for 72 hours (see FIG. 5(d)). Human glioblastoma 05-MG cells were treated with NBM-C-BCX-OS01 (1.0, 2.0, 4.0 μg/mL) and NBM-C-BMX-OS01 (1.0, 2.0, 4.0 μg/mL) for 72 hours (see FIG. 5(e)). The results obtained by cell counting showed the same tendency (see FIG. 5(f)). NBM-C-BCX-OS01, NBM-C-BMX-OS01 and NBM-C-BFX-OS01 inhibited the growth of human breast cancer MDA-MB-231 cells and changed the morphology of the cells for 72 hours (see FIG. 6(a)). The results were counted by a trypan blue exclusion assay (see FIG. 6(b)).

Example 9

Figure 2:
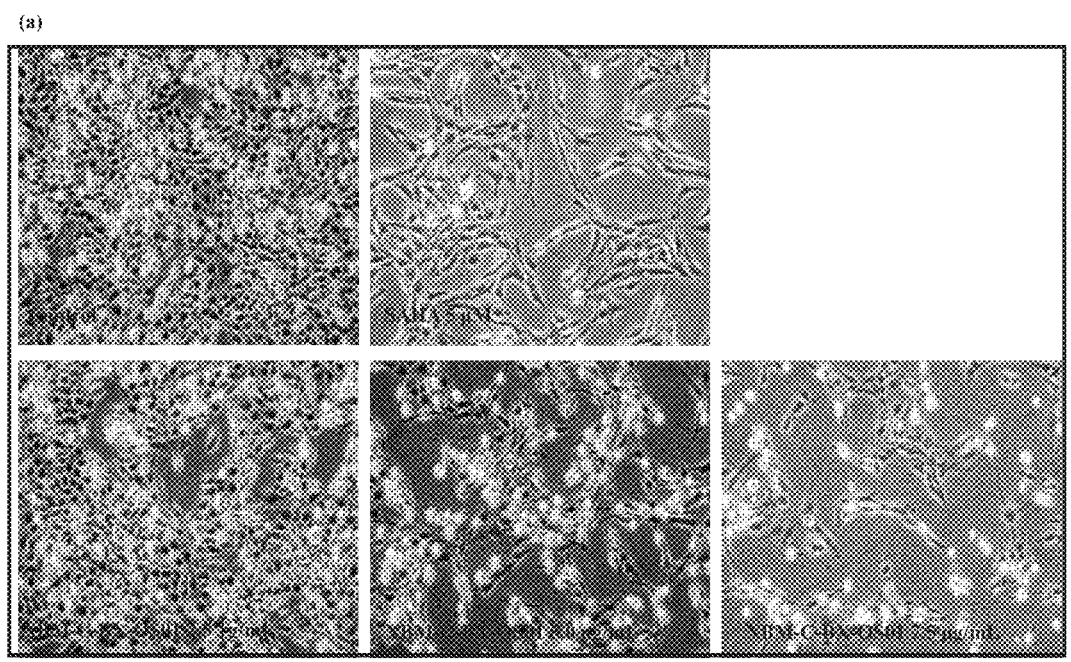
FIG. 2 shows the effects of NBM-C-BX-OS01 (4a) on the inhibition of cells growth of various cancer cell lines. Inhibition of cancer cells growth was shown after treating cell lines with various concentrations of NBM-C-BX-OS01 in Rat C6 glioma cells, Human breast cancer MCF-7 cells for 24 hrs, and Human lung cancer A549 cells for 48 hrs. The results are shown in FIGS. 2(a), (b) and (c), respectively.
Figure 2:
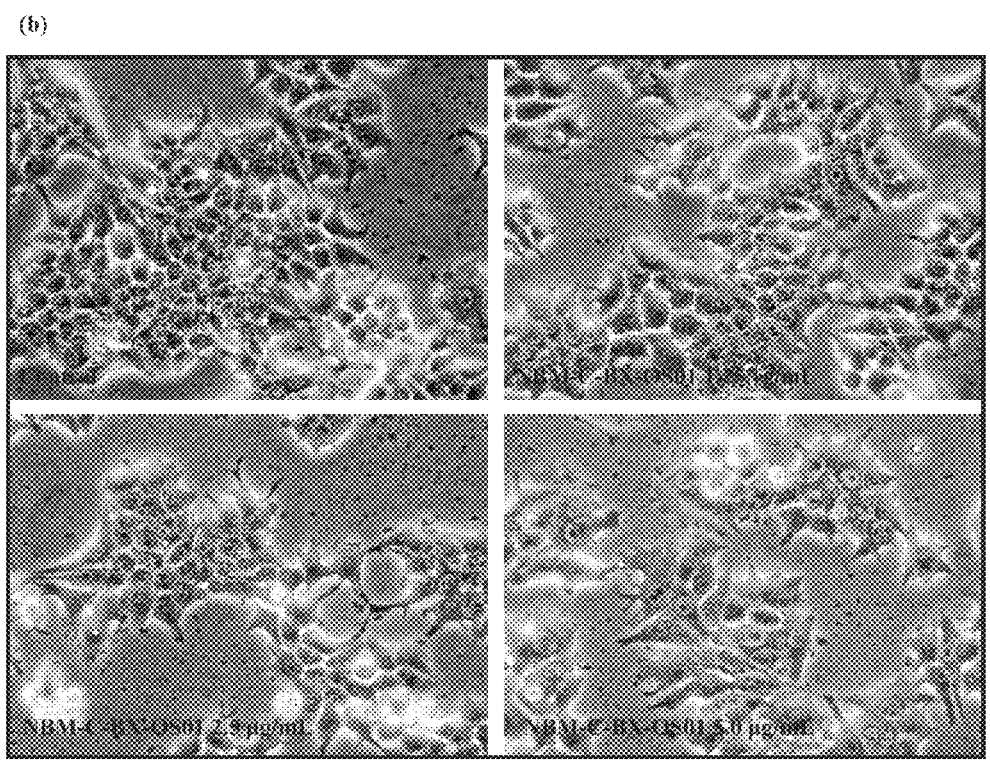
Figure 2:
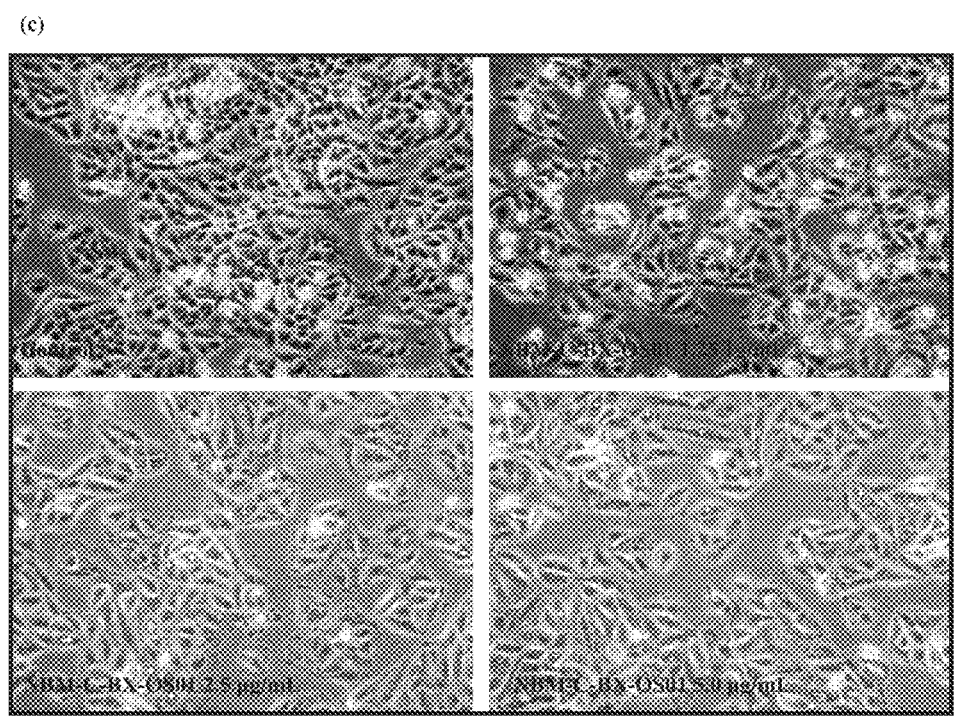
Figure 2:
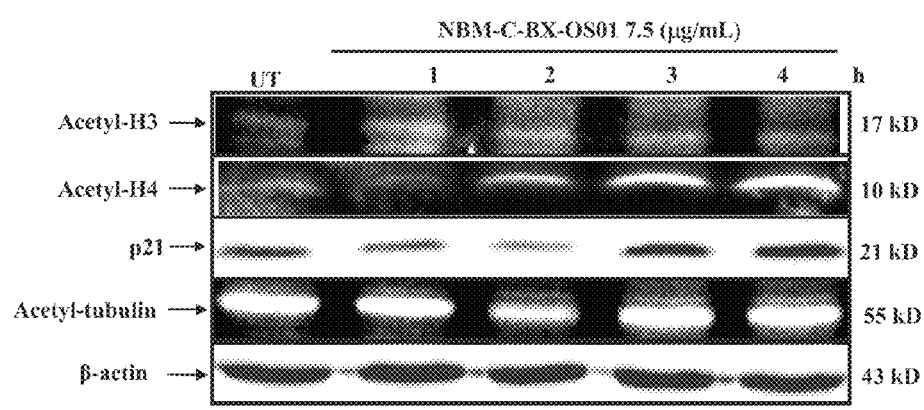
Figure 2:
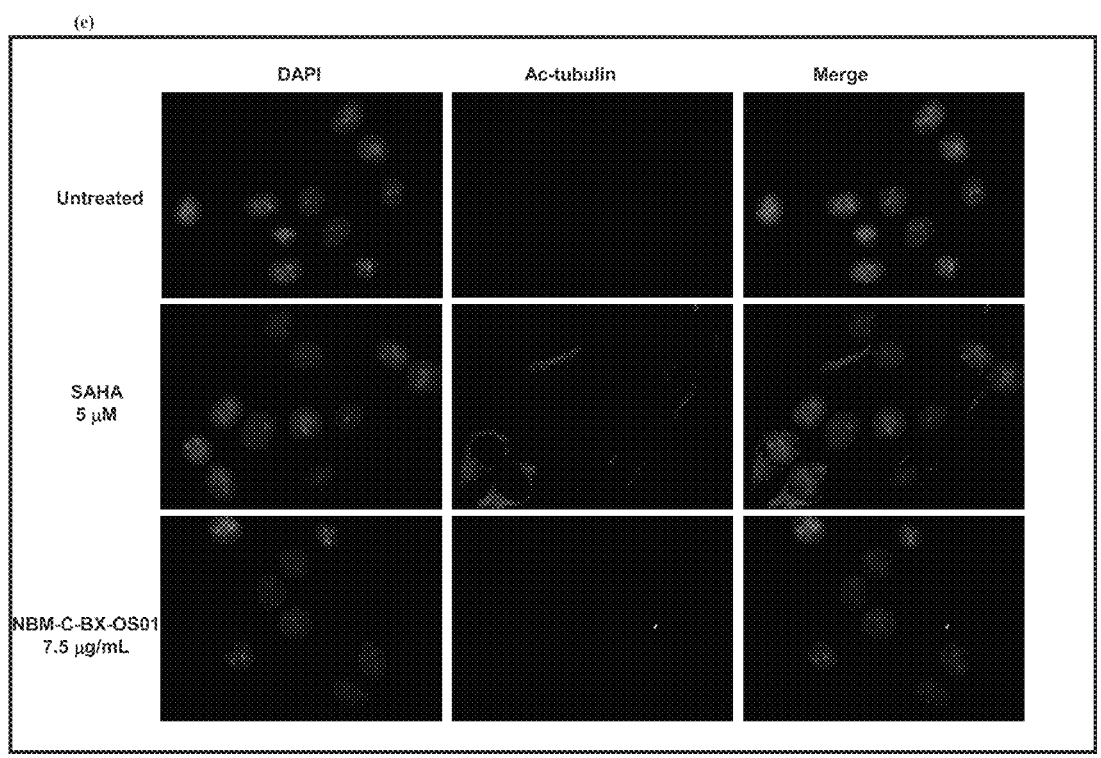

Effects of the Invention (NBM-HB-OS01) on mRNA Expression of Rat C6 Glioma Cells The cell-cycle related mRNA expression was examined by RT-PCR. The total RNA was isolated from the treated Rat C6 glioma cells using the RNeasy Mini Kit (Qiagen) as described by the manufacturer. The cDNA was produced from 500 ng of total RNA using ReverTra-Plus-TM (TOYOBO). The RT product (1 μl) was amplified by PCR with primers for amplification of several genes (p21, cyclin B1, and cyclin D1) for the cell cycle analyses and GAPDH was used as an internal control. Rat C6 glioma cells were treated with NBM-HB-OS01 for 48 hours, and as shown in FIG. 1(d), NBM-HB-OS01 induced p21 mRNA expression.

Example 10

Effects of the Invention on the Cell Cycle of Various Human Cancer Cells

Human lung cancer A549 cells, Human glioma Hs683 cells and Human glioblastoma 05-MG cells were seeded 1×10⁶ cells in a 100-mm dish. After 24 hours of incubation in DMEM+10% BSA, Human lung cancer A549 cells were treated with NBM-HB-OS01 (2.5, 5.0, 7.5, 10.0 μg/mL) for 24 hours and were treated with NBM-C-BCX-OS01 (2.5, 5.0, 7.5 μg/mL) and NBM-C-BMX-OS01 (2.5, 5, 7.5 μg/mL) for 72 hours. Human glioblastoma 05-MG cells were treated with NBM-C-BCX-OS01 (1.0, 2.0, 4.0 μg/mL) and NBM-C-BMX-OS01 (1.0, 2.0, 4.0 μg/mL) for 72 hours. Human glioma Hs683 cells were treated with NBM-C-BCX-OS01 (1.0, 2.0, 4.0 μg/mL). For cell cycle analysis, cells were fixed in 80% ethanol for 1 hour (or overnight) at −20° C. and then incubated with 2 μg/mL RNase A for 30 minutes at 37° C. Cells were stained with propidium iodide (5 g/mL PI) in PBS and analyzed using a Becton Dickinson flow cytometer, BD FACScan and CellQuest acquisition and analysis programs. The results of FIG. 1(c) show that NBM-HB-OS01 arrested the human lung cancer A549 cells on the G0/G1 phase in a dose-dependent manner. Human lung cancer A549 cells were inhibited by various concentrations (2.5, 5, 7.5 μg/mL) of NBM-C-BCX-OS01 and NBM-C-BMX-OS01 for 72 hours (see FIG. 6(c)) and Human glioblastoma 05-MG cells were inhibited by various concentrations (1.0, 2.0, 4.0 μg/mL) of NBM-C-BCX-OS01 and NBM-C-BMX-OS01 for 72 hours (see FIG. 6(d)). Human glioma Hs683 cells were treated with NBM-C-BCX-OS01 (1.0, 2.0, 4.0 μg/mL) for 72 hours. NBM-C-BCX-OS01 could arrest the growth of Human glioma Hs683 cells (see FIG. 6(e)).

Example 11

Up-Regulation of the HDAC Associated Proteins was Observed after Treatment of the Compounds of the Inventions Rat C6 glioma cells, Human breast cancer MCF-7 cells, and Human lung cancer A549 cells were seeded in 6-well plates. After 24 hrs of incubation in medium+10% BSA, Human breast cancer MCF-7 cells were treated with NBM-HB-OS01 (10.0 µg/mL) and vorinostat (SAHA, 5 µM) for 24 hours. Rat C6 glioma cells were treated with NBM-C-BX-OS01 (7.5 µg/mL) and vorinostat (SAHA, 5 µM) for 6 hours. Human lung cancer A549 cells were treated with NBM-C-BA-OS01 (7.5 µg/mL) and vorinostat (SAHA, 5 µM) for 6 hours. The treated cells were fixed in 80% methanol for 30 minutes and then washed 3 times with PBS solution. Cells were permeabilized with 0.3% Triton X-100 for 30 minutes, and then blocked in 10% fetal bovine serum (FBS) in PBS-T (0.1% Twin 20 in PBS) for 1 hour. The treated cells were detected with primary antibody against acetyl-Histone H3, acetyl-tubulin, and Gelsolin. Photographs were taken with a Nikon microscope. The results indicated that the compounds of the invention could induce the HDAC associated proteins expression of the various cancer cells (see FIG. 1(g), FIG. 2(e), and FIG. 3(c)).

Example 12

Increased Accumulation of Hyperacetylated Histone and Tubulin and p21 in Various Cell Lines Treated with the Compound of the Invention Rat C6 glioma cells and Human breast cancer MCF-7 cells were seeded 5×10⁵ cells in a 60-mm dish or 1×10⁶ cells in a 100-mm dish. After 24 hours, Rat C6 glioma cells were treated with various concentrations of NBM-HB-OS01 (2.5, 5.0, 7.5, 10.0 µg/mL) for 72 hours and were treated with 10.0 µg/mL NBM-HB-OS01 for 1, 2, 3, and 4 hours. Human breast cancer MCF-7 cells were treated with 7.5 µg/mL NBM-C-BX-OS01 for 1, 2, 3, and 4 hours. Lysates of C6, and MCF-7 cells were prepared for the immunoblotting of acetyl-Histone H3 (Cell Signaling Technology, Inc.), acetyl-Histone H4 (Upstate), acetyl-tubulin (Sigma Chemical Co.), p21 (BD Pharmingen Technology, Inc.), and actin (Sigma Chemical Co.). Proteins were detected by chemiluminescence (ECL, Amersham). The results indicated that the accumulation of hyperacetylated histone H3, hyperacetylated histone H4, acetylated-tubulin, and p21 were induced in Rat C6 glioma and MCF-7 cells (see FIG. 1(e), FIG. 1(f), and FIG. 2(d)). β-actin is an internal control.

Example 13

Figure 7:
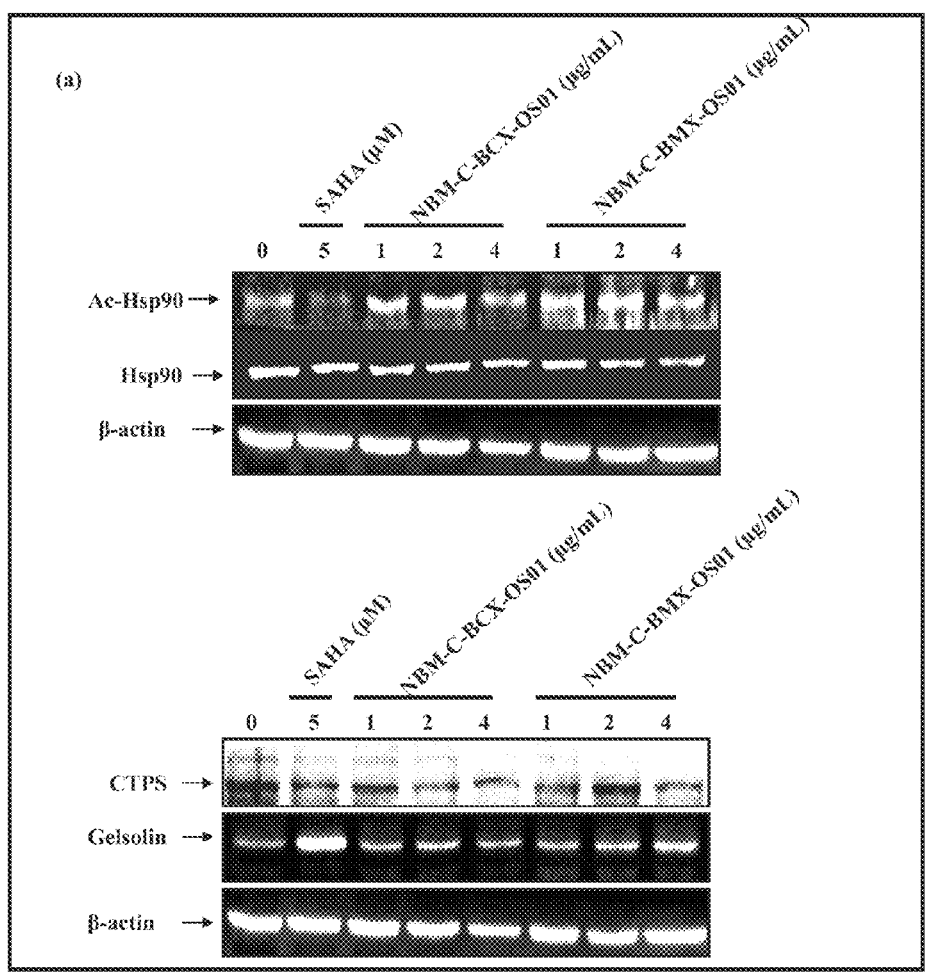
FIG. 7 shows the effects of NBM-C-BCX-OS01 and NBM-C-BMX-OS01 on histones and associated proteins. Human glioma Hs683 cells were treated with various concentrations of NBM-C-BCX-OS01 and NBM-C-BMX-OS01 for 72 hrs.
Figure 7:
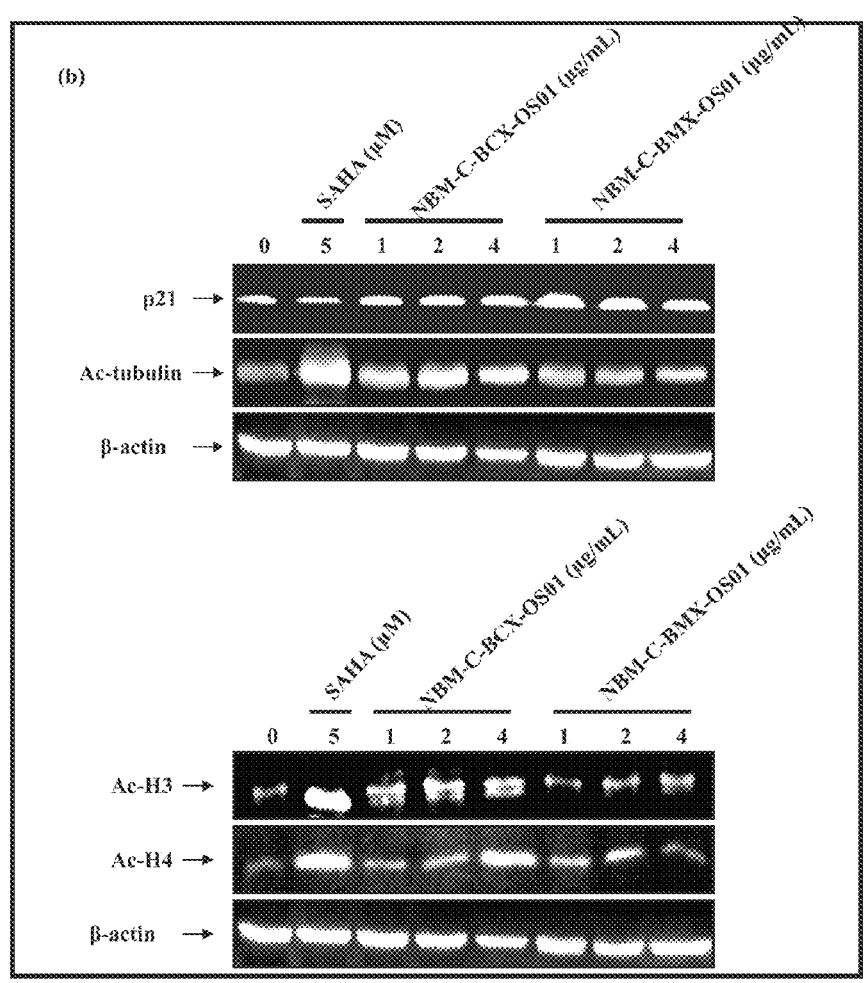
Figure 8:
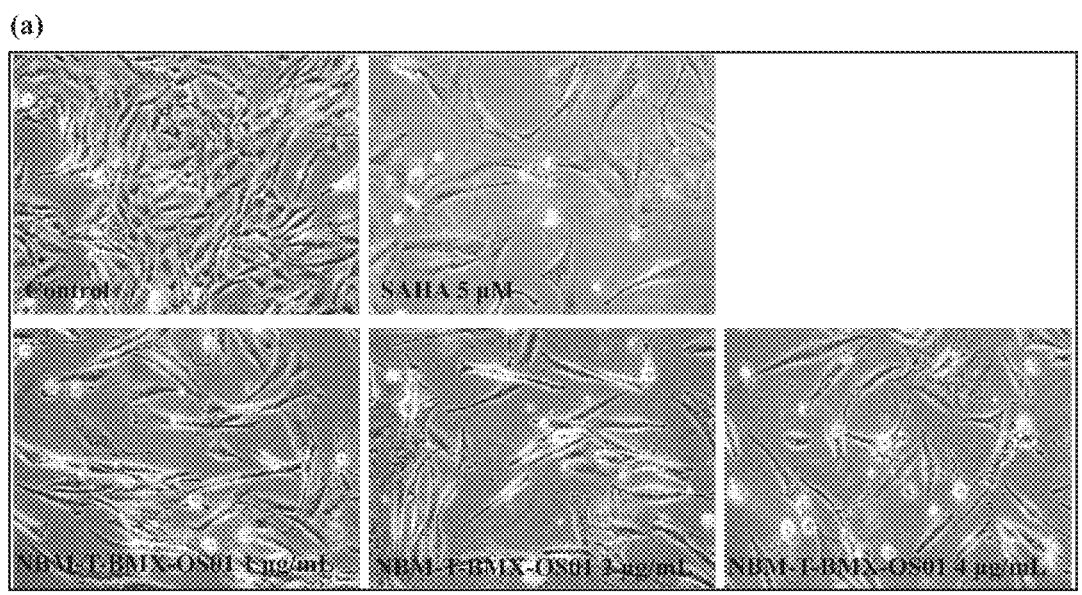
FIG. 8 shows the effects of: (a) NBM-T-BMX-OS01 (4b), (b) NBM-T-BCX-OS01 (4d), (c) NBM-T-BBX-OS01 (4e) and NBM-C-BBX-OS01 (4e), and (d) NBM-I-BCX-OS01 on the inhibition of cell growth (see FIGS. 8(a) to (d)). Human glioma Hs683 cells were grown in the presence of the above compounds of various concentrations (1.0, 2.0 and 4.0 μg/mL) for 72 hours. The treated cells counted by a trypan blue exclusion assay are plotted in FIG. 8(e).
Figure 8:
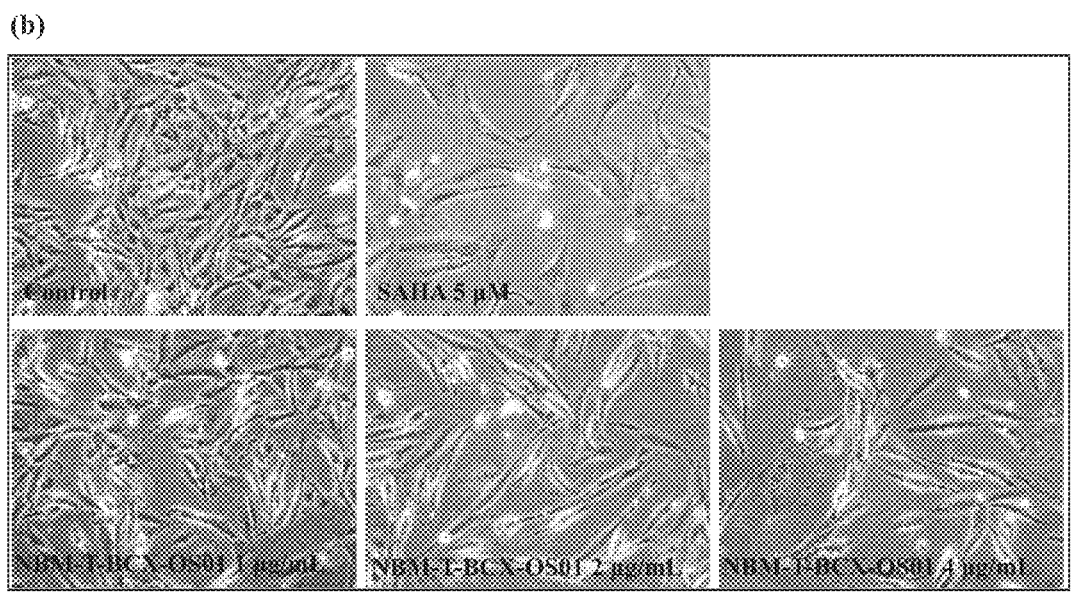
Figure 8:
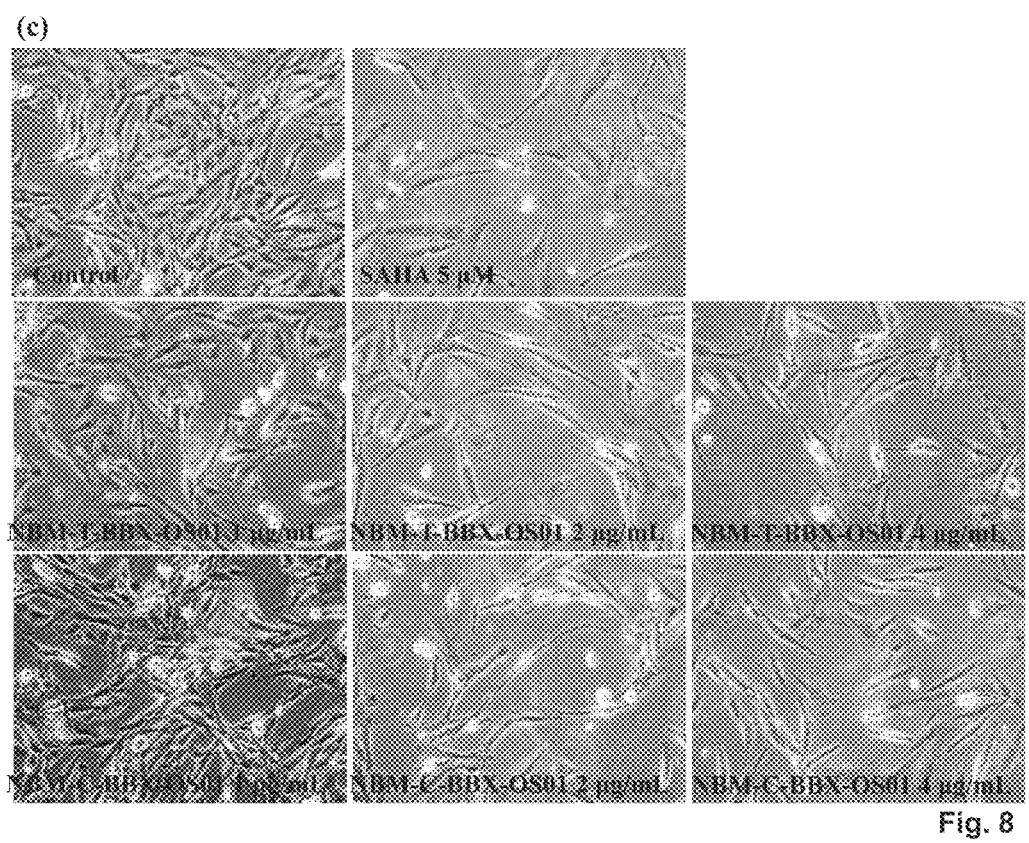
Figure 8:
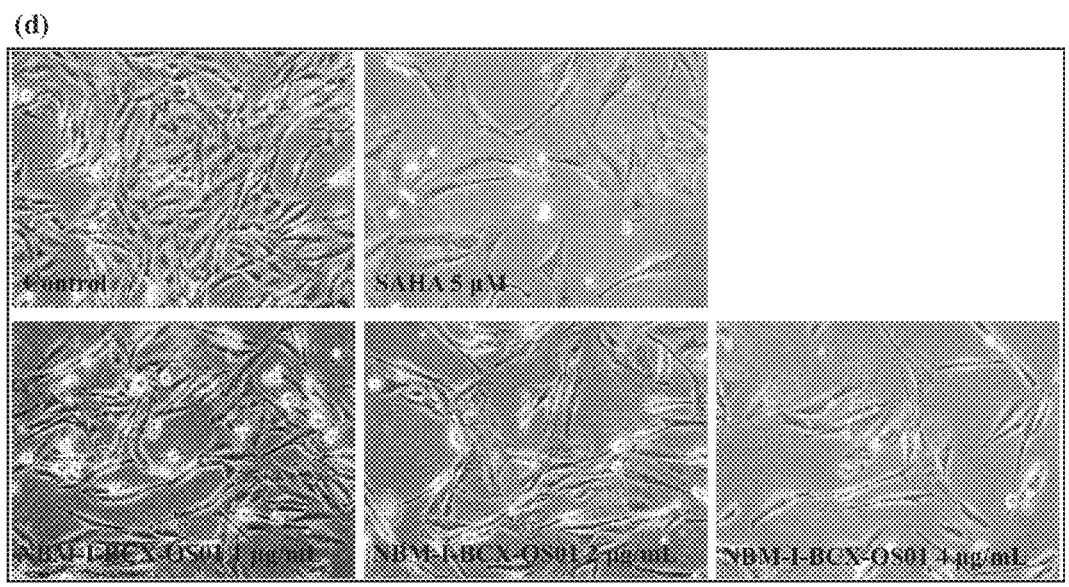
Figure 8:
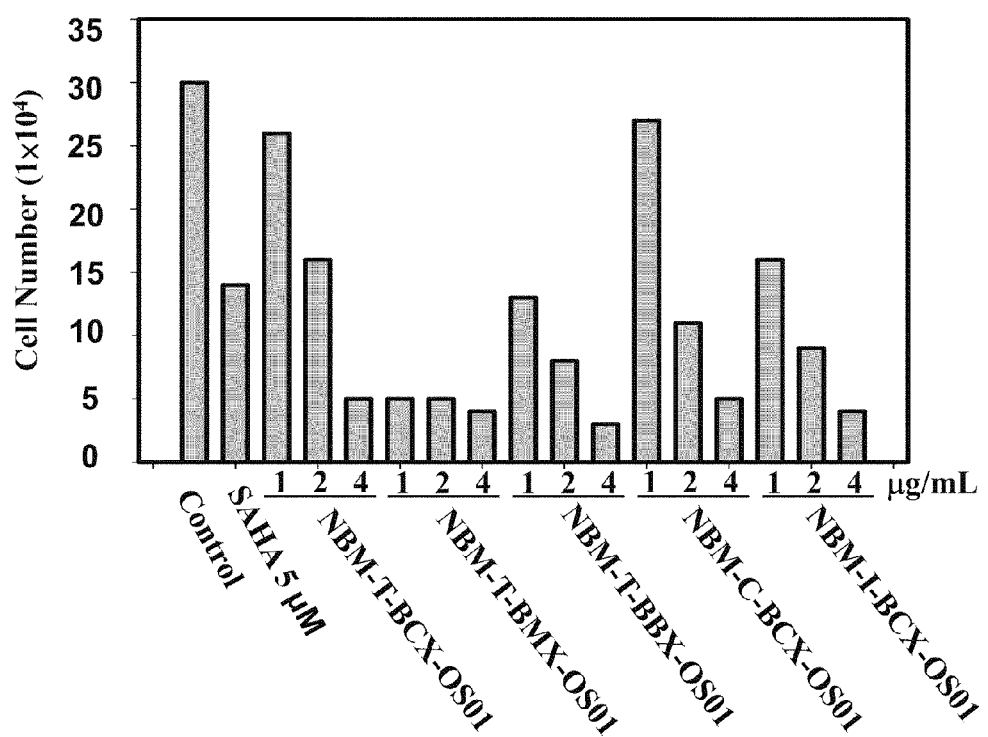
Figure 9:
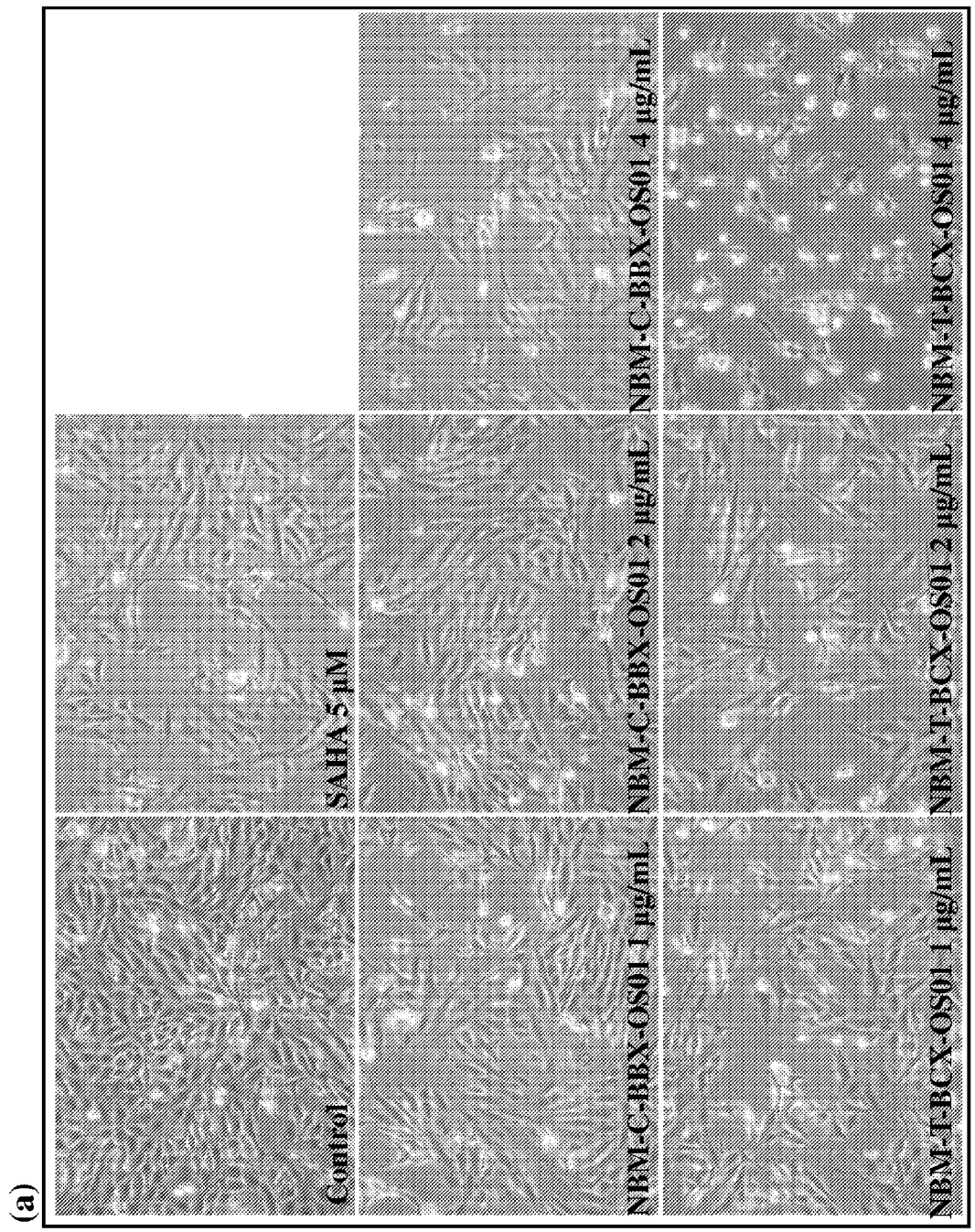
FIG. 9 shows the effects of (a) NBM-C-BBX-OS01 and NBM-T-BCX-OS01, (b) NBM-T-BBX-OS01 and NBM-I-BCX-OS01, (c) NBM-T-BMX-OS01, (d) NBM-I-BCX-OS01 and NBM-T-BMX-OS01 and (e) NBM-T-BBX-OS01 on the inhibition of human breast cancer MDA-MB-231 cells (see FIGS. 9(a) to (e)). The results of trypan blue exclusion assay are shown in FIG. 9(f).
Figure 9:
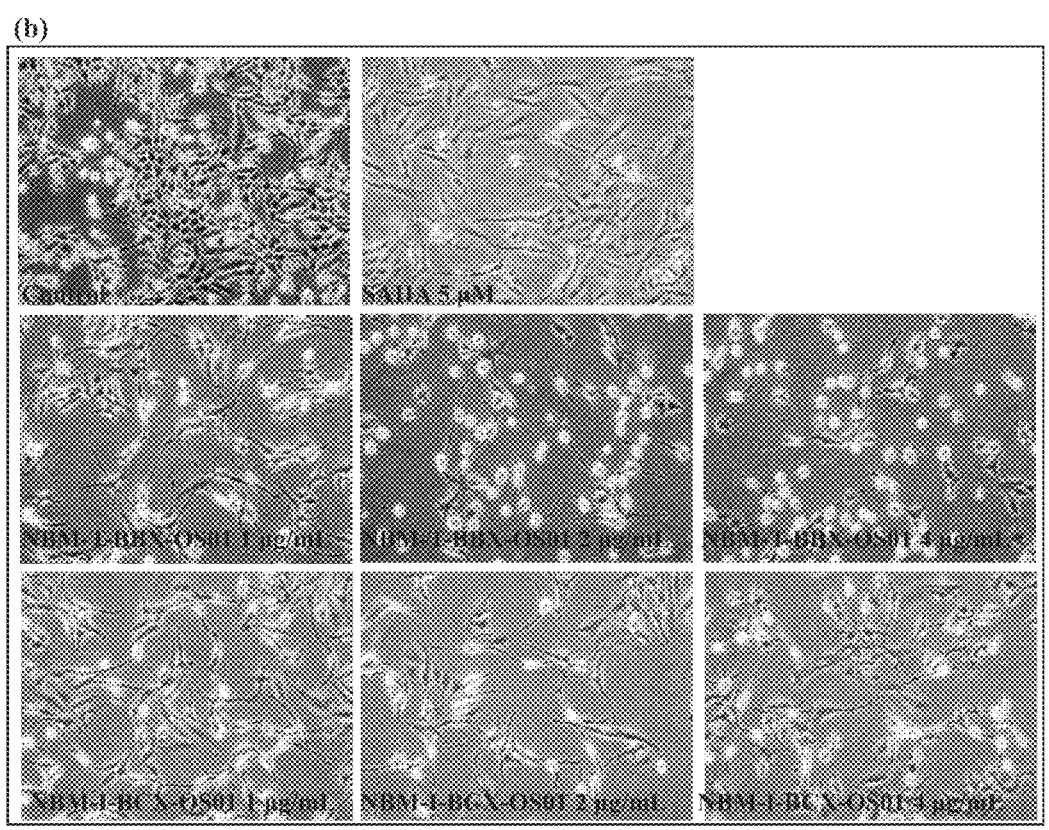
Figure 9:
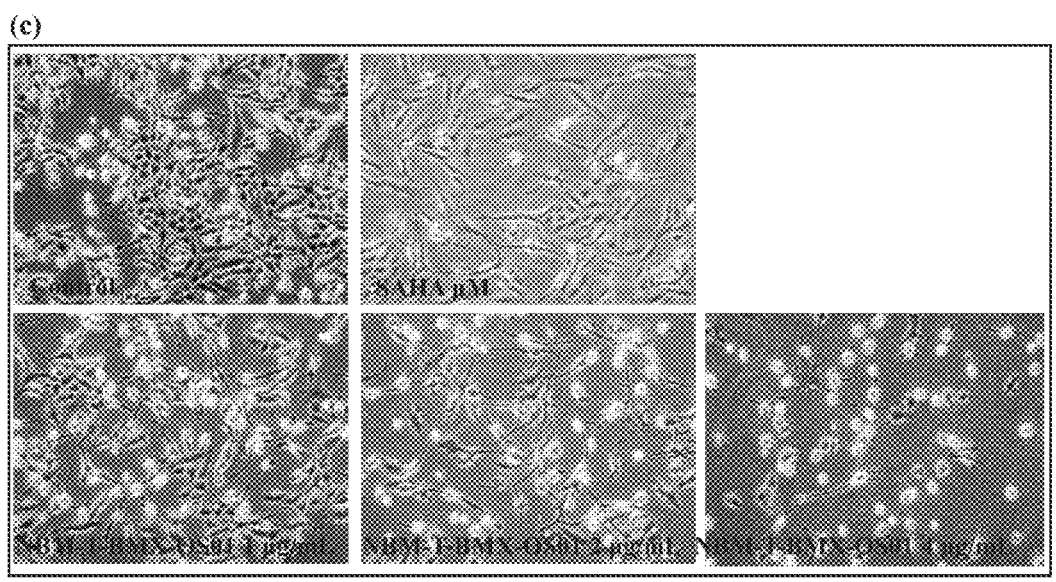
Figure 9:
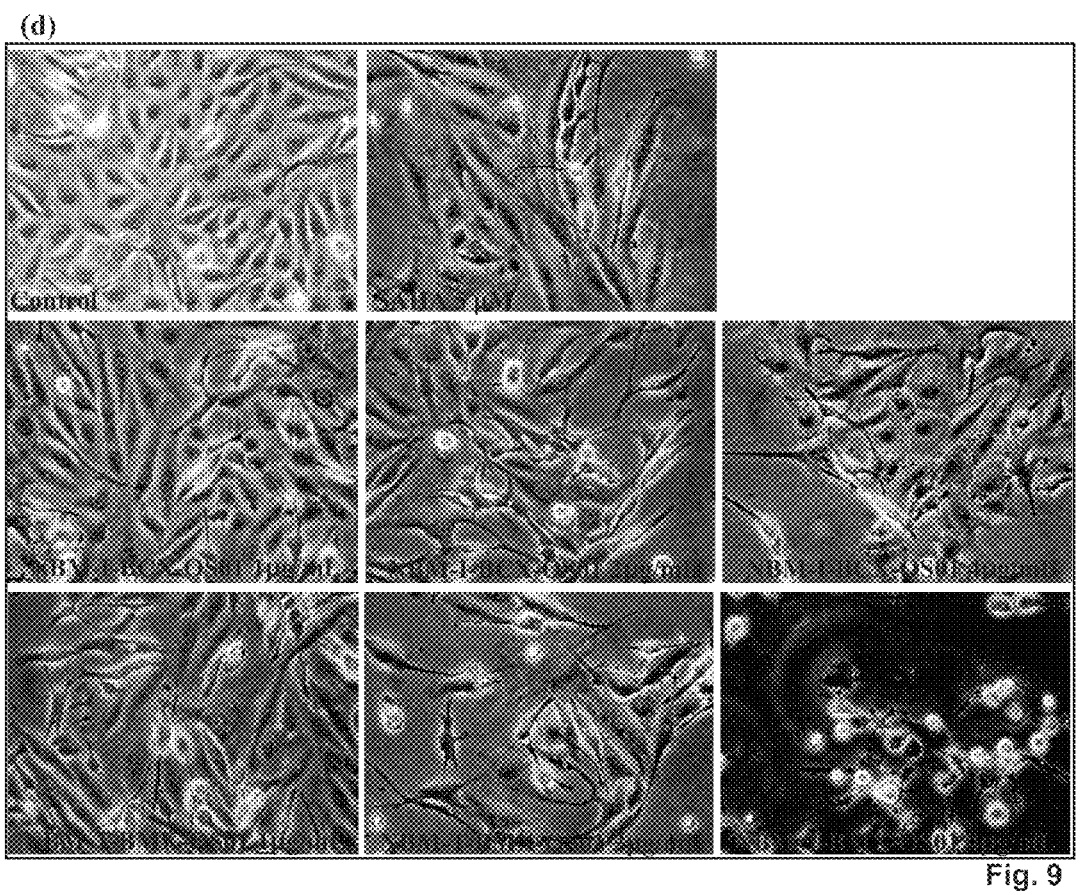
Figure 9:
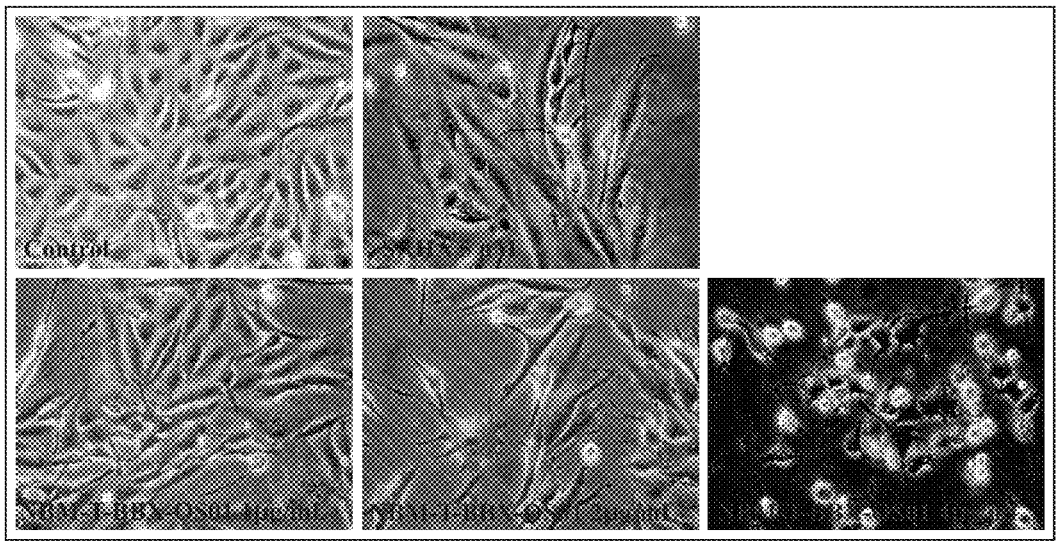
Figure 9:
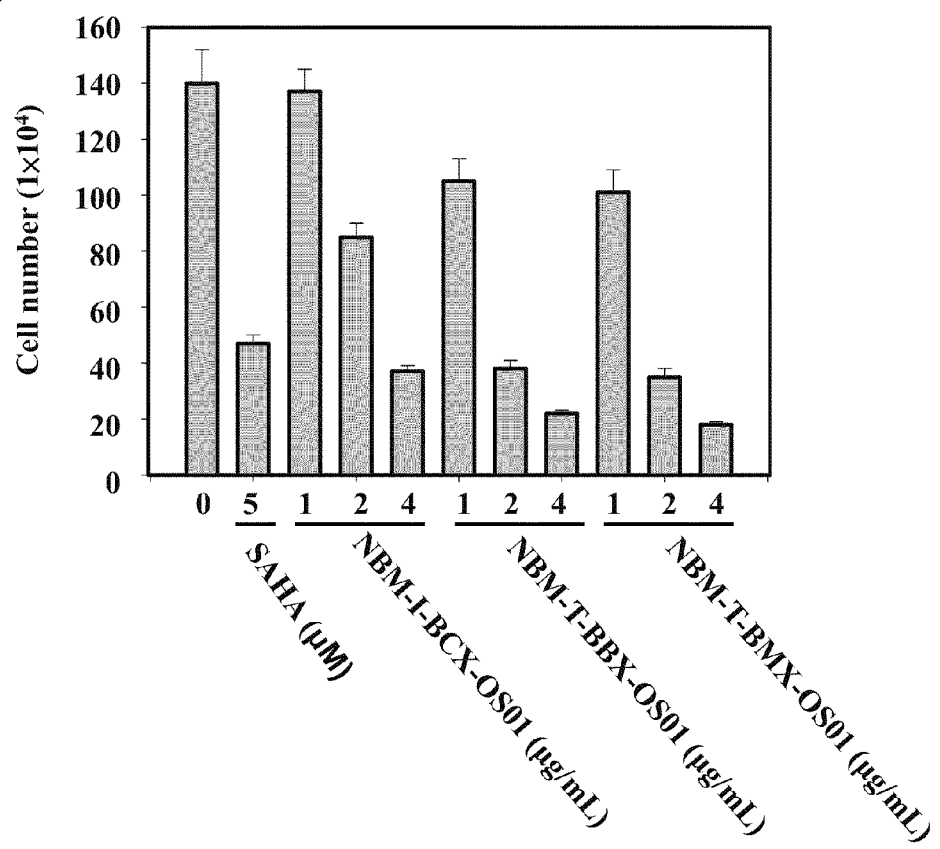
Figure 10:
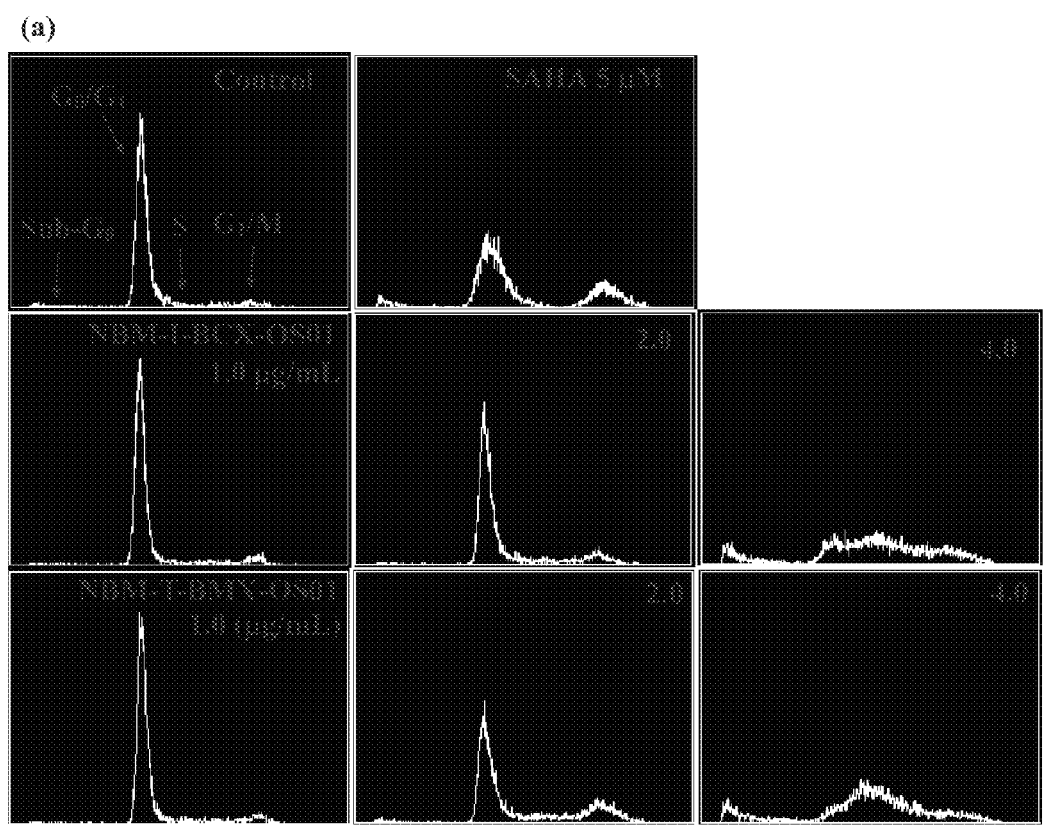
FIG. 10 shows that (a) NBM-I-BCX-OS01 and NBM-T-BMX-OS01, and (b) NBM-T-BBX-OS01 and NBM-C-BBX-OS01 arrested the human lung cancer A549 cells on the S and G2/M phases (see Figs. (a) and (b)). The results were similar to those in Human breast cancer MCF-7 cells (see FIGS. 10(c) and, (d)).
Figure 10:
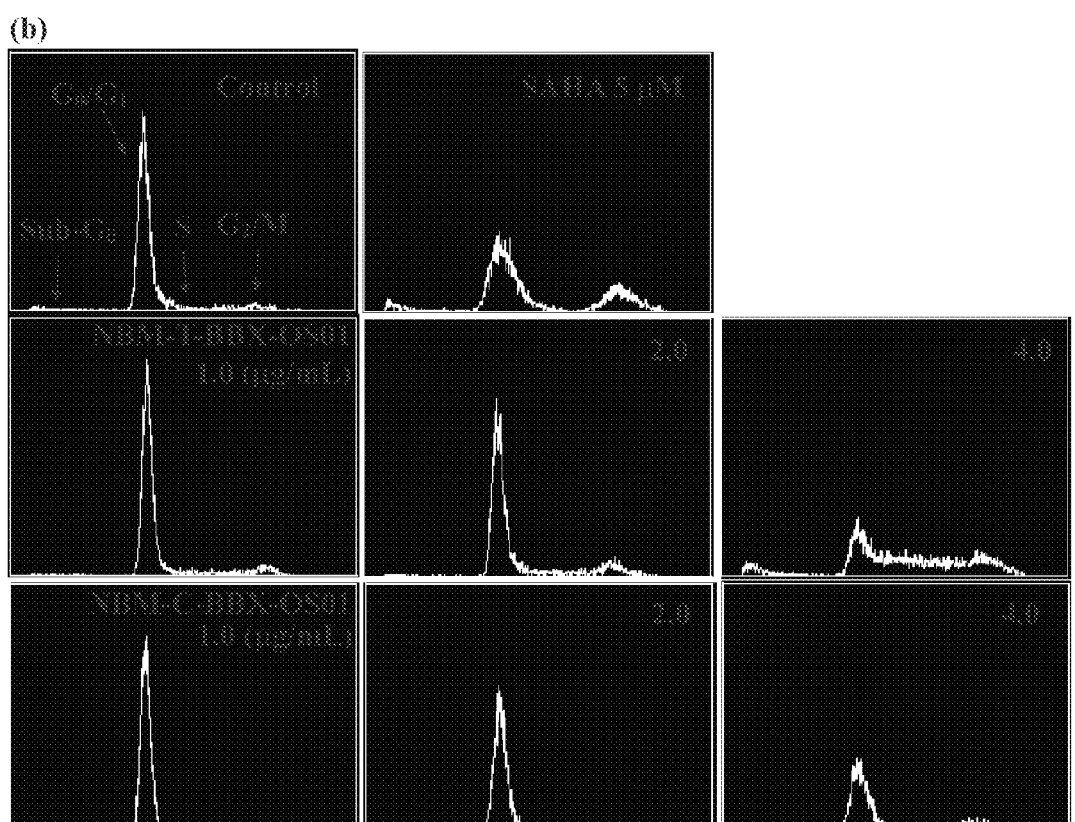
Figure 10:
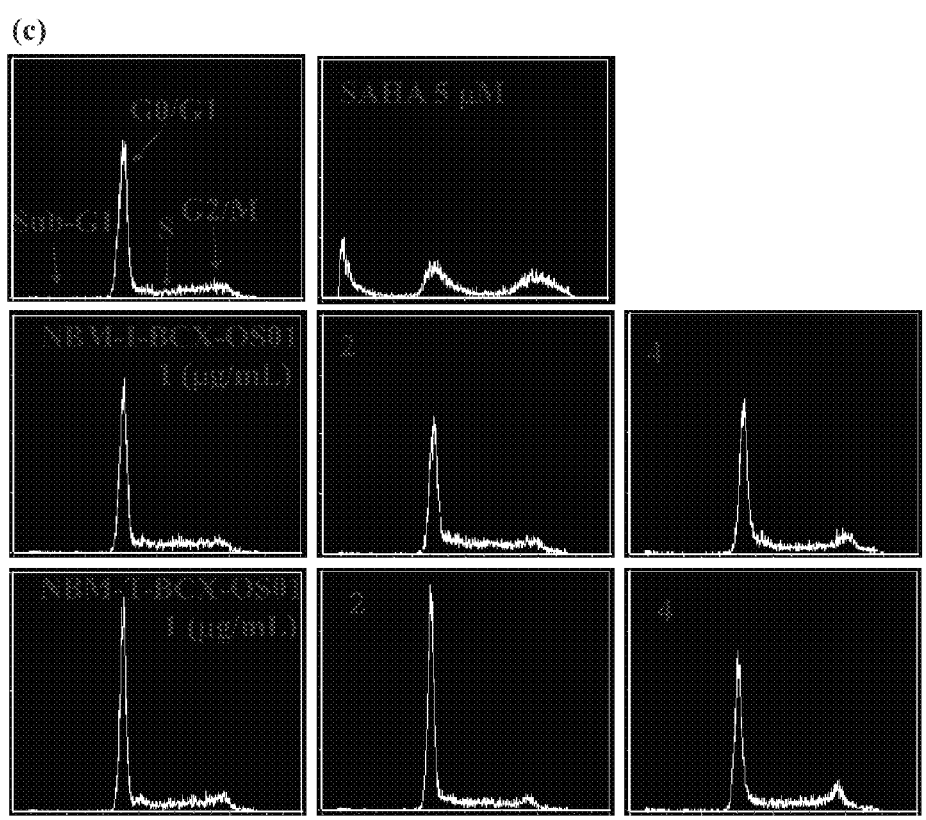
Figure 10:
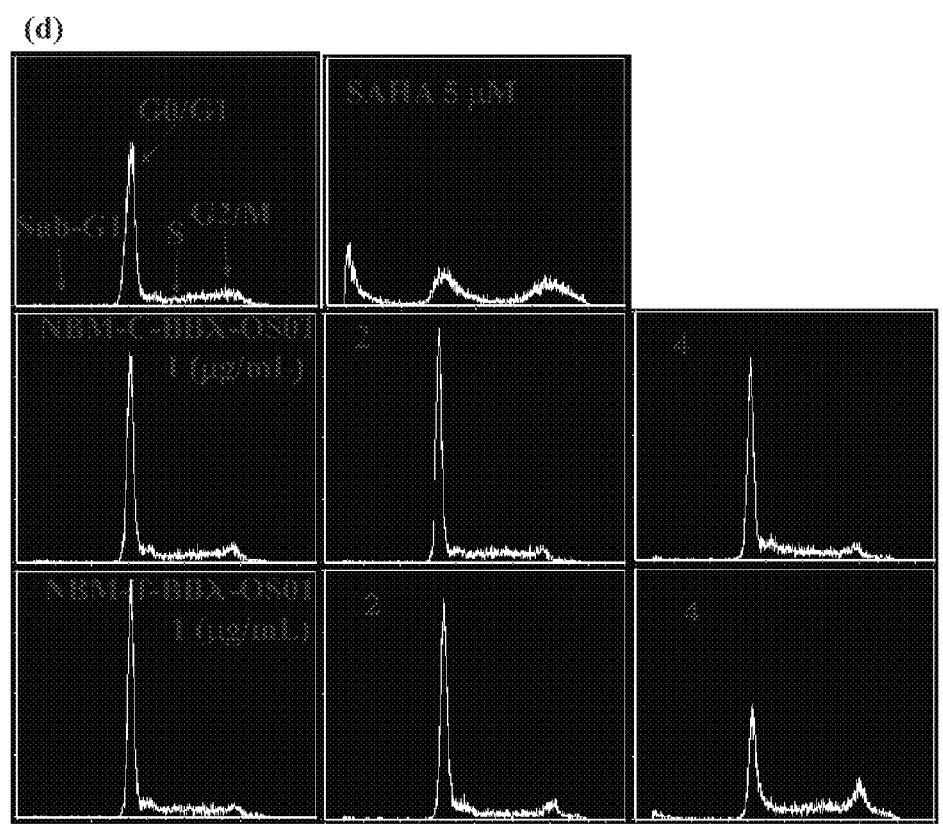
Figure 10:
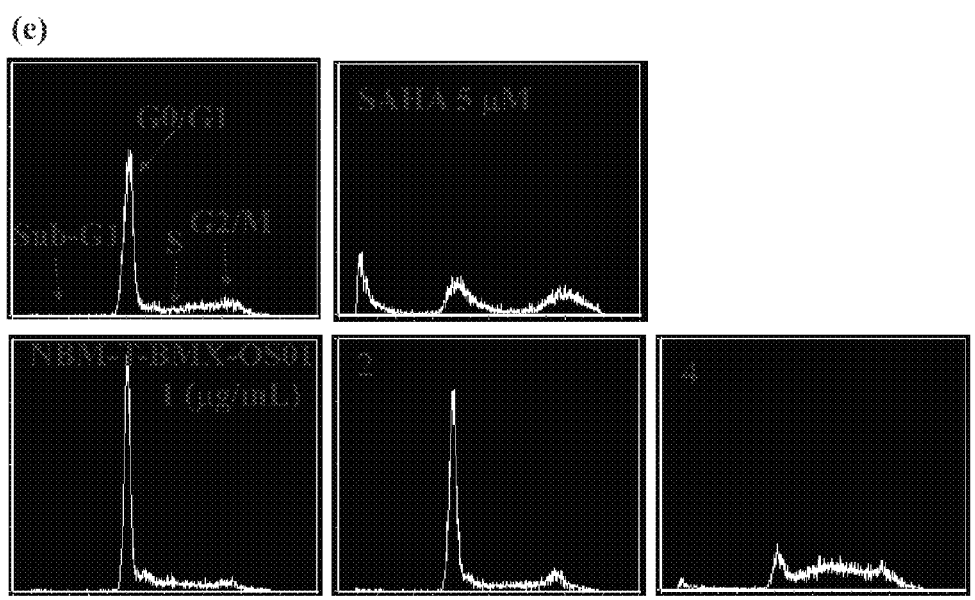

Effects of NBM-C-BCX-OS01 and NBM-C-BMX-OS01 on Histones and the HDAC Associated Proteins Human glioma Hs683 cells were seeded at 5×10⁵ cells in a 60-mm dish or 1×10⁶ cells in a 100-mm dish. After 24 hours, Human glioma Hs683 cells were treated with different doses of NBM-C-BCX-OS01, NBM-C-BMX-OS01 (1.0, 2.0, 4.0 µg/mL), and vorinostat (SAHA, 5 µM) for 72 hours. Lysates of Hs683 cells were prepared for the immunoblotting of acetyl-Histone H3 (Cell Signaling Technology, Inc.), acetyl-Histone H4 (Upstate), acetyl-tubulin (Sigma Chemical Co.), p21 (BD Pharmingen Technology, Inc.), CTPS (ABNOVA TAIWAN Corporation), Gelsolin (Sigma Chemical Co.), Hsp90 (Cell Signaling Technology, Inc.), acetyl-Hsp90 (ROCKLAND, Inc.) and actin (Sigma Chemical Co.). Proteins were detected by chemiluminescence (ECL, Amersham). The increase of acetylated Hsp90 and gelsolin proteins was observed in a dose-dependent manner. Hsp90 and CTPS proteins were decreased in a dose-dependent manner (see FIG. 7(a)). The expression of p21, acetylated tubulin, acetylated Histone H3, and acetylated Histone H4 was induced in a dose-dependent manner. SAHA was used as a positive control and β-actin as an internal control (see FIG. 7(b)).

What is claimed is:
1. A compound represented by the following formula (I):

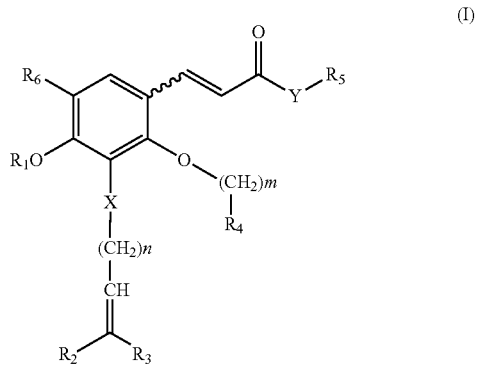

wherein
R₁ is hydrogen, alkyl, alkenyl, C₃₋₈ cycloalkyl, 5-membered or 6-membered unsaturated carbocycle or 5-membered or 6-membered heterocycle;
X is C, O, N or S;
Y is O, NH or O—C₁₋₄alkyl;
n is an integer of 0 to 10;
m is an integer of 1 to 5;
R₂ and R₃ is independently C₁₋₆ alkyl;
R₄ is C₅₋₆ cycloalkyl or 5-membered or 6-membered unsaturated carbocycle or heterocycle which may be substituted with halogen, CF₃, OR₇ or NR₇R₈, wherein R₇ and R₈ are independently hydrogen or C₁₋₆ alkyl;
R₅ is OH, NH₂ or C₅₋₆ cycloalkyl, 5-membered or 6-membered unsaturated carbocycle or heterocycle wherein the cycloalkyl, carboycle and heterocycle may be optionally substituted with halogen, NH₂, NO₂, C₁₋₆ alkoxy, C₁₋₆ alkylthio, OR₇, NR₇R₈ or CF₃; and
R₆ is H, C₁₋₁₀alkyl which may be substituted by hydroxy or C₂₋₁₀alkenyl, or together with R₁ being —C₂H₂—;
and pharmaceutically acceptable salts, stereoisomers, and enantiomers thereof.

2. The compound according to claim 1, wherein R₁, R₂ and R₃ are independently C₁₋₄ alkyl; R₄ is phenyl or phenyl substituted with halogen, CF₃, OC₁₋₄ alkyl, R₅ is OH, phenyl or phenyl substituted with NH₂ and R₆ is hydrogen.

3. The compound according to claim 1, wherein R₁, R₂ and R₃ are independently methyl, R₄ is phenyl or phenyl substituted with F, Cl, Br, CF₃, OCH₃, R₅ is OH or phenyl substituted with NH₂ and R₆ is hydrogen.

4. The compound according to claim 1, wherein X is carbon.

5. The compound according to claim 1, wherein n and m is 1.

6. The compound according to claim 1, wherein the carbocycle is cycloalkenyl or aryl.

7. The compound according to claim 6, wherein the cycloalkenyl is selected from the group consisting of cyclopropenyl, cyclobutenyl, cyclopentenyl, cyclohexenyl, cycloheptenyl and cyclooctenyl, and the aryl is selected from the group consisting of phenyl, naphthyl and tetrahydronaphthalenyl.

8. The compound according to claim 1, wherein the 5-membered or 6-membered unsaturated heterocycle is selected from the group consisting of furyl, thienyl, pyrrolyl, imidazolyl, pyrazolyl, triazolyl, tetrazolyl, oxazolyl, isoxazolyl, thiazolyl, thiadiazolyl, isothiazolyl, pyridyl, pyridazinyl, pyrimidinyl, furazanyl, pyrazinyl, oxadiazolyl, 1-pyrrolinyl, 2-pyrrolinyl, 3-pyrrolinyl, pyrrolidino, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidyl, 3-piperidyl, 4-piperidyl, piperazino, 2-piperazinyl, 2-morpholinyl, 3-morpholinyl, morpholino and tetrahydropyranyl.

9. The compound according to claim 1, which is selected from the group consisting of:

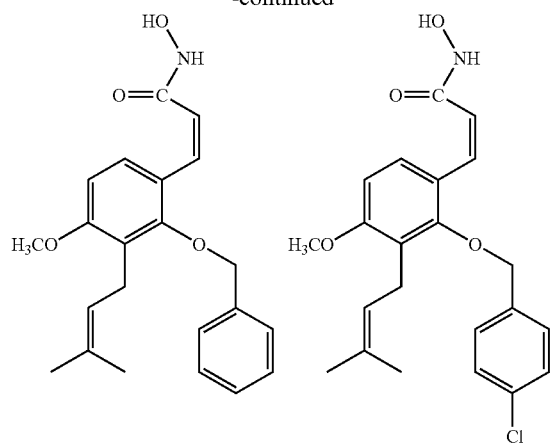

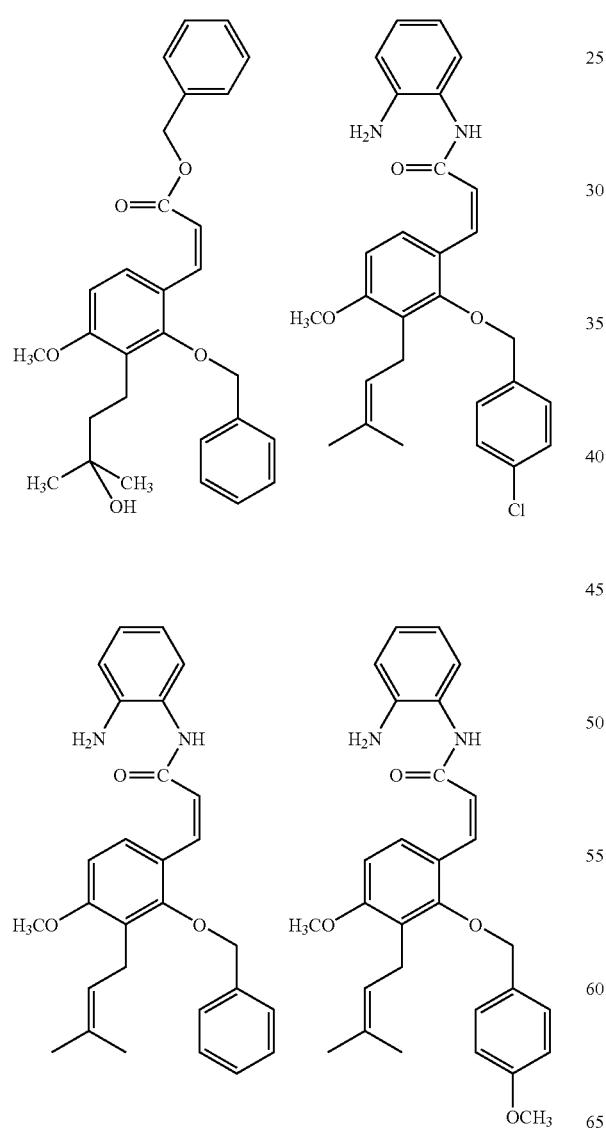

-continued

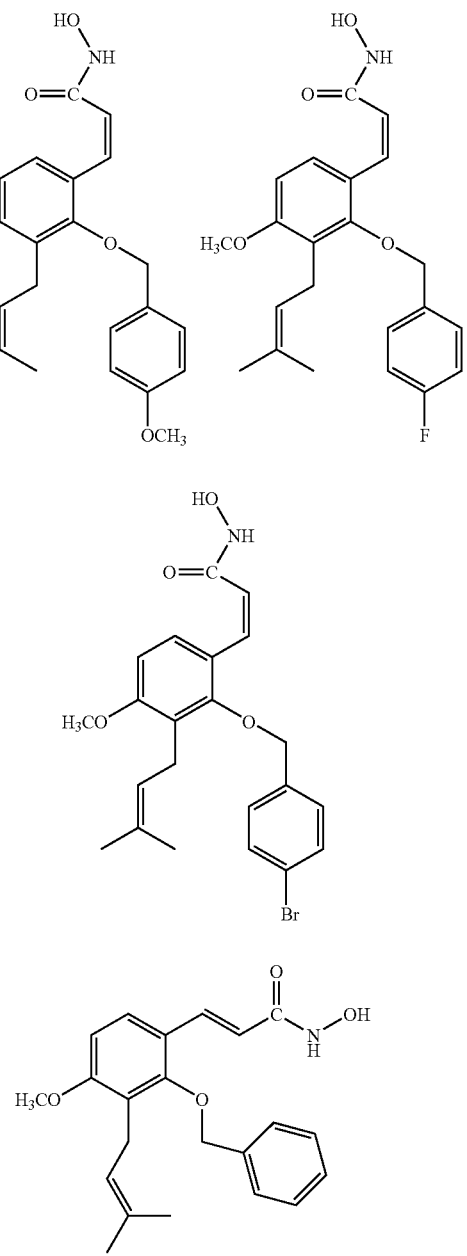

61
-continued
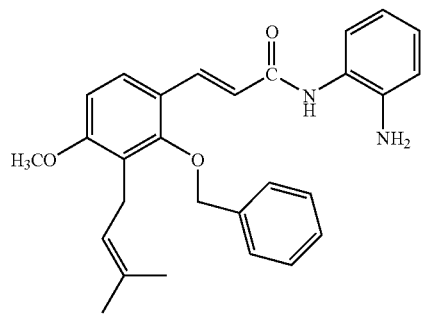
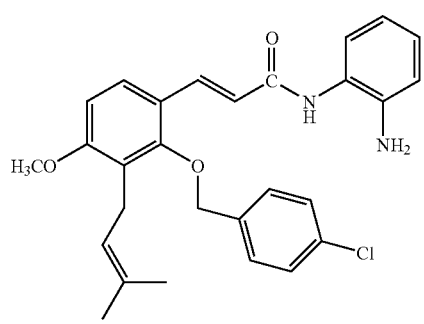
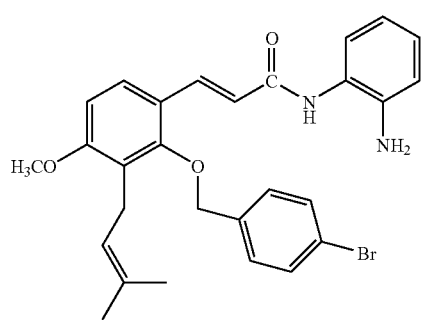
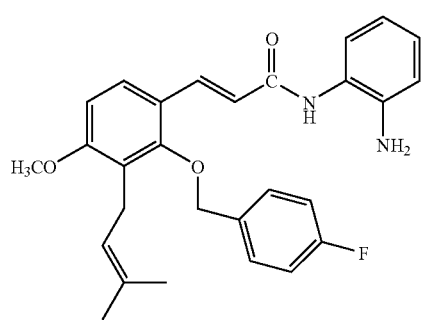
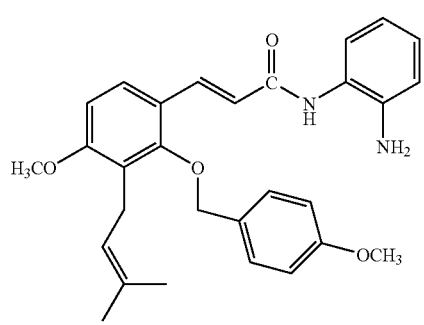
62
-continued
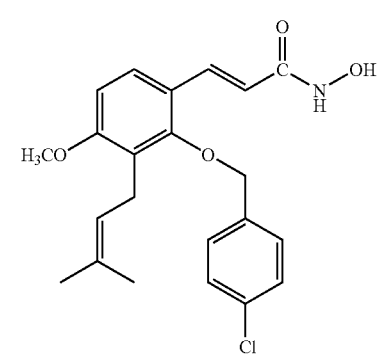
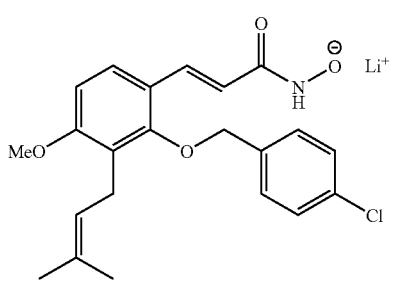
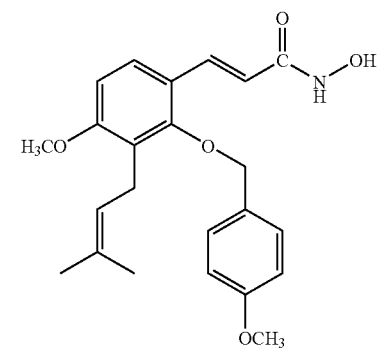
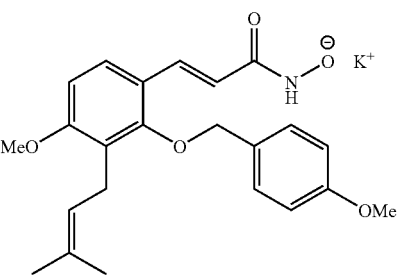
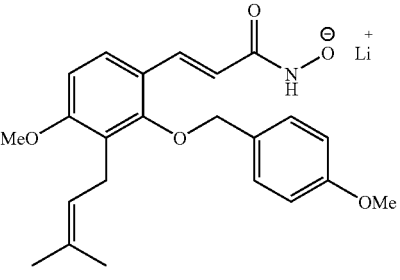

63
-continued
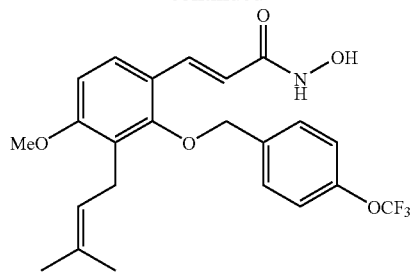
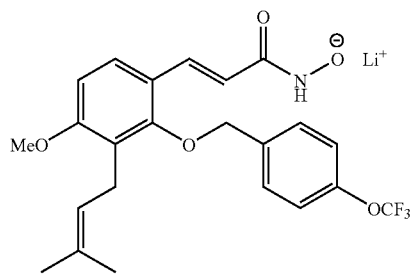
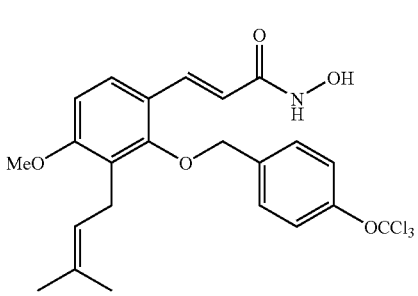
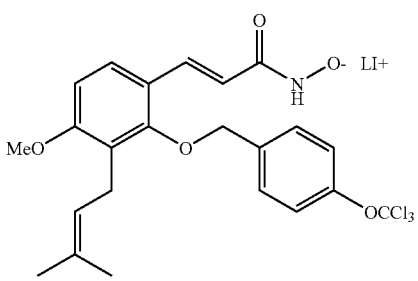
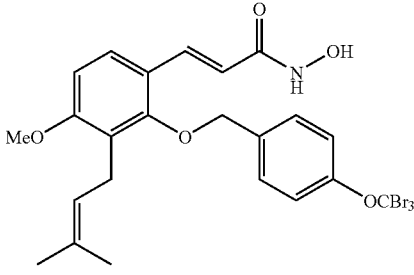
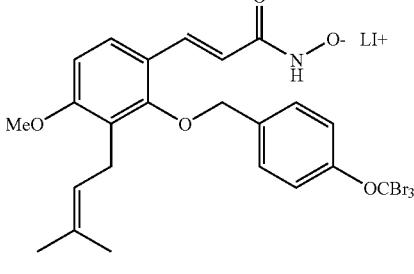
64
-continued
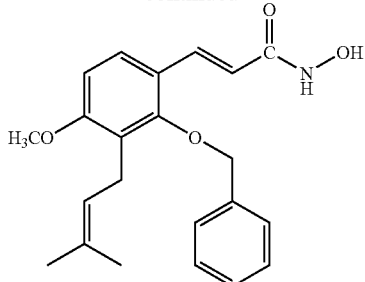
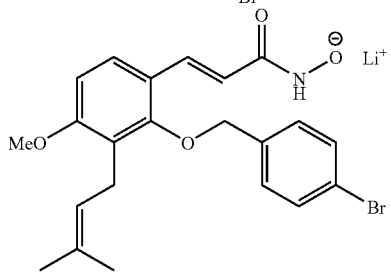
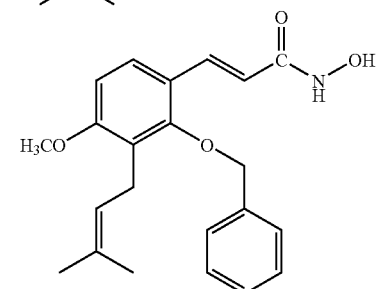
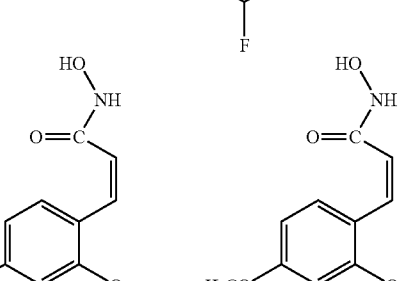
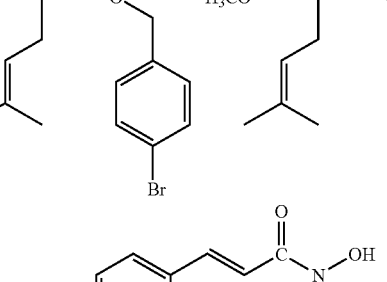
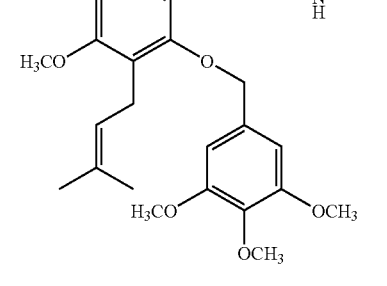

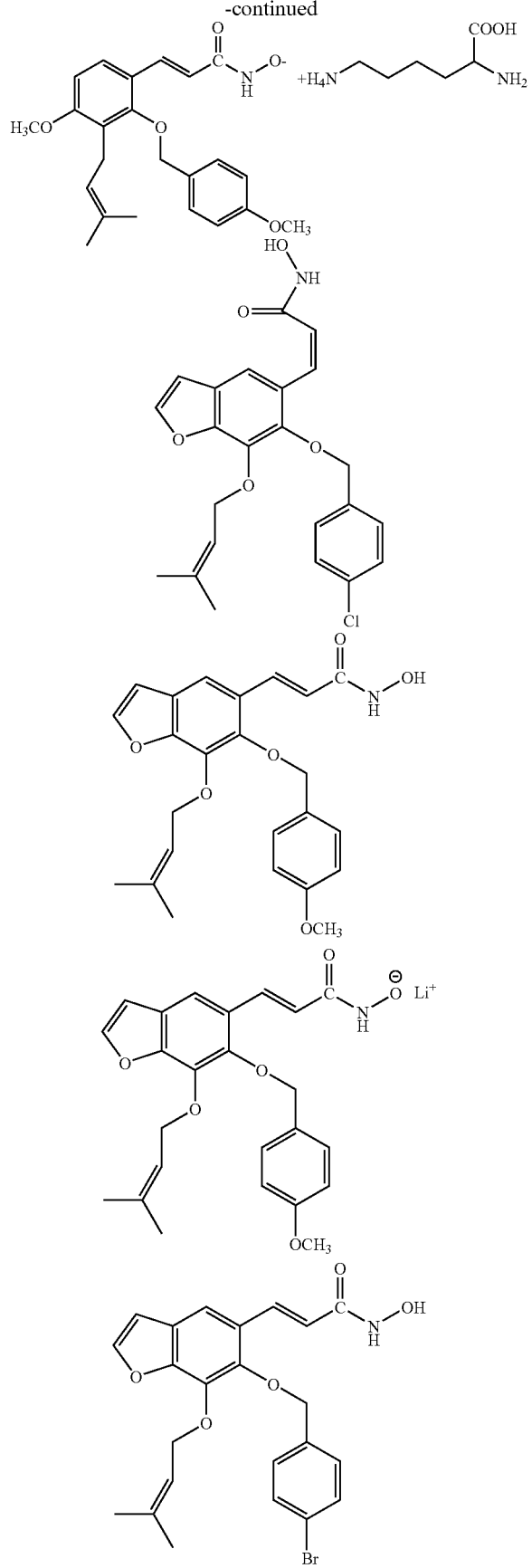
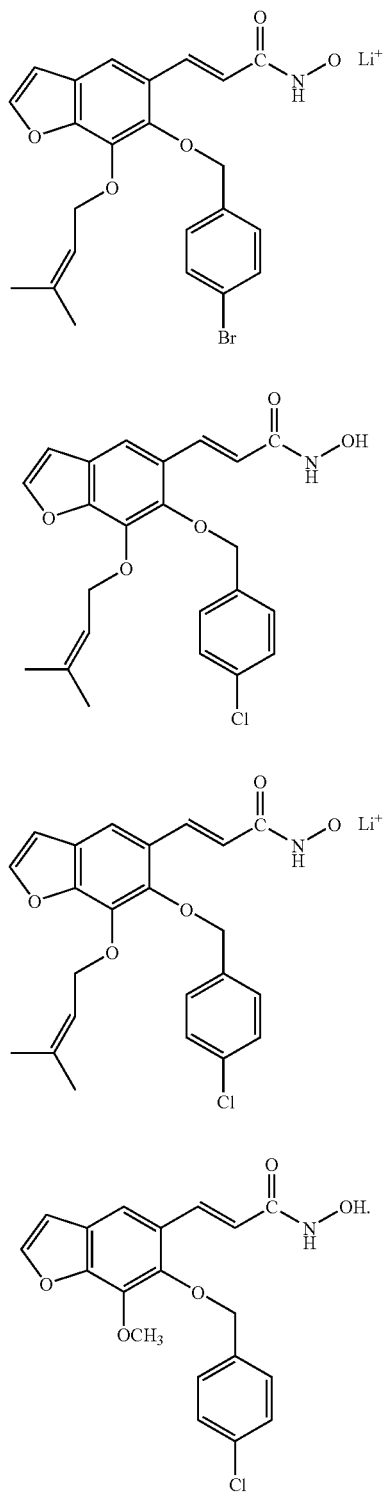
10. A pharmaceutical composition comprising the compound of claim 1 or pharmaceutically acceptable salts, stereoisomers, and enantiomers thereof as an active ingredient and a pharmaceutically acceptable carrier.
* * * * *